(12) United States Patent
Carter et al.

(10) Patent No.: US 8,354,432 B2
(45) Date of Patent: *Jan. 15, 2013

(54) CYCLIC DERIVATIVES AS MODULATORS OF CHEMOKINE RECEPTOR ACTIVITY

(75) Inventors: Percy H. Carter, Princeton, NJ (US); Lyndon A. M. Cornelius, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 551 days.

This patent is subject to a terminal disclaimer.

(21) Appl. No.: 12/444,249

(22) PCT Filed: Oct. 3, 2007

(86) PCT No.: PCT/US2007/080238
§ 371 (c)(1),
(2), (4) Date: Nov. 10, 2009

(87) PCT Pub. No.: WO2008/042925
PCT Pub. Date: Apr. 10, 2008

(65) Prior Publication Data
US 2010/0063067 A1    Mar. 11, 2010

Related U.S. Application Data

(60) Provisional application No. 60/849,367, filed on Oct. 4, 2006, provisional application No. 60/976,829, filed on Oct. 2, 2007.

(51) Int. Cl.
*A61K 31/454* (2006.01)
*C07D 401/06* (2006.01)
(52) U.S. Cl. ......... 514/326; 546/208
(58) Field of Classification Search ......... 514/326; 546/208
See application file for complete search history.

(56) References Cited

U.S. PATENT DOCUMENTS
2010/0093798 A1 * 4/2010 Carter .......................... 514/323

FOREIGN PATENT DOCUMENTS
| | | |
|---|---|---|
| EP | 0449186 | 10/1991 |
| WO | WO 98/37079 | 8/1998 |
| WO | WO 01/14333 | 3/2001 |
| WO | WO2011/041152 | * 4/2011 |

OTHER PUBLICATIONS

Arnaiz et al. "Preparation of N-hetero . . ."CA129:231019 (1998).*
Pease et al. "CCR1 antagonists . . ." Exp. Opinion. Invest. Drug. v.14(7) p. 785-796 (2005).*
Pease et al. "Chemokine receptor . . ." Exp. Opinion. Ther. Patents v.19(1) p. 39-58 (2009).*
Shang et al. "Chemokine receptor 1 . . ." Am. J. Pathol. vo. 157(6) p. 2055-2063 (2000).*
Palani et al., Bioorganic & Medicinal Chemistry Letters, vol. 13, pp. 709-712 (2003).
Asim Kumar Debnath, Journal of Medicinal Chemistry, ACS, vol. 46, pp. 4501-4515 (2003).

* cited by examiner

*Primary Examiner* — Celia Chang
(74) *Attorney, Agent, or Firm* — Laurelee A. Duncan; Elliot Korsen

(57) ABSTRACT

The present application describes modulators of MIP-1α of formula (I), or stereoisomers or prodrugs or pharmaceutically acceptable salts thereof, wherein n, A, T, $R_1$, $R_2$ and $R_8$, are as defined herein. In addition, methods of treating and preventing inflammatory diseases such as asthma and allergic diseases, as well as autoimmune pathologies such as rheumatoid arthritis and atherosclerosis using the modulators of formula (I) are disclosed.

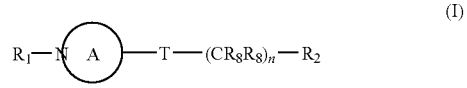

(I)

7 Claims, No Drawings

CYCLIC DERIVATIVES AS MODULATORS OF CHEMOKINE RECEPTOR ACTIVITY

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, monocytes, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (−1 and −2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik and Oshie, *Immunity* 2000, 12, 121): CCR-1 (or "CKR-1" or "CC-CKR-1") [MIP-1α, MCP-3, MCP-4, RANTES] (Neote et al., Cell 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-1β] (Samson et al., *Biochemistry* 1996, 35, 3362-3367); CCR-6 (or "CKR-6" or "CC-CKR-6") [LARC] (Baba et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [I-309] (Napolitano et al., *J. Immunol.,* 1996, 157, 2759-2763); CCR-10 (or "CKR-10" or "CC-CKR-10") [MCP-1, MCP-3] (Bonini et al., *DNA and Cell Biol.* 1997, 16, 1249-1256); and CCR-11 [MCP-1, MCP-2, and MCP-4] (Schweickart et al., *J. Biol. Chem.* 2000, 275, 9550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: P. H. Carter, *Current Opinion in Chemical Biology* 2002, 6, 510; Trivedi et al., *Ann. Reports Med. Chem.* 2000, 35, 191; Saunders and Tarby, *Drug Disc. Today* 1999, 4, 80; Premack and Schall, *Nature Medicine* 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E., *J. Immun.* 2000, 164, 3392-3401).

Demonstration of the importance of the MIP-1α/CCR-1 interaction has been provided by experiments with genetically modified mice. MIP-1α−/− mice had normal numbers of leukocytes, but were unable to recruit monocytes into sites of viral inflammation after immune challenge (Cook, D. et al., *Science.* 1995, 269, 1583-1585). Recently, MIP-1α−/− mice were shown to be resistant to collagen antibody induced arthritis (Chintalacharuvu, S. R., *Immun. Lett.* 2005, 202-204). Likewise, CCR-1−/− mice were unable to recruit neutrophils when challenged with MIP-1α in vivo; moreover, the peripheral blood neutrophils of CCR-1 null mice did not migrate in response to MIP-1α (Gao, B. et al., *J. Exp. Med.* 1997, 185, 1959-1968), thereby demonstrating the specificity of the MIP-1α/CCR-1 interaction. The viability and generally normal health of the MIP-1α−/− and CCR-1−/− animals is noteworthy, in that disruption of the MIP-1α/CCR-1 interaction does not induce physiological crisis. Taken together, these data lead one to the conclusion that molecules that block the actions of MIP-1α would be useful in treating a number of inflammatory and autoimmune disorders. This hypothesis has now been validated in a number of different animal disease models, as described below.

It is known that MIP-1α is elevated in the synovial fluid and blood of patients with rheumatoid arthritis (Alisa Koch et al., *J. Clin. Invest.* 1994, 93, 921-928). Moreover, several studies have demonstrated the potential therapeutic value of antagonism of the MIP-1α/CCR1 interaction in treating rheumatoid arthritis (Pease, J. E. and Horuk, R. *Expert Opin. Invest. Drugs* 2005, 14, 785-796).

An antibody to MIP-1α was shown to ameliorate experimental autoimmune encepahlomytis (EAE), a model of multiple sclerosis, in mice (Karpus, W. J. et al., *J. Immun.* 1995, 5003-5010). Likewise, inflammatory disease symptoms could be controlled via direct administration of antibodies for MIP-1α to mice with collagen-induced arthritis (Lukacs, N. W. et al., *J. Clin. Invest.* 1995, 95, 2868-2876).

It should also be noted that CCR-1 is also the receptor for the chemokines RANTES, MCP-3, HCC-1, Lkn-1/HCC-2, HCC-4, and MPIF-1 (Carter, P. H., *Curr. Opin Chem. Bio.* 2002, 6, 510-525). Since it is presumed that the new compounds of formula (I) described herein antagonize MIP-1α by binding to the CCR-1 receptor, it may be that these compounds of formula (I) are also effective antagonists of the actions of the aforementioned ligand that are mediated by CCR-1. Accordingly, when reference is made herein to "antagonism of MIP-1α," it is to be assumed that this is equivalent to "antagonism of chemokine stimulation of CCR-1."

For example, demonstration of the chemotactic properties of RANTES in humans has been provided experimentally. Human subjects, when injected intradermally with RANTES, experienced an influx of eosinophils to the site of injection (Beck, L. A. et al., *J. Immun.* 1997, 159, 2962-2972). Likewise, a RANTES antibody has demonstrated the ability to ameliorate the symptoms of disease in the rat Adjuvant induced arthritis (AIA) model (Barnes, D. A. et al., *J. Clin Invest.* 1998, 101, 2910-2919). Similar results were obtained when using a peptide derived antagonist of the RANTES/CCR-1 interaction in both the rat AIA (Shahrara, S. et al., *Arthritis & Rheum.* 2005, 52, 1907-1919) and the mouse CIA (Plater-Zyberk, C. et al., *Imm. Lett.* 1997, 57, 117-120) disease models of joint inflammation.

Recently, a number of groups have described the development of small molecule antagonists of MIP-1α (reviewed in: Carson, K. G. et al., *Ann. Reports Med. Chem.* 2004, 39, 149-158).

SUMMARY OF THE INVENTION

Accordingly, the present invention provides novel antagonists or partial agonists/antagonists of MIP-1α or CCR-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis and transplant rejection, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases.

These and other features of the invention, which will become apparent during the following detailed description, have been achieved by the inventors' discovery that compounds of formula (I):

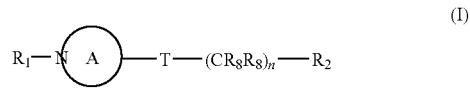

(I)

or stereoisomers or prodrugs or pharmaceutically acceptable salts thereof, wherein A, n, T, $R_1$, $R_2$ and $R_8$, are defined below, are effective modulators of MIP-1α and chemokine activity.

DETAILED DESCRIPTION OF THE PRESENT INVENTION

In one embodiment, the present invention provides novel compounds of formula (I):

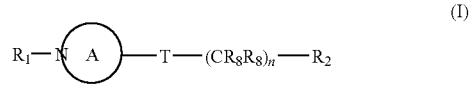

(I)

or stereoisomers or pharmaceutically acceptable salt forms thereof, wherein:

Ring A is

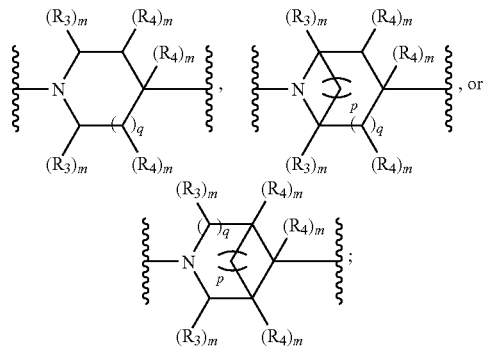

T is a bond,

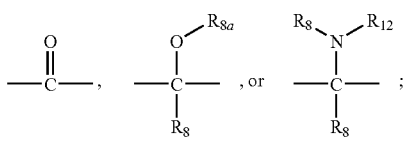

$R_1$ is aryl, which may be optionally substituted with one or more $R_{1a}$;

$R_{1a}$, at each occurrence, is independently selected from alkyl, haloalkyl, alkynyl, halo, —CN, —O(CF$_2$)$_r$CF$_3$, —O(CR$_8$R$_8$)$_r$R$_{10}$, —OH or —S(CR$_8$R$_8$)$_r$R$_{10}$;

$R_2$ is aryl, heteroaryl or heterocyclyl, all of which may be optionally substituted with one or more $R_{2a}$;

$R_{2a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —NR$_9$C(=O)NR$_9$R$_9$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, =O, —S(O)$_2$NR$_9$C(=O)R$_6$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{2b}$;

$R_{2b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{10}$, —O$(CF_2)_rCF_3$, —O$(CR_8R_8)_rR_{10}$, —OH, —SH, —S$(CR_8R_8)_rR_{10}$, —S(O)$_3$H, —F(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —NR$_9$C(=O)NR$_9$R$_9$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, aryloxy or arylalkyl;

$R_3$, at each occurrence, is alkyl; or any two $R_3$'s attached to the same carbon atom may form a 3- to 5-membered ring;

$R_4$, at each occurrence, is F, alkyl, —OR$_9$ or —NR$_9$R$_9$; or any two alkyl $R_4$'s attached to the same carbon atom may form a 3- to 5-membered ring;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_{8a}$, at each occurrence, is independently hydrogen, alkyl or —C(=O)(CR$_8$R$_8$)$_r$R$_{15}$; or $R_{8a}$ may be taken together with the carbon atom to which it is attached to form a 3- to 6-membered ring wherein the carbon atoms of said ring may be optionally replaced with a heteroatom selected from N, O, and S;

$R_9$, at each occurrence, is independently hydrogen, alkyl, cycloalkyl, aryl, arylalkyl, heteroaryl, heteroarylalkyl, heterocyclyl or heterocyclylalkyl, wherein the alkyl, cycloalkyl, aryl, arylalkyl, heteroaryl, heteroarylalkyl, heterocyclyl or heterocyclylalkyl may be optionally substituted with one or more $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

$R_{10}$, at each occurrence, is independently selected from alkyl, cycloalkyl, alkenyl, alkynyl, aryl, arylalkyl, heterocyclyl or heterocyclylalkyl, wherein the alkyl, cycloalkyl, aryl, arylalkyl, heterocyclyl or heterocyclylalkyl may be optionally substituted with one or more $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

$R_{12}$ is hydrogen, alkyl, cycloalkyl, aryl, arylalkyl, heteroaryl, heteroarylalkyl, heterocyclyl, —S(O)$_2$R$_{15}$, —C(=O)R$_{15}$, —C(=O)NH$_2$, —C(=O)NR$_8$R$_{15}$, —C(=O)OR$_{15}$ or heterocyclylalkyl, wherein the alkyl, cycloalkyl, aryl, arylalkyl, heteroaryl, heteroarylalkyl, heterocyclyl or heterocyclylalkyl may be optionally substituted with one or more $R_{12a}$, and the heteroaryl, heteroarylalkyl, heterocyclyl or heterocyclylalkyl contain 1-4 heteroatoms selected from N, O, and S;

$R_{12a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_rCF_3$, —O$(CR_8R_8)_rR_{14}$, —OH, —SH, —S$(CR_8R_8)_rR_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

m, at each occurrence, is independently 0-2;
n is 1-3;
p is 1 or 2;
q is 0-2; and
r, at each occurrence, is independently 0-5.

In another embodiment, compounds of the present invention, or a stereoisomer or pharmaceutically acceptable salt from thereof, are those in which $R_1$ is aryl, which may be optionally substituted with one or more $R_{1a}$.

In another embodiment, compounds of the present invention, or a stereoisomer or pharmaceutically acceptable salt from thereof, are those in which the compound is a compound of formula (Ia):

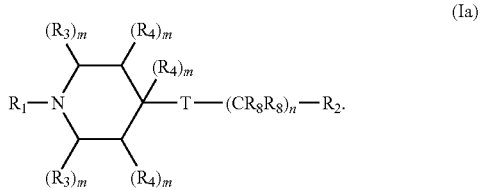

(Ia)

In another embodiment, compounds of the present invention, or a stereoisomer or pharmaceutically acceptable salt from thereof, are those in which the compound is a compound of formula (Ib):

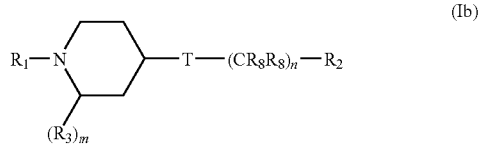

(Ib)

in which $R_1$ is phenyl optionally substituted with one or more $R_{1a}$.

In yet another embodiment, compounds of the present invention, or a stereoisomer or pharmaceutically acceptable salt from thereof, are those in which:

Ring A is

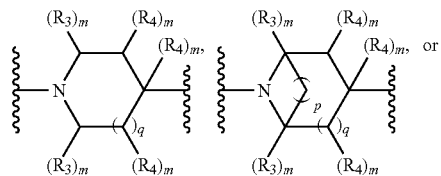

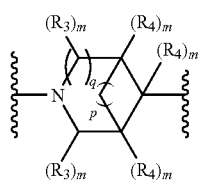

T is

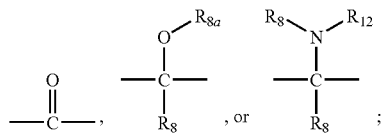

$R_1$ is aryl, which may be optionally substituted with one or more $R_{1a}$;

$R_{1a}$, at each occurrence, is independently selected from alkyl, haloalkyl, halo, —CN, —O(CF$_2$)$_r$CF$_3$, —O(CR$_8$R$_8$)$_r$R$_{10}$, —OH or —S(CR$_8$R$_8$)$_r$R$_{10}$;

$R_2$ is aryl, heteroaryl or heterocyclyl, all of which may be optionally substituted with one or more $R_{2a}$;

$R_{2a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —NR$_9$C(=O)NR$_9$R$_9$, =O, —S(O)$_2$NR$_9$C(=O)R$_6$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{2b}$;

$R_{2b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —NR$_9$C(=O)NR$_9$R$_9$, aryloxy or arylalkyl;

$R_3$, at each occurrence, is alkyl; or any two $R_3$'s attached to the same carbon atom may form a 3- to 5-membered ring;

$R_4$, at each occurrence, is F, alkyl, —OR$_9$ or —NR$_9$R$_9$; or any two alkyl $R_4$'s attached to the same carbon atom may form a 3- to 5-membered ring;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_{8a}$, at each occurrence, is independently hydrogen, alkyl or —C(=O)(CR$_8$R$_8$)$_r$R$_{15}$;

$R_9$, at each occurrence, is independently hydrogen, alkyl, cycloalkyl, aryl, arylalkyl, heteroaryl, heteroarylalkyl or heterocyclyl, wherein the alkyl, cycloalkyl, aryl, arylalkyl, heteroaryl, heteroarylalkyl or heterocyclyl may be optionally substituted with one or more $R_{9a}$, and the heteroaryl, heteroarylalkyl, or heterocyclyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$ $(CF_2)_rCF_3$, $—C(=O)(CR_8R_8)_rR_{14}$, $—NR_{14}C(=O)H$, $—NR_{14}C(=O)(CR_8R_8)_rR_{14}$, aryloxy or arylalkyl;

$R_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with one or more $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $—NH_2$, $—CN$, $—NO_2$, $—C(=O)OH$, $—C(=O)O(CR_8R_8)_rR_{14}$, $—O(CF_2)_rCF_3$, $—O(CR_8R_8)_rR_{14}$, $—OH$, $—SH$, $—S(CR_8R_8)_rR_{14}$, $—S(O)_3H$, $—P(O)_3H_2$, $—C(=O)NR_{14}R_{14}$, $—NR_{14}R_{14}$, $—S(O)_2NR_{14}R_{14}$, $—NR_{14}S(O)_2(CF_2)_rCF_3$, $—C(=O)NR_{14}S(O)_2R_6$, $—S(O)_2NR_{14}C(=O)OR_6$, $—S(O)_2NR_{14}C(=O)NR_{14}R_{14}$, $—C(=O)NR_{14}S(O)_2(CF_2)_rCF_3$, $—C(=O)(CR_8R_8)_rR_{14}$, $—NR_{14}C(=O)H$, $—NR_{14}C(=O)(CR_8R_8)_rR_{14}$, aryloxy or arylalkyl;

$R_{12}$ is hydrogen, alkyl, cycloalkyl, aryl, arylalkyl, heteroaryl, heteroarylalkyl, heterocyclyl, $—S(O)_2R_{15}$, $—C(=O)R_{15}$, $—C(=O)NH_2$, $—C(=O)NR_8R_{15}$, or $—C(=O)OR_{15}$, wherein the alkyl, cycloalkyl, aryl, arylalkyl, heteroaryl, heteroarylalkyl or heterocyclyl may be optionally substituted with one or more $R_{12a}$, and the heteroaryl, heteroarylalkyl or heterocyclyl contain 1-4 heteroatoms selected from N, O, and S;

$R_{12a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $—NH_2$, $—CN$, $—NO_2$, $—C(=O)OH$, $—C(=O)O(CR_8R_8)_rR_{14}$, $—O(CF_2)_rCF_3$, $—O(CR_8R_8)_rR_{14}$, $—OH$, $—SH$, $—S(CR_8R_8)_rR_{14}$, $—S(O)_3H$, $—P(O)_3H_2$, $—C(=O)NR_{14}R_{14}$, $—NR_{14}R_{14}$, $—S(O)_2NR_{14}R_{14}$, $—NR_{14}S(O)_2(CF_2)_rCF_3$, $—C(=O)NR_{14}S(O)_2R_6$, $—S(O)_2NR_{14}C(=O)OR_6$, $—S(O)_2NR_{14}C(=O)NR_{14}R_{14}$, $—C(=O)NR_{14}S(O)_2(CF_2)_rCF_3$, $—C(=O)(CR_8R_8)_rR_{14}$, $—NR_{14}C(=O)H$, $—NR_{14}C(=O)(CR_8R_8)_rR_{14}$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $—NH_2$, $—CN$, $—NO_2$, $—C(=O)OH$, $—C(=O)O(CR_8R_8)_rR_{14}$, $—O(CF_2)_rCF_3$, $—O(CR_8R_8)_rR_{14}$, $—OH$, $—SH$, $—S(CR_8R_8)_rR_{14}$, $—S(O)_3H$, $—P(O)_3H_{12}$, $—C(=O)NR_{14}R_{14}$, $—NR_{14}R_{14}$, $—S(O)_2NR_{14}R_{14}$, $—NR_{14}S(O)_2(CF_2)_rCF_3$, $—C(=O)NR_{14}S(O)_2R_6$, $—S(O)_2NR_{14}C(=O)OR_6$, $—S(O)_2NR_{14}C(=O)NR_{14}R_{14}$, $—C(=O)NR_{14}S(O)_2(CF_2)_rCF_3$, $—C(=O)(CR_8R_8)_rR_{14}$, $—NR_{14}C(=O)H$, $—NR_{14}C(=O)(CR_8R_8)_rR_{14}$, aryloxy or arylalkyl;

m, at each occurrence, is independently 0-2;

n is 1-3;

p is 1 or 2;

q is 0-2; and r, at each occurrence, is independently 0-5.

In still yet another embodiment, compounds of the present invention, or a stereoisomer or pharmaceutically acceptable salt from thereof, are those in which:

Ring A is

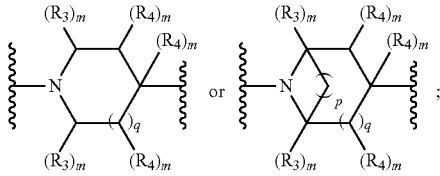

T is

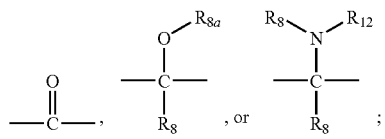

$R_1$ is aryl, which may be optionally substituted with one or more $R_{1a}$;

$R_{1a}$, at each occurrence, is independently selected from alkyl, haloalkyl, halo, $—CN$, $—O(CF_2)_rCF_3$, $—O(CR_8R_8)_rR_{10}$ or $—OH$;

$R_2$ is heteroaryl or heterocyclyl, both of which may be optionally substituted with one or more $R_{2a}$;

$R_{2a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $—NH_2$, $—CN$, $—NO_2$, $—C(=O)OH$, $—C(=O)O(CR_8R_8)_rR_{10}$, $—O(CF_2)_rCF_3$, $—O(CR_8R_8)_rR_{10}$, $—OH$, $—SH$, $—S(CR_8R_8)_rR_{10}$, $—S(O)_3H$, $—P(O)_3H_2$, $—C(=O)NR_9R_9$, $—NR_9R_9$, $—S(O)_2NR_9R_9$, $—NR_9S(O)_2(CF_2)_rCF_3$, $—C(=O)NR_9S(O)_2R_6$, $—S(O)_2NR_9C(=O)OR_6$, $—S(O)_2NR_9C(=O)NR_9R_9$, $—C(=O)NR_9S(O)_2(CF_2)_rCF_3$, $=O$, $—S(O)_2NR_9C(=O)R_6$, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{2b}$;

$R_{2b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $—NH_2$, $—CN$, $—NO_2$, $—C(=O)OH$, $—C(=O)O(CR_8R_8)_rR_{10}$, $—O(CF_2)_rCF_3$, $—O(CR_8R_8)_rR_{10}$, $—OH$, $—SH$, $—S(CR_8R_8)_rR_{10}$, $—S(O)_3H$, $—P(O)_3H_2$, $—C(=O)NR_9R_9$, $—NR_9R_9$, $—S(O)_2NR_9R_9$, $—NR_9S(O)_2(CF_2)_rCF_3$, $—C(=O)NR_9S(O)_2R_6$, $—S(O)_2NR_9C(=O)OR_6$, $—S(O)_2NR_9C(=O)NR_9R_9$, $—C(=O)NR_9S(O)_2(CF_2)_rCF_3$, aryloxy or arylalkyl;

$R_3$, at each occurrence, is alkyl; or any two $R_3$'s attached to the same carbon atom may form a 3- to 5-membered ring;

$R_4$, at each occurrence, is F, alkyl, $—OR_9$ or $—NR_9R_9$; or any two alkyl $R_4$'s attached to the same carbon atom may form a 3- to 5-membered ring;

$R_6$, at each occurrence, is independently alkyl, cycloalkyl, cycloalkylalkyl, aryl, arylalkyl or heteroaryl;

$R_8$, at each occurrence, is independently hydrogen or alkyl;

$R_{8a}$, at each occurrence, is independently hydrogen, alkyl or $—C(=O)(CR_8R_8)_rR_{15}$;

$R_9$, at each occurrence, is independently hydrogen, alkyl, cycloalkyl, aryl, arylalkyl, heteroaryl or heterocyclyl, wherein the alkyl, cycloalkyl, aryl, arylalkyl, heteroaryl or heterocyclyl may be optionally substituted with one or more $R_{9a}$, and the heteroaryl or heterocyclyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, aryloxy or arylalkyl;

$R_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with one or more $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, aryloxy or arylalkyl;

$R_{12}$ is hydrogen, alkyl, cycloalkyl, aryl, arylalkyl, heteroaryl, heterocyclyl, —S(O)$_2$R$_{15}$, —C(=O)R$_{15}$, —C(=O)NH$_2$, —C(=O)NR$_8$R$_{15}$, or —C(=O)OR$_{15}$, wherein the alkyl, cycloalkyl, aryl, arylalkyl, heteroaryl or heterocyclyl may be optionally substituted with one or more $R_{12a}$, and the heteroaryl or heterocyclyl contain 1-4 heteroatoms selected from N, O, and S;

$R_{12a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, aryloxy or arylalkyl;

m, at each occurrence, is independently 0-2;

n is 1-3;

p is 1 or 2;

q is 0-2; and r, at each occurrence, is independently 0-4.

In one embodiment, compounds of the present invention, or a stereoisomer or pharmaceutically acceptable salt from thereof, are those in which:

Ring A is

T is $R_1$ is aryl, which may be optionally substituted with one or more $R_{1a}$;

$R_{1a}$, at each occurrence, is independently selected from alkyl, haloalkyl, halo, —CN, —O(CR$_8$R$_8$)$_r$R$_{10}$ or —OH;

$R_2$ is a nitrogen containing heteroaryl or heterocyclyl, both of which may be optionally substituted with one or more $R_{2a}$;

$R_{2a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, =O, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{2b}$;

$R_{2b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, aryloxy or arylalkyl;

$R_3$, at each occurrence, is alkyl; or any two $R_3$'s attached to the same carbon atom may form a 3- to 5-membered ring;

$R_4$, at each occurrence, is F, alkyl, —OR$_9$ or —NR$_9$R$_9$; or any two alkyl $R_4$'s attached to the same carbon atom may form a 3- to 5-membered ring;

$R_6$, at each occurrence, is independently alkyl, cycloalkyl, aryl, arylalkyl or heteroaryl;

$R_8$, at each occurrence, is independently hydrogen or alkyl;

$R_{8a}$, at each occurrence, is independently hydrogen, alkyl or —C(=O)(CR$_8$R$_8$)$_r$R$_{15}$;

$R_9$, at each occurrence, is independently hydrogen, alkyl, cycloalkyl, aryl, heteroaryl or heterocyclyl, wherein the alkyl, cycloalkyl, aryl, heteroaryl or heterocyclyl may be optionally substituted with one or more $R_{9a}$, and the heteroaryl or heterocyclyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$$H_2$, —C(=O)$NR_{14}R_{14}$, —$NR_{14}R_{14}$, —S(O)$_2$$NR_{14}R_{14}$, aryloxy or arylalkyl;

$R_{10}$, at each occurrence, is independently selected from alkyl, cycloalkyl, alkenyl, aryl, arylalkyl or heterocyclyl, wherein the alkyl, cycloalkyl, aryl, arylalkyl or heterocyclyl may be optionally substituted with one or more $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$$H_2$, —C(=O)$NR_{14}R_{14}$, —$NR_{14}R_{14}$, —S(O)$_2$$NR_{14}R_{14}$, —$NR_{14}S(O)_2$($CF_2$)$_r$$CF_3$, aryloxy or arylalkyl;

$R_{12}$ is hydrogen, alkyl, cycloalkyl, aryl, heteroaryl, heterocyclyl, —S(O)$_2$$R_{15}$, —C(=O)$R_{15}$, —C(=O)$NH_2$, —C(=O)$NR_8R_{15}$, or —C(=O)$OR_{15}$, wherein the alkyl, cycloalkyl, aryl, heteroaryl or heterocyclyl may be optionally substituted with one or more $R_{12a}$, and the heteroaryl or heterocyclyl contain 1-4 heteroatoms selected from N, O, and S;

$R_{12a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$$H_2$, —C(=O)$NR_{14}R_{14}$, —$NR_{14}R_{14}$, —S(O)$_2$$NR_{14}R_{14}$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$$H_2$, —C(=O)$NR_{14}R_{14}$, —$NR_{14}R_{14}$, —S(O)$_2$$NR_{14}R_{14}$, aryloxy or arylalkyl;

m, at each occurrence, is independently 0-2;
n is 1-2;
p is 1 or 2;
q is 0-2; and
r, at each occurrence, is independently 0-3.

In another embodiment, compounds of the present invention, or a stereoisomer or pharmaceutically acceptable salt from thereof, are those in which:

Ring A is

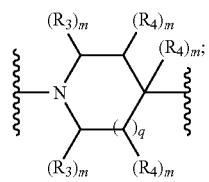

T is

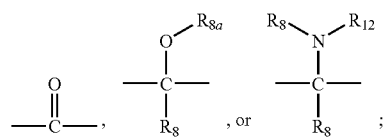

$R_1$ is aryl, which may be optionally substituted with one or more $R_{1a}$;

$R_{1a}$, at each occurrence, is independently selected from alkyl, halo, —CN, —O($CR_8R_8$)$_r$$R_{10}$ or —OH;

$R_2$ is a 5- to 10-membered nitrogen containing heteroaryl or heterocyclyl, both of which may be optionally substituted with one or more $R_{2a}$;

$R_{2a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$$H_2$, —C(=O)$NR_9R_9$, —$NR_9R_9$, =O, aryloxy or arylalkyl, wherein the alkyl, aryl, arylalkyl, cycloalkylalkyl, heteroaryl, heteroarylalkyl, heterocyclyl heterocyclylalkyl, aryloxy and arylalkyl may be optionally substituted with one or more $R_{2b}$;

$R_{2b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$$H_2$, —C(=O)$NR_9R_9$, —$NR_9R_9$, aryloxy or arylalkyl;

$R_3$, at each occurrence, is alkyl; or any two $R_3$'s attached to the same carbon atom may form a 3- to 5-membered ring;

$R_4$, at each occurrence, is F, alkyl, —$OR_9$ or —$NR_9R_9$;

$R_8$, at each occurrence, is independently hydrogen or alkyl;

$R_{8a}$, at each occurrence, is independently hydrogen, alkyl or —C(=O)($CR_8R_8$)$_r$$R_{15}$;

$R_9$, at each occurrence, is independently hydrogen, alkyl, cycloalkyl, aryl or heteroaryl, wherein the alkyl, cycloalkyl, aryl or heteroaryl may be optionally substituted with one or more $R_{9a}$, and the heteroaryl contains 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$$H_2$, —C(=O)$NR_{14}R_{14}$, —$NR_{14}R_{14}$, aryloxy or arylalkyl;

$R_{10}$, at each occurrence, is independently selected from alkyl, cycloalkyl, aryl, arylalkyl or heterocyclyl, wherein the alkyl, cycloalkyl, aryl, arylalkyl or heterocyclyl may be optionally substituted with one or more $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$$H_2$, —C(=O)$NR_{14}R_{14}$, —$NR_{14}R_{14}$ aryloxy or arylalkyl;

$R_{12}$ is hydrogen, alkyl, cycloalkyl, aryl, heteroaryl, —S(O)$_2$ $R_{15}$, —C(=O)$R_{15}$, —C(=O)$NH_2$, —C(=O)$NR_8R_{15}$, or —C(=O)$OR_{15}$, wherein the alkyl, cycloalkyl, aryl, or heteroaryl may be optionally substituted with one or more $R_{12a}$, and the heteroaryl contains 1-4 heteroatoms selected from N, O, and S;

$R_{12a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, aryloxy or arylalkyl;

m, at each occurrence, is independently 0-2;
n is 1-2;
q is 0-2; and
r, at each occurrence, is independently 0-2.

In yet another embodiment, compounds of the present invention, or a stereoisomer or pharmaceutically acceptable salt from thereof, are those in which:

Ring A is

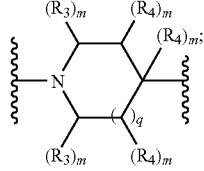

T is

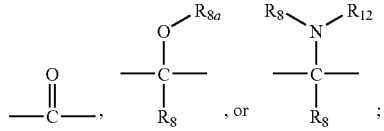

$R_1$ is aryl, which may be optionally substituted with one or more $R_{1a}$;

$R_{1a}$, at each occurrence, is independently selected from alkyl, halo, —CN or —O(CR$_8$R$_8$)$_r$R$_{10}$;

$R_2$ is a 5- to 8-membered nitrogen containing heteroaryl or heterocyclyl, both of which may be optionally substituted with one or more $R_{2a}$;

$R_{2a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{10}$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, =O, aryloxy or arylalkyl, wherein the alkyl, aryl, cycloalkyl, cycloalkylalkyl, heteroaryl, heteroarylalkyl, heterocyclyl heterocyclylalkyl, aryloxy and arylalkyl may be optionally substituted with one or more $R_{2b}$;

$R_{2b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$, aryloxy or arylalkyl;

$R_3$, at each occurrence, is alkyl;
$R_4$, at each occurrence, is F, alkyl, —OR$_9$ or NR$_9$R$_9$;
$R_8$, at each occurrence, is independently hydrogen or alkyl;
$R_{8a}$, at each occurrence, is independently hydrogen, alkyl or —C(=O)(CR$_8$R$_8$)$_r$R$_{15}$;

$R_9$, at each occurrence, is independently hydrogen, alkyl, aryl or heteroaryl, wherein the alkyl, aryl or heteroaryl may be optionally substituted with one or more $R_{9a}$, and the heteroaryl contains 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, aryloxy or arylalkyl;

$R_{10}$, at each occurrence, is independently selected from alkyl, cycloalkyl, aryl or heterocyclyl, wherein the alkyl, cycloalkyl, aryl or heterocyclyl may be optionally substituted with one or more $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, aryloxy or arylalkyl;

$R_{12}$ is hydrogen, alkyl, aryl, heteroaryl, —S(O)$_2$R$_{15}$, —C(=O)R$_{15}$, —C(=O)NH$_2$, —C(=O)NR$_8$R$_{15}$, or —C(=O)OR$_{15}$, wherein the alkyl, aryl or heteroaryl may be optionally substituted with one or more $R_{12a}$, and the heteroaryl contains 1-4 heteroatoms selected from N, O, and S;

$R_{12a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, aryloxy or arylalkyl;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —C(=O)NR$_{14}$R$_{14}$, —NR$_{14}$R$_{14}$, aryloxy or arylalkyl;

m, at each occurrence, is independently 0-2;
n is 1-2;
q is 0-2; and
r, at each occurrence, is independently 0-2.

In still yet another embodiment, compounds of the present invention, or a stereoisomer or pharmaceutically acceptable salt from thereof, are those in which:

Ring A is

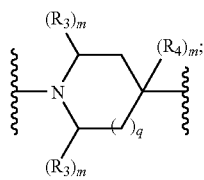

T is

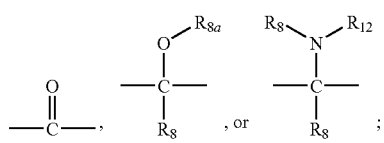

$R_1$ is aryl, which may be optionally substituted with one or more $R_{1a}$;

$R_{1a}$, at each occurrence, is independently selected from alkyl, halo, —CN or —O$(CR_8R_8)_rR_{10}$;

$R_2$ is a 5- to 8-membered nitrogen containing heteroaryl or heterocyclyl, both of which may be optionally substituted with one or more $R_{2a}$ and wherein the 5- to 8-membered nitrogen containing heteroaryl or heterocyclyl is attached via a nitrogen heteroatom;

$R_{2a}$, at each occurrence, is independently selected from alkyl, haloalkyl, aryl, alkenyl, alkynyl, cycloalkyl, heteroaryl, heterocyclyl, halo, —NH$_2$, —CN, —NO$_2$, —C(=O)OH, —C(=O)O$(CR_8R_8)_rR_{10}$, —O$(CR_8R_8)_rR_{10}$, —OH, —SH, —S$(CR_8R_8)_rR_{10}$, —C(=O)NR$_9$R$_9$, —NR$_9$R$_9$, =O or aryloxy, wherein the alkyl, aryl, cycloalkyl, heteroaryl, heterocyclyl and aryloxy may be optionally substituted with one or more $R_{2b}$;

$R_{2b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O$(CR_8R_8)_rR_{10}$, —O$(CR_8R_8)_rR_{10}$, —OH, —SH, —NR$_9$R$_9$, aryloxy or arylalkyl;

$R_3$, at each occurrence, is alkyl;

$R_4$, at each occurrence, is F, alkyl, —OR$_9$ or NR$_9$R$_9$;

$R_8$, at each occurrence, is independently hydrogen or alkyl;

$R_{8a}$, at each occurrence, is independently hydrogen, alkyl or —C(=O)$(CR_8R_8)_rR_{15}$;

$R_9$, at each occurrence, is independently hydrogen, alkyl or aryl, wherein the alkyl or aryl may be optionally substituted with one or more $R_{9a}$;

$R_{9a}$, at each occurrence, is independently selected from alkyl, haloalkyl, aryl, alkenyl, alkynyl, cycloalkyl, heteroaryl, heterocyclyl, halo, —NH$_2$, —CN, —NO$_2$, —C(=O)OH, —C(=O)O$(CR_8R_8)_rR_{14}$, —O(CF$_2$)$_r$CF$_3$, —O$(CR_8R_8)_rR_{14}$, —OH, —SH, —S$(CR_8R_8)_rR_{14}$, —C(=O)NR$_{14}$R$_{14}$, —NR$_{14}$R$_{14}$ or aryloxy;

$R_{10}$, at each occurrence, is independently selected from alkyl, aryl or heterocyclyl, wherein the alkyl, aryl or heterocyclyl may be optionally substituted with one or more $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, heteroaryl, heterocyclyl, halo, —NH$_2$, —CN, —NO$_2$, —C(=O)OH, —C(=O)O$(CR_8R_8)_rR_{14}$, —O(CF$_2$)$_r$CF$_3$, —O$(CR_8R_8)_rR_{14}$, —OH, —SH, —S$(CR_8R_8)_rR_{14}$, —C(=O)NR$_{14}$R$_{14}$, —NR$_{14}$R$_{14}$ or aryloxy;

$R_{12}$ is hydrogen, alkyl, heteroaryl, —S(O)$_2$R$_{15}$, —C(=O)R$_{15}$, —C(=O)NH$_2$, —C(=O)NR$_8$R$_{15}$, or —C(=O)OR$_{15}$, wherein the alkyl or heteroaryl may be optionally substituted with one or more $R_{12a}$, and the heteroaryl contains 1-4 heteroatoms selected from N, O, and S;

$R_{12a}$, at each occurrence, is independently selected from alkyl, haloalkyl, aryl, alkenyl, alkynyl, cycloalkyl, heteroaryl, heterocyclyl, halo, —NH$_2$, —CN, —NO$_2$, —C(=O)OH, —C(=O)O$(CR_8R_8)_rR_{14}$, —O(CF$_2$)$_r$CF$_3$, —O$(CR_8R_8)_rR_{14}$, —OH, —SH, —S$(CR_8R_8)_rR_{14}$, —C(=O)NR$_{14}$R$_{14}$, —NR$_{14}$R$_{14}$ or aryloxy;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, alkenyl, alkynyl, cycloalkyl, heteroaryl, heterocyclyl, halo, —NH$_2$, —CN, —NO$_2$, —C(=O)OH, —C(=O)O$(CR_8R_8)_rR_{14}$, —O(CF$_2$)$_r$CF$_3$, —O$(CR_8R_8)_rR_{14}$, —OH, —SH, —S$(CR_8R_8)_rR_{14}$, —C(=O)NR$_{14}$R$_{14}$, —NR$_{14}$R$_{14}$ or aryloxy;

m, at each occurrence, is independently 0-2;

n is 1-2;

q is 1 or 2; and r, at each occurrence, is independently 0-2.

In one embodiment, compounds of the present invention, or a stereoisomer or pharmaceutically acceptable salt from thereof, are those in which:

Ring A is

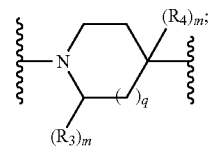

T is

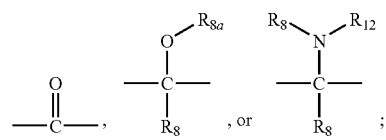

$R_1$ is aryl, which may be optionally substituted with one or more $R_{1a}$;

$R_{1a}$, at each occurrence, is independently selected from halo, —CN, or —O$(CR_8R_8)_rR_{10}$;

$R_2$ is a 5- to 8-membered nitrogen containing heteroaryl or heterocyclyl, both of which may be optionally substituted with one or more $R_{2a}$ and wherein the 5- to 8-membered nitrogen containing heteroaryl or heterocyclyl is attached via a nitrogen heteroatom;

$R_{2a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O$(CR_8R_8)_rR_{10}$, —O$(CR_8R_8)_rR_{10}$, —OH, —SH, —S$(CR_8R_8)_rR_{10}$, —C(=O)NR$_9$R$_9$, —NR$_9$R$_9$ or =O, wherein the alkyl, aryl, cycloalkyl, heteroaryl, heterocyclyl and aryloxy may be optionally substituted with one or more $R_{2b}$;

$R_{2b}$, at each occurrence, is independently selected from alkyl, haloalkyl, aryl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CR_8R_8$)$_r$$R_{10}$, —OH, —SH, or —$NR_9R_9$;

$R_3$ is alkyl;

$R_4$, at each occurrence, is F, alkyl or —$OR_9$;

$R_8$, at each occurrence, is independently hydrogen or alkyl;

$R_{8a}$, at each occurrence, is independently hydrogen, alkyl or —C(=O)($CR_8R_8$)$_r$$R_{15}$;

$R_9$, at each occurrence, is independently hydrogen, alkyl or aryl, wherein the alkyl or aryl may be optionally substituted with one or more $R_{9a}$;

$R_{9a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —C(=O)$NR_{14}R_{14}$ or —$NR_{14}R_{14}$;

$R_{10}$, at each occurrence, is independently selected from alkyl or aryl, wherein the alkyl or aryl may be optionally substituted with one or more $R_{10a}$;

$R_{10a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$; —C(=O)$NR_{14}R_{14}$ or —$NR_{14}R_{14}$;

$R_{12}$ is hydrogen, alkyl, heteroaryl, —S(O)$_2$$R_{15}$, —C(=O)$R_{15}$, —C(=O)$NH_2$; —C(=O)$NR_8R_{15}$, or —C(=O)$OR_{15}$, wherein the alkyl or heteroaryl may be optionally substituted with one or more $R_{12a}$, and the heteroaryl contains 1-4 heteroatoms selected from N, O, and S;

$R_{12a}$; at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$; —C(=O)$NR_{14}R_{14}$ or —$NR_{14}R_{14}$;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —C(=O)$NR_{14}R_{14}$ or —$NR_{14}R_{14}$;

m, at each occurrence, is independently 0-2;

n is 1-2;

q is 1 or 2; and r, at each occurrence, is independently 0-2.

In another embodiment, compounds of the present invention, or a stereoisomer or pharmaceutically acceptable salt from thereof, are those in which:

Ring A is

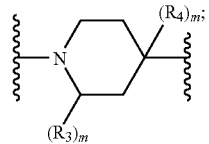

T is

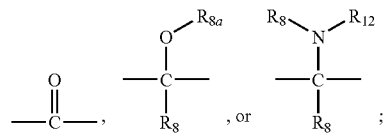

$R_1$ is phenyl, which may be optionally substituted with one or more $R_{1a}$;

$R_{1a}$, at each occurrence, is independently selected from halo, —CN or —O($CR_8R_8$)$_r$$R_{10}$;

$R_2$ is a 5- to 8-membered nitrogen containing heteroaryl or heterocyclyl, both of which may be optionally substituted with one or more $R_{2a}$ and wherein the 5- to 8-membered nitrogen containing heteroaryl or heterocyclyl is attached via a nitrogen heteroatom;

$R_{2a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{10}$, —O($CR_8R_8$)$_r$$R_{10}$, —OH, —C(=O)$NR_9R_9$, —$NR_9R_9$ or =O, wherein the alkyl, aryl, cycloalkyl, heteroaryl, heterocyclyl and aryloxy may be optionally substituted with one or more $R_{2b}$;

$R_{2b}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{10}$, —O($CR_8R_8$)$_r$$R_{10}$, —OH, —SH, or —$NR_9R_9$;

$R_3$ is alkyl;

$R_4$, at each occurrence, is alkyl or —$OR_9$;

$R_8$, at each occurrence, is independently hydrogen or alkyl;

$R_{8a}$, at each occurrence, is independently hydrogen, alkyl or —C(=O)($CR_8R_8$)$_r$$R_{15}$;

$R_9$, at each occurrence, is independently hydrogen, alkyl or aryl, wherein the alkyl or aryl may be optionally substituted with one or more $R_{9a}$;

$R_{9a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —C(=O)$NR_{14}R_{14}$ or —$NR_{14}R_{14}$;

$R_{10}$, at each occurrence, is independently selected from alkyl or aryl, wherein the alkyl or aryl may be optionally substituted with one or more $R_{10a}$;

$R_{10a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —C(=O)$NR_{14}R_{14}$ or —$NR_{14}R_{14}$;

$R_{12}$ is alkyl, heteroaryl, —S(O)$_2$$R_{15}$, —C(=O)$R_{15}$, —C(=O)$NH_2$, —C(=O)$NR_8R_{15}$, or —C(=O)$OR_{15}$, wherein the alkyl or heteroaryl may be optionally substituted with one or more $R_{12a}$, and the heteroaryl contains 1-4 heteroatoms selected from N, O, and S;

$R_{12a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —C(=O)$NR_{14}R_{14}$ or —$NR_{14}R_{14}$;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O$(CR_8R_8)_rR_{14}$, —$O(CF_2)_rCF_3$, —$O(CR_8R_8)_rR_{14}$, —OH, —C(=O)$NR_{14}R_{14}$ or —$NR_{14}R_{14}$;

m, at each occurrence, is independently 0-2;

n is 1-2; and r, at each occurrence, is independently 0-2.

In another embodiment, compounds of the present invention, or a stereoisomer or pharmaceutically acceptable salt from thereof, are those in which:

Ring A is

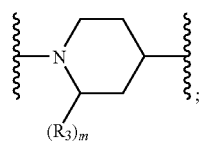

T is

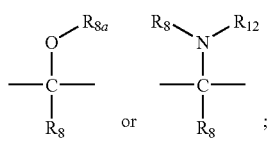

$R_1$ is phenyl, which may be optionally substituted with one or more $R_{1a}$;

$R_{1a}$, at each occurrence, is independently selected from halo, —CN or —$O(CR_8R_8)_rR_{10}$;

$R_2$ is a 5- to 8-membered nitrogen containing heteroaryl or heterocyclyl, both of which may be optionally substituted with one or more $R_{2a}$ and wherein the 5- to 8-membered nitrogen containing heteroaryl or heterocyclyl is attached via a nitrogen heteroatom;

$R_{2a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O$(CR_8R_8)_rR_{10}$, —$O(CR_8R_8)_rR_{10}$, —OH or =O, wherein the alkyl, aryl, cycloalkyl, heteroaryl, heterocyclyl and aryloxy may be optionally substituted with one or more $R_{2b}$;

$R_{2b}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O$(CR_8R_8)_rR_{10}$, —$O(CR_8R_8)_rR_{10}$, or —OH;

$R_3$ is alkyl;

$R_8$, at each occurrence, is independently hydrogen or alkyl;

$R_{8a}$, at each occurrence, is independently hydrogen, alkyl or —C(=O)$(CR_8R_8)_rR_{15}$;

$R_{10}$, at each occurrence, is independently selected from alkyl or aryl, wherein the alkyl or aryl may be optionally substituted with one or more $R_{10a}$;

$R_{10a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O$(CR_8R_8)_rR_{14}$, —$O(CR_8R_8)_rR_{14}$, —OH, —C(=O)$NR_{14}R_{14}$ or —$NR_{14}R_{14}$;

$R_{12}$ is alkyl, heteroaryl, —$S(O)_2R_{15}$, —C(=O)$R_{15}$, —C(=O)$NH_2$, —C(=O)$NR_8R_{15}$, or —C(=O)$OR_{15}$, wherein the alkyl or heteroaryl may be optionally substituted with one or more $R_{12a}$, and the heteroaryl contains 1-4 heteroatoms selected from N, O, and S;

$R_{12a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O$(CR_8R_8)_rR_{14}$, —$O(CR_8R_8)_rR_{14}$, —OH, —C(=O)$NR_{14}R_{14}$ or —$NR_{14}R_{14}$;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O$(CR_8R_8)_rR_{14}$, —$O(CR_8R_8)_rR_{14}$, —OH, or —$NR_{14}R_{14}$;

m, at each occurrence, is independently 0-2;

n is 1-2; and r, at each occurrence, is independently 0 or 1.

In one embodiment, compounds of the present invention, or a stereoisomer or pharmaceutically acceptable salt from thereof, are those in which:

Ring A is

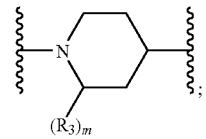

T is

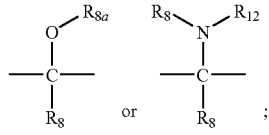

$R_1$ is phenyl, which may be optionally substituted with one or more $R_{1a}$;

$R_{1a}$, at each occurrence, is independently selected from halo, —CN or —$O(CR_8R_8)_rR_{10}$;

$R_2$ is pyrazolyl, imidazolyl, indolyl, tetrazolyl, triazolyl, benzoimidazolyl, pyridinyl, imidazopyridinyl, dihydro-benzoimidazolyl, pyrazolopyridinyl, pyridinonyl, pyrimidinonylor pyrimidinyl, all of which may be optionally substituted with one or more $R_{2a}$ and wherein pyrazolyl, imidazolyl, indolyl, tetrazolyl, triazolyl, benzoimidazolyl, pyridinyl, imidazopyridinyl, dihydro-benzoimidazolyl, pyrazolopyridinyl, pyridinonyl, pyrimidinonylor pyrimidinyl is attached via a nitrogen heteroatom;

$R_{2a}$, at each occurrence, is independently selected from alkyl, haloalkyl, aryl, cycloalkyl, heteroaryl, heterocyclyl, halo, —$NH_2$, —CN, —$NO_2$, —C(=O)OH, —C(=O)O$(CR_8R_8)_rR_{10}$, —$O(CR_8R_8)_rR_{10}$, —OH or =O;

$R_3$ is alkyl;

$R_8$, at each occurrence, is independently hydrogen or alkyl;

$R_{8a}$, at each occurrence, is independently hydrogen, alkyl or —C(=O)$(CR_8R_8)_rR_{15}$;

$R_{10}$, at each occurrence, is independently selected from alkyl or aryl, wherein the alkyl or aryl may be optionally substituted with one or more $R_{10a}$;

$R_{10a}$, at each occurrence, is independently selected from alkyl, haloalkyl, aryl, cycloalkyl, heteroaryl, heterocyclyl, halo, —$NH_2$, —CN, —$O(CR_8R_8)_rR_{14}$, —OH, —C(=O)$NR_{14}R_{14}$ or —$NR_{14}R_{14}$;

$R_{12}$ is alkyl, heteroaryl, —S(O)$_2$R$_{15}$, —C(=O)R$_{15}$, —C(=O)NH$_2$, —C(=O)NR$_8$R$_{15}$, or —C(=O)OR$_{15}$, wherein the alkyl or heteroaryl may be optionally substituted with one or more $R_{12a}$, and the heteroaryl contains 1-4 heteroatoms selected from N, O, and S;

$R_{12a}$, at each occurrence, is independently selected from alkyl, haloalkyl, aryl, cycloalkyl, heteroaryl, heterocyclyl, halo, —NH$_2$, —CN, —O(CR$_8$R$_8$)$_r$R$_{14}$, —OH, —C(=O)NR$_{14}$R$_{14}$ or —NR$_{14}$R$_{14}$;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, cycloalkyl, heteroaryl, heterocyclyl, halo, —NH$_2$, —CN, —O(CR$_8$R$_8$)$_r$R$_{14}$, —OH, or —NR$_{14}$R$_{14}$;

m, at each occurrence, is independently 0-2;

n is 1-2; and r, at each occurrence, is independently 0 or 1.

In one embodiment, compounds of the present invention, or a stereoisomer or pharmaceutically acceptable salt from thereof, are those in which:

Ring A is

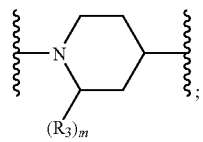

T is

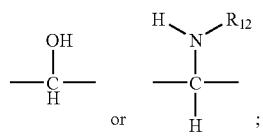

$R_1$ is phenyl, which may be optionally substituted with one or more $R_{1a}$;

$R_{1a}$, at each occurrence, is independently selected from halo, —CN, —OCH$_3$, —OCH$_2$CH$_3$, —OCH(CH$_3$)$_2$ or —OCH$_2$CH$_2$OH;

$R_2$ is pyrazolyl, imidazolyl, indolyl, triazolyl or pyrazolopyridinyl, all of which may be optionally substituted with one or more $R_{2a}$ and wherein pyrazolyl, imidazolyl, indolyl, triazolyl or pyrazolopyridinyl is attached via a nitrogen heteroatom;

$R_{2a}$, at each occurrence, is independently selected from alkyl, —CF$_3$, halo or —CN;

$R_3$ is alkyl;

$R_8$, at each occurrence, is independently hydrogen or alkyl;

$R_{12}$ is alkyl, heteroaryl, —S(O)$_2$R$_{15}$, —C(=O)R$_{15}$, —C(=O)NH$_2$, —C(=O)NR$_8$R$_{15}$, or —C(=O)OR$_{15}$, wherein the heteroaryl contains 1-4 heteroatoms selected from N, O, and S;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, halo, —NH$_2$, —CN, —O(CR$_8$R$_8$)$_r$R$_{14}$, —OH or —NR$_{14}$R$_{14}$;

m, at each occurrence, is independently 0-2;

n is 1-2; and r, at each occurrence, is independently 0 or 1.

In one embodiment, compounds of Formula (I), or a stereoisomer or pharmaceutically acceptable salt from thereof, are those compounds exemplified in the examples.

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-1 receptor activity comprising administering to a patient in need thereof a therapeutically effective amount of a compound of the present invention.

In another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of the present invention.

In another embodiment, the present invention is directed to a method for treating inflammatory bowel disease, comprising administering to a patient in need thereof a therapeutically effective amount of a compound of the present invention.

In another embodiment, the present invention is directed to a method for treating Crohn's disease, comprising administering to a patient in need thereof a therapeutically effective amount of a compound of the present invention.

In another embodiment, the present invention is directed to a method for treating psoriasis, comprising administering to a patient in need thereof a therapeutically effective amount of a compound of the present invention.

In another embodiment, the present invention is directed to a method for treating systemic lupus erythematosus, comprising administering to a patient in need thereof a therapeutically effective amount of a compound of the present invention.

In another embodiment, the present invention is directed to a method for treating multiple sclerosis, comprising administering to a patient in need thereof a therapeutically effective amount of a compound of the present invention.

In another embodiment, the present invention is directed to a method for treating rheumatoid arthritis, comprising administering to a patient in need thereof a therapeutically effective amount of a compound of the present invention.

In another embodiment, the present invention is directed to a method for treating psoriatic arthritis, comprising administering to a patient in need thereof a therapeutically effective amount of a compound of the present invention.

In another embodiment, the present invention is directed to a method for treating multiple myeloma, comprising administering to a patient in need thereof a therapeutically effective amount of a compound of the present invention.

In another embodiment, the present invention is directed to a method for treating allergies, for example, skin and mast cell degranulation in eye conjunctiva, comprising administering to a patient in need thereof a therapeutically effective amount of a compound of the present invention.

In another embodiment, the present invention is directed to a method for treating hepatocellular carcinoma, comprising administering to a patient in need thereof a therapeutically effective amount of a compound of the present invention.

In another embodiment, the present invention is directed to a method for treating osteoporosis, comprising administering to a patient in need thereof a therapeutically effective amount of a compound of the present invention.

In another embodiment, the present invention is directed to a method for treating renal fibrosis, comprising administering to a patient in need thereof a therapeutically effective amount of a compound of the present invention.

In another embodiment, the present invention is directed to a method for treating inflammatory diseases, for example, inflammatory diseases which are at least partially mediated by CCR-1, comprising administering to a patient in need thereof a therapeutically effective amount of a compound of the present invention.

In another embodiment, the present invention is directed to a method for modulation of CCR1 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-1 receptor activity comprising administering to a patient in need thereof a therapeutically effective amount of a pharmaceutical composition comprised of a compound of the present invention and one or more active ingredients.

In yet another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-1, comprising administering to a patient in need thereof a therapeutically effective amount of a pharmaceutical composition comprised of a compound of present invention and one or more active ingredients.

In another embodiment, the present invention is directed to a method for modulation of CCR-1 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, atherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent as known to one of ordinary skill in the art.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with ($R_4$) and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

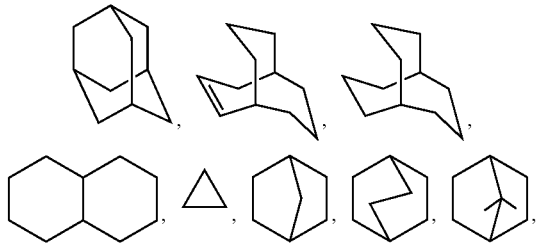

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings, for example:

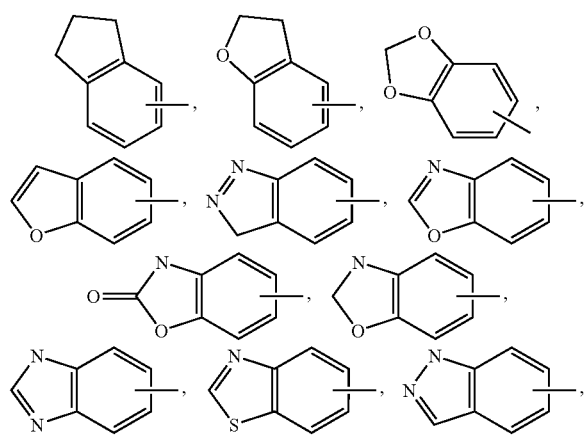

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.
The term "nitro" as used herein, refers to an $NO_2$ group.
The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31, (Academic Press, 1996);

b) *Design of Prodrugs*, edited by H. Bundgaard (Elsevier, 1985);

c) *A Textbook of Drug Design and Development*, P. Krogsgaard-Larsen and H. Bundgaard, eds. Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

As shown in Scheme 1, chemokine receptor antagonists of the formula (I) can be synthesized from azapines 1.1 and 1.6, which can be prepared according to a number of methods described in the literature (H. L. Fraser et al., *Progress in Heterocyclic Chemistry* 2005, 17, 261-303; P.-Q. Huang, *Synlett* 2006, 8, 1133-1149; S. Basra et al., *Strategies and Tactics in Organic Synthesis* 2004, 4, 315-346; M. G. P. Buffat, *Tetrahedron* 2004, 60, 1701-1729; S. Laschat and T. Dickner, *Synthesis* 2000, 13, 1781-1813; bridged variations have also been described, see: J. Cheng et al., *Bioorg. Med. Chem. Lett.* 2004, 14, 1775-1778; J. A. Lowe, III et al., *J. Med. Chem.* 1994, 37, 2831-2840). For example, an azapine of general structure 1.1 can be derivatized with a variety of different nucleophiles to form 1.2. In turn, compound 1.2 can be deprotected and the amine reacted with an electrophile to form common intermediate 1.4, a compound of formula (I). Compound 1.4 can be further derivatized to form 1.5, also a compound of formula (I). Alternatively, compounds 1.4 and 1.5 can be accessed via a path involving initial amine conjugation (1.6 to 1.7), followed by homologation/activation and reaction with a suitable nucleophile (1.7 to 1.8 to 1.4). The choice of protecting groups (PG) and synthetic route pursued will depend on the chemical structure of the desired embodiment of the invention. Furthermore, while the preparation of compounds of formula (I) has been described in Scheme 1, it will be apparent to one skilled in the art that various changes and modifications can be made to Scheme 1 without departing from the spirit and scope thereof.

SCHEME 1

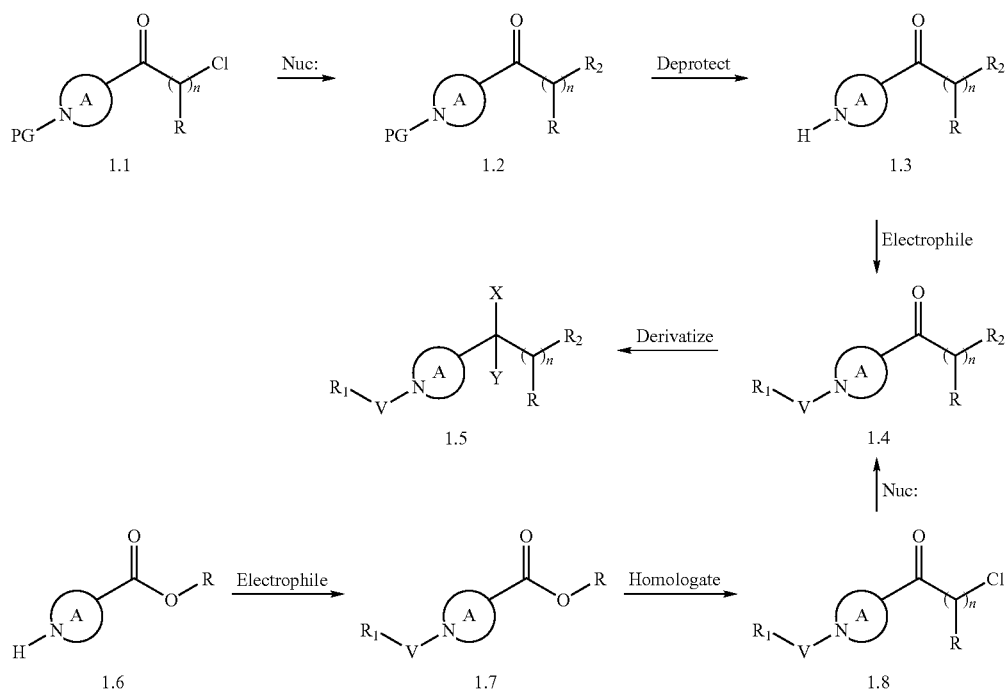

Scheme 2 illustrates one specific variant of the route described in Scheme 1 set forth above. Indeed, the syntheses of a number of the Examples (vide infra) follow the pathways outlined in Scheme 2. However, it will be apparent to one of ordinary skill in the art that Scheme 2 represents only a sampling of specific subsets of routes illustrated in Scheme 1, and that it would be possible to modify the illustrated routes to prepare additional compounds of formula (I). Indeed, several modifications to the illustrated route are shown in the synthesis of the following Examples.

SCHEME 2

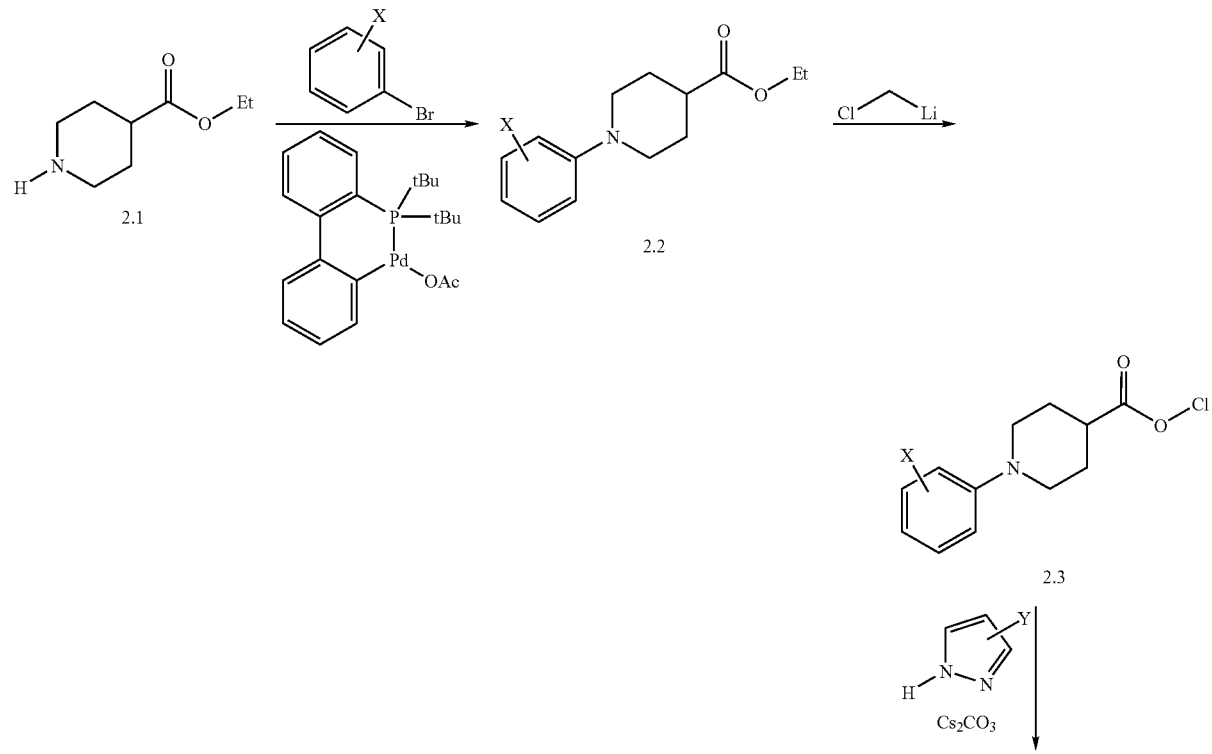

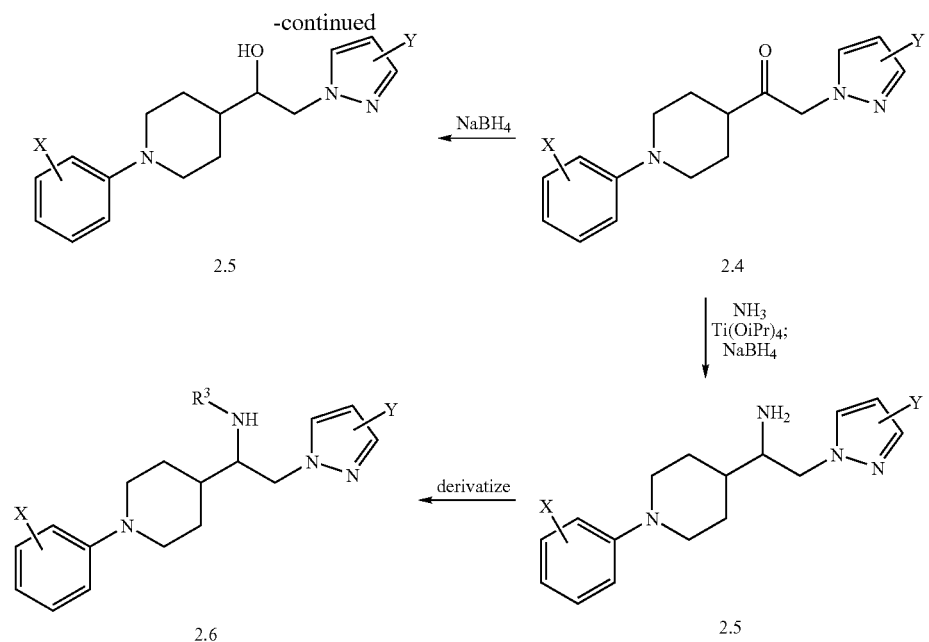

Other features of the invention will become apparent in the course of the following descriptions of exemplary embodiments that are given for illustration of the invention and are not intended to be limiting thereof.

EXAMPLES

Abbreviations used in the Examples are defined as "2×" for twice, "° C." for degrees Celsius, "g" for gram or grams, "mmol" for millimolar, "mL" for milliliter or milliliters, "M" for molar, "min" for minute or minutes, "mg" for milligram or milligrams, "h" for hour or hours, "LC" for liquid chromatography, "HPLC" for high performance liquid chromatography, "MS" for mass spectroscopy, "RT" for room temperature, "THF" for tetrahydrofuran, "Et$_2$O" for diethyl ether, "NH$_4$Cl" for ammonium chloride, "EtOAc" for ethyl acetate, "Na$_2$SO$_4$" for sodium sulfate, "DMSO" for dimethylsulfoxide, "K$_2$CO$_3$" for potassium carbonate, "CH$_2$Cl$_2$" for methylene chloride, "DCM" for methylene chloride, "TFA" for trifluoroacetic acid, "sat." for saturated, "NaHCO$_3$" for sodium bicarbonate, "N" for normal, "NaOH" for sodium hydroxide, "MeOH" for methanol, "NaCNBH$_3$" for sodium cyanoborohydride, "MgSO$_4$" for magnesium sulfate, "HATU" for O-(7-azabenzotriazol-1-yl)-N,N,N',N'-tetramethyluroniumhexafluorophosphate, "NaBH$_4$" for sodium borohydride, "Hex" for hexane, "H$_2$O" for water, "HCl" for hydrochloric acid, "AcOH" for acetic acid, "v/v" for volume to volume ratio. "D", "L", "R" and "S" are stereochemical designations familiar to those skilled in the art. Chemical names were derived using ChemDraw Ultra, version 8.0.8. When this program failed to provide a name for the exact structure in question, an appropriate name was assigned using the same methodology utilized by the program.

HPLC Conditions

Analytical HPLC Conditions:
Method a: Waters Sunfire S5 C18 4.6×30 mm; 5 ml/min flow; gradient: (0, 2 min), (0% B, 100% B); solvent B=90:10 MeOH/H$_2$O, 0.1% TFA; solvent A=90:10 H$_2$O/MeOH, 0.1% TFA.

Method c: Waters Sunfire S5 C18 4.6×50 mm; 4 ml/min flow; gradient: (0, 4 min), (0% B, 100% B); solvent B=90:10 MeOH/H$_2$O, 0.1% TFA; solvent A=90:10 H$_2$O/MeOH, 0.1% TFA.

Method c: YMC OD-S 5 micron, 4.6×50 mm; 4 ml/min flow; gradient: (0, 4 min), (0% B, 100% B); solvent B=90:10 MeOH/H$_2$O, 0.1% H$_3$PO$_4$; solvent A=90:10 H$_2$O/MeOH, 0.1% H$_3$PO$_4$.

Method d: Sunfire C18 3.5 micron 4.6×150 mm; 1 ml/min flow; gradient: (0, 15 min), (0%, 100% B); solvent B=95:5 CH$_3$CN/H$_2$O, 0.05% TFA; solvent A=95:5 H$_2$O/CH$_3$CN, 0.1% TFA.

Method e: Sunfire X-Bridge-Ph 4.6×50 mm; 1 ml/min flow; gradient: (0, 15 min), (0%, 100% B); solvent B=95:5 CH$_3$CN/H$_2$O, 0.05% TFA; solvent A=95:5 H$_2$O/CH$_3$CN, 0.1% TFA.

Preparative HPLC Conditions:
Method f: Waters Sunfire C-18 19×100 mm; 10 ml/min flow; gradient: (0, 10 min), (0% B, 100% B); solvent B=90:10 MeOH/H$_2$O, 0.1% TFA; solvent A=90:10 H$_2$O/MeOH, 0.1% TFA.

Method g: Phenomenex Luna 21.2×100 mm Luna C18; 10 ml/min flow; gradient: (0, 10 min), (0% B, 100% B); solvent B=90:10 MeOH/H$_2$O, 0.1% TFA; solvent A=90:10 H$_2$O/MeOH, 0.1% TFA.

Preparations of Intermediates

Preparation 1

Synthesis of 2-(5-methyl-1H-pyrazol-3-yl)pyridine

Preparation 1: This material was synthesized according to the procedure described in *Journal of Medicinal Chemistry* 1968, 11, 981.

Preparation 2

Synthesis of 2-(4-chloro-5-methyl-1H-pyrazol-3-yl)pyridine

Preparation 2: A solution of 2-(5-methyl-1H-pyrazol-3-yl)pyridine (500 mg, 3.15 mmol) in acetonitrile (912 mL) was treated with N-chlorosuccinimide in 6 portions and the resulting mixture stirred at 70° C. for 14 h. The mixture was cooled and then concentrated in vacuo to yield a residue. The residue was partitioned between EtOAc (8 mL) and H$_2$O (3 mL). The organic phase was washed with brine, dried (Na$_2$SO$_4$) and concentrated in vacuo to yield a residue. The residue was purified by flash chromatography on silica gel using 20-80% EtOAc in hexanes to give the title compound (300 mg, 53%).

Preparation 3

Synthesis of 2-(5-methyl-1H-pyrazol-3-yl)pyrimidine

Preparation 3, Step 1: A solution of 2-cyanopyrimidine, (26 g, 24.8 mmol) in anhydrous MeOH (150 mL) was placed in a 250 ml pressure bottle and cooled to 0° C. Anhydrous HCl was bubbled through the solution for 10 min. The reaction vessel was capped and heated at 55° C. for 14 h. The mixture was cooled and concentrated in vacuo. The resultant residue was treated with CHCl$_3$/isopropyl (3:1, 150 mL) and washed with saturated NaHCO$_3$ and brine. The organic phase was dried (Na$_2$SO$_4$) and concentrated to give methylpyrimidine-2-carboxylate (2.1 g, 65%).

Preparation 3, Step 2: A sample of methylpyrimidine-2-carboxylate was converted to the title compound according to the method described in *Journal of Medicinal Chemistry* 1968, 11, 981.

Preparation 4

Synthesis of 2-(4-chloro-5-methyl-1H-pyrazol-3-yl)pyrimidine

Preparation 4: The title compound was prepared from 2-(5-methyl-1H-pyrazol-3-yl)pyrimidine according to the method described in Preparation 2 (32% yield obtained).

Example 1a 1-(1-(4-Chloro-3-methoxyphenyl)piperidin-4-yl)-2-(4-chloro-5-methyl-3-(trifluoromethyl)-1H-pyrazol-1-yl)ethanone

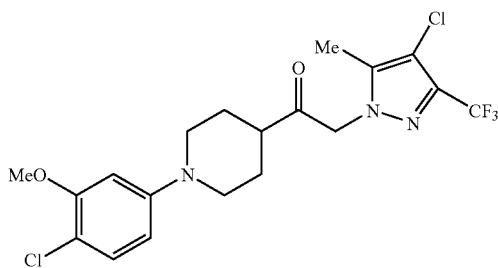 [SMILES: COc1cc(N2CCC(C(=O)Cn3nc(C(F)(F)F)c(Cl)c3C)CC2)ccc1Cl]

Step 1: A 10-mL round bottom flask containing a magnetic stir bar and fitted with a condenser and a inert gas inlet was charged successively with sodium tert-butoxide (304 mg, 3.16 mmol), acetato (2'-di-t-butylphosphino-1,1'-biphenyl-2-yl) palladium (II) (20.90 mg, 0.045 mmol) and a solution of 4-bromo-1-chloro-2-methoxybenzene (500 mg, 2.258 mmol) and ethyl piperidine-4-carboxylate (426 mg, 2.71 mmol) in anhydrous toluene (2.5 mL). The flask was purged with argon and the mixture heated at 80° C. After 45 min, the reaction was cooled to RT, diluted with Et$_2$O (50 mL) and washed with water (2×15 mL) and brine (15 mL). The organic layer was dried (MgSO$_4$) and concentrated on a rotary evaporator to give the crude product, which was purified by flash chromatography using a 12 g silica gel cartridge and 20:1 Hex/EtOAc to 10:1 Hex/EtOAc to elute the product. The fractions containing the product were pooled and concentrated on a rotary evaporator to give ethyl 1-(4-chloro-3-methoxyphenyl)piperidine-4-carboxylate (380 mg, 1.276 mmol, 56% yield) as a colorless oil. LC/MS [M+H]$^+$=298.28. $^1$H-NMR (400 MHz, CDCl$_3$) δ 7.18 (1 H, d, J=8.57 Hz), 6.50 (1 H, s), 6.44 (1 H, s), 4.15 (2H, q, J=7.10 Hz), 3.87 (3 H, s), 3.58 (2 H, dt, J=12.47, 3.65 Hz), 2.79 (2 H, s), 2.38-2.47 (1 H, m), 2.02 (2 H, d, J=11.42 Hz), 1.88 (2 H, s), 1.26 (3 H, t, J=7.14 Hz).

Step 2: A dry 3-neck, 250-mL round bottom flask was charged with ethyl 1-(4-chloro-3-methoxyphenyl)piperidine-4-carboxylate (3.0 g, 10.07 mmol), anhydrous THF (50.4 mL) and chloroiodomethane (0.878 mL, 12.09 mmol). The flask was fitted with a rubber septum and pressure-equalized dropping funnel topped with an inert gas inlet and placed under a nitrogen atmosphere. The mixture was cooled to −78° C. (CO$_2$/acetone bath). Methyllithium (7.56 mL of a 1.6 M solution in Et$_2$O, 12.09 mmol) was added dropwise to the mixture from the dropping funnel over 10 min. The mixture was stirred at −78° C. for 1 h and then quenched with saturated NH$_4$Cl (10 mL) and warmed to RT. The mixture was adjusted to a pH=6 and extracted with Et$_2$O (3×75 mL). The extract was washed with brine, dried (Na$_2$SO$_4$) and concentrated on a rotary evaporator. The resultant residue was purified by flash chromatography using an 80 g silica gel cartridge and gradient elution from 20:1 Hex/EtOAc to 2:1 Hex/EtOAc. The fractions containing the product were pooled and concentrated on a rotary evaporator to give 2-chloro-1-(1-(4-chloro-3-methoxyphenyl)piperidin-4-yl)ethanone (1.3 g, 4.30 mmol, 43% yield) as a pale orange solid. LC/MS [M+H]$^+$=302. $^1$H-NMR (400 MHz, CDCl$_3$) δ ppm 7.19 (1 H, d, J=8.57 Hz), 6.50 (1 H, s), 6.44 (1 H, s), 4.18 (2 H, s), 3.87 (3 H, s), 3.62-3.71 (2 H, m), 2.75-2.86 (3 H, m), 1.97 (2 H, s), 1.84 (2 H, s).

Step 3: A 10-mL round-bottom flask was charged with 4-chloro-5-methyl-3-(trifluoromethyl)-1H-pyrazole (249 mg, 1.35 mmol), cesium carbonate (586 mg, 1.80 mmol) and anhydrous acetonitrile (2.0 mL). The mixture was stirred at RT under argon for 15 min. A solution of 2-chloro-1-(1-(4-chloro-3-methoxyphenyl)piperidin-4-yl)ethanone (272 mg, 0.9 mmol) in anhydrous acetonitrile (1.5 mL) was added dropwise to the heterogeneous within 1.5 min, and the resulting mixture was stirred at RT for 14 h to give a bright yellow mixture. The bright yellow mixture was diluted with EtOAc (15 mL), washed with brine (2×10 mL), dried (MgSO$_4$) and concentrated on a rotary evaporator to give the crude product as yellow oil. The yellow oil was purified by flash chromatography using a 12 g silica gel cartridge and gradient elution from 10:1 Hex/EtOAc to 3:1 Hex/EtOAc. The fractions containing the product were pooled and concentrated on a rotary evaporator to give Example 1a (140 mg, 0.311 mmol, 34% yield) as a pale-yellow solid. LC/MS [M+H]$^+$=450.29. HPLC t$_R$=3.44 min [Waters Sunfire C18 4.6×50 mm column, 4 min gradient from 10/90/0.1 MeOH/H$_2$O/TFA to 90/10/0.1 MeOH/H$_2$O/TFA at 4 mL/min flow rate]. $^1$H-NMR (400 MHz, CDCl$_3$) δ ppm 7.18 (1 H, d, J=8.57 Hz), 6.50 (1 H, s), 6.44 (1 H, s), 4.15 (2 H, q, J=7.10 Hz), 3.87 (3 H, s), 3.58 (2 H, dt, J=12.47, 3.65 Hz), 2.79 (2 H, s), 2.38-2.47 (1 H, m), 2.02 (2 H, d, J=11.42 Hz), 1.88 (2 H, s), 1.26 (3 H, t, J=7.14 Hz).

Examples 1b to 1k

Examples 1b to 1k were made using the methods exemplified above in Example 1a. Data for Examples 1b to 1k are provided in Table 1 below. The substituents listed in each column are to be paired with the structure embedded in the table heading. In the synthesis of the examples, substitutions for key reagents were made in Step 3 of the procedure outlined in Example 1a, as will be evident to one skilled in the art.

The data in the "MS" column represent the values observed for the $(M+H)^+$ ions in electrospray mass spectroscopy experiments. For mass spectra in which multiple isotopes were observed, the major ion is listed. {Note: For compounds with one or two Cl atoms, this is typically the first ion of two significant ions; for compounds with three Cl atoms, this is typically the second ion of three significant ions.} The data in the "HPLC" column indicate the retention time with the method conditions shown in brackets.

TABLE 1

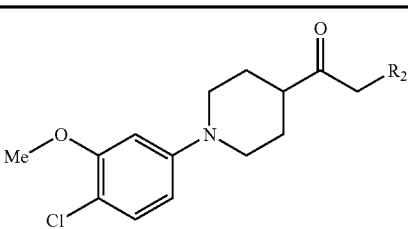

| Example | Name | R$_2$ | MS | HPLC t$_R$ (method) |
|---|---|---|---|---|
| 1b | 1-(2-(1-(4-Chloro-3-methoxyphenyl)piperidin-4-yl)-2-oxoethyl)-3-methyl-1H-benzo[d]imidazol-2(3H)-one | 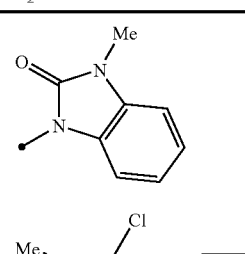 | 414.1 | 3.13 (c) |
| 1c | 1-(1-(4-Chloro-3-methoxyphenyl)piperidin-4-yl)-2-(4-chloro-5-methyl-3-(pyridin-2-yl)-1H-pyrazol-1-yl)ethanone | 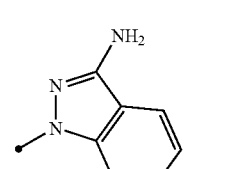 | 459.1 | 2.66 (c) |
| 1d | 2-(3-Amino-1H-pyrazolo[3,4-b]pyridin-1-yl)-1-(1-(4-chloro-3-methoxyphenyl)piperidin-4-yl)ethanone | 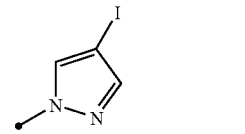 | 400.1 | 1.91 (b) |
| 1e | 1-(1-(4-Chloro-3-methoxyphenyl)piperidin-4-yl)-2-(4-iodo-1H-pyrazol-1-yl)ethanone | 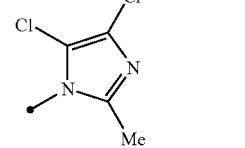 | 460.0 | 3.26 (c) |
| 1f | 1-(1-(4-Chloro-3-methoxyphenyl)piperidin-4-yl)-2-(4,5-dichloro-2-methyl-1H-imidazol-1-yl)ethanone | 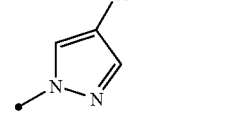 | 416.1 | 12.47 (e) |
| 1g | 2-(4-Chloro-1H-pyrazol-1-yl)-1-(1-(4-chloro-3-methoxyphenyl)piperidin-4-yl)ethanone | 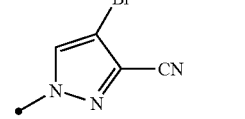 | 368.1 | 3.02 (b) |
| 1h | 4-Bromo-1-(2-(1-(4-chloro-3-methoxyphenyl)piperidin-4-yl)-2-oxoethyl)-1H-pyrazole-3-carbonitrile | | 437.1 | 11.69 (e) |

TABLE 1-continued

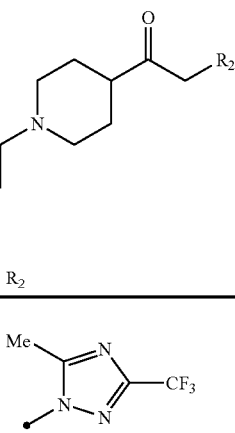

| Example | Name | R₂ | MS | HPLC $t_R$ (method) |
|---|---|---|---|---|
| 1i | 1-(1-(4-Chloro-3-methoxyphenyl)piperidin-4-yl)-2-(5-methyl-3-(trifluoromethyl)-1H-1,2,4-triazol-1-yl)ethanone | 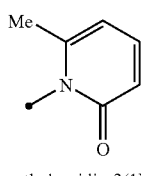 | 417.2 | 8.01 (e) |
| 1j | 1-(2-(1-(4-Chloro-3-methoxyphenyl)piperidin-4-yl)-2-oxoethyl)-6-methylpyridin-2(1H)-one | 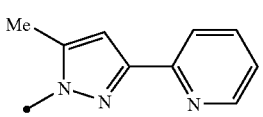<br>1,6-dimethylpyridin-2(1H)-one | 375.1 | 2.21 (c) |
| 1k | 1-(1-(4-Chloro-3-methoxyphenyl)piperidin-4-yl)-2-(5-methyl-3-(pyridin-2-yl)-1H-pyrazol-1-yl)ethanone | | 425.2 | 2.07 (c) |

Example 11

2-(4-Chloro-5-methyl-3-(trifluoromethyl)-1H-pyrazol-1-yl)-1-(1-(2,4-dichloro-5-methoxyphenyl)piperidin-4-yl)ethanone

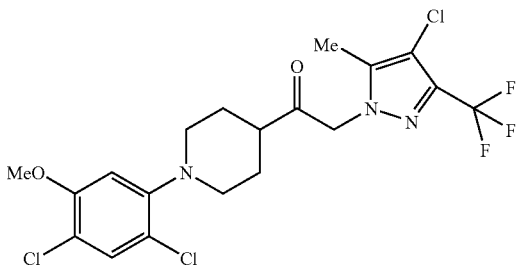 [SMILES: COc1cc(N2CCC(C(=O)Cn3nc(C(F)(F)F)c(Cl)c3C)CC2)c(Cl)cc1Cl]

Step 1: A 10-mL round bottom flask containing a magnetic stir bar and fitted with a condenser and a inert gas inlet was charged successively with sodium tert-butoxide (304 mg, 3.16 mmol), acetato(2'-di-t-butylphosphino-1,1'-biphenyl-2-yl)palladium (II) (20.90 mg, 0.045 mmol) and a solution of 4-bromo-1-chloro-2-methoxybenzene (500 mg, 2.258 mmol) and ethyl piperidine-4-carboxylate (426 mg, 2.71 mmol) in anhydrous toluene (2.5 mL). The flask was purged with nitrogen and the mixture heated at 80° C. After 45 minutes, the mixture was cooled to RT, diluted with Et₂O (50 mL) and washed with water (2×15 mL) and brine (15 mL). The organic layer was dried (MgSO₄) and concentrated on a rotary evaporator to give the crude product. The crude product was purified by flash chromatography using a 12 g silica gel cartridge and gradient elution from 20:1 Hex/EtOAc to 10:1 Hex/EtOAc. The fractions containing the product were pooled and concentrated on a rotary evaporator to give ethyl 1-(4-chloro-3-methoxyphenyl)piperidine-4-carboxylate (380 mg, 1.276 mmol, 56% yield) as a colorless oil. The colorless oil was treated with 4.0 M HCl/dioxane (2 mL) and the resulting suspension was diluted with Et₂O (4 mL) and stirred at RT for 10 min. The hydrochloride product was collected by filtration, washed with Et₂O and dried in vacuo to give ethyl 1-(4-chloro-3-methoxyphenyl)piperidine-4-carboxylate, hydrochloride salt as a white solid (383 mg).

Step 2: A 25-mL round bottom flask containing a magnetic stir bar and fitted with an inert gas inlet was charged with ethyl 1-(4-chloro-3-methoxyphenyl)piperidine-4-carboxylate, hydrochloride salt (367 mg, 1.23 mmol), AcOH (6 mL) and water (3.0 mL). The mixture was treated with N-chlorosuccinimide (206 mg, 1.54 mmol) in one portion. The mixture was stirred under argon at RT overnight and then diluted with water (20 mL) and Et₂O (60 mL). The pH of the mixture was adjusted to a pH=10. The phases were separated and the aqueous phase was extracted with Et₂O. The combined Et₂O extracts were washed with brine, dried (MgSO₄) and concentrated on a rotary evaporator. The resultant residue was purified by flash chromatography using a 12 g silica gel cartridge and gradient elution from 50:1 Hex/EtOAc to 20:1 Hex/EtOAc to elute the product. The fractions containing the product were pooled and concentrated on a rotary evaporator to give ethyl 1-(2,4-dichloro-5-methoxyphenyl)piperidine-4-carboxylate (255 mg, 0.77 mmol, 70% yield) as a clear oil, which solidified on standing at room temperature. ¹H-NMR (400 MHz, CDCl₃) δ ppm 7.33 (1 H, s), 6.58 (1 H, s), 4.15 (2 H, qd, J=7.04, 6.87 Hz), 3.87 (3 H, s), 3.33 (2 H, d, J=11.70 Hz), 2.70 (2 H, t, J=9.66 Hz), 2.43 (1 H, dq, J=10.17, 5.09 Hz), 1.94-2.05 (4 H, m), 1.22-1.30 (3 H, m).

Step 3: An oven-dried, 50-mL 2-neck round bottom flask containing a stir bar was fitted with an inert gas inlet and a rubber septum and placed under argon. The flask was charged with ethyl 1-(2,4-dichloro-5-methoxyphenyl)piperidine-4-carboxylate (233 mg, 0.701 mmol) and anhydrous THF (5 mL) and chloroiodomethane (0.102 mL, 1.403 mmol). The mixture was cooled to −70° C. (internal temperature). Once at the prescribed temperature, a solution of methyllithium (0.877 mL of 1.6 M in Et₂O, 1.403 mmol) was added dropwise to the mixture via syringe over 5 min. At the conclusion of this period, the mixture was stirred at −70° C. (internal temperature) for 1.5 h and then quenched by adding saturated NH₄Cl (2 mL). The pH of the mixture was adjusted to pH 7.5 by careful addition of 2 M HCl. Once at the prescribed pH, the mixture was extracted with EtOAc (25 mL). The aqueous phase was back-extracted with EtOAc and the combined extracts washed with brine, dried (MgSO₄) and concentrated on a rotary evaporator to give 2-chloro-1-(1-(2,4-dichloro-5-methoxyphenyl)piperidin-4-yl)ethanone (242 mg). LC-MS: 336.24, [M+H]+; tR=3.84 min (b).

Step 4: A solution of 4-chloro-5-methyl-3-(trifluoromethyl)-1H-pyrazole (194 mg, 1.052 mmol), cesium carbonate (457 mg, 1.402 mmol) and acetonitrile (2 mL) was stirred at RT under nitrogen for 15 min and then cooled to 5-10° C. The mixture was treated with a solution of 2-chloro-1-(1-(2,4-dichloro-5-methoxyphenyl)piperidin-4-yl)ethanone (236 mg, 0.701 mmol) in acetonitrile (1 mL), and then allowed to warm up to RT where it stirred overnight. After this time, the mixture was diluted with EtOAc (20 mL), washed with brine (2×10 mL), dried (MgSO₄) and concentrated on a rotary evaporator. The resultant residue was purified using a 12 g silica gel cartridge and gradient elution from 20:1 Hex/EtOAc to 3:1 Hex/EtOAc. The fractions containing the product were pooled and concentrated on a rotary evaporator to give Example 11 (112 mg, 0.187 mmol, 26% yield) as a pale-yellow solid. LC/MS [M+H]⁺=483.98; t$_R$=4.26 min (b). ¹H-NMR (400 MHz, CDCl₃) δ ppm 7.35 (1 H, s), 6.57 (1 H, s), 5.04 (2 H, s), 3.88 (3 H, s), 3.41 (2 H, d, J=12.21 Hz), 2.67-2.77 (2 H, m), 2.55-2.66 (1 H, m, J=10.30, 10.30, 5.09, 4.83 Hz), 2.17 (3 H, s), 1.94-2.04 (4 H, m)

Example 2a 1-(1-(4-Chloro-3-methoxyphenyl)piperidin-4-yl)-2-(4-chloro-5-methyl-3-(trifluoromethyl)-1H-pyrazol-1-yl)ethanol

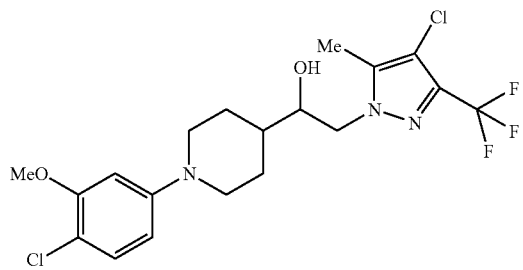 [SMILES: COc1cc(N2CCC(C(O)Cn3nc(C(F)(F)F)c(Cl)c3C)CC2)ccc1Cl]

A 25-mL round-bottom flask containing a magnetic stir bar was fitted with an inert gas inlet and charged with 1-(1-(4-chloro-3-methoxyphenyl)piperidin-4-yl)-2-(4-chloro-5-methyl-3-(trifluoromethyl)-1H-pyrazol-1-yl)ethanone (128 mg, 0.284 mmol) and MeOH (10 mL). The contents of the flask were placed under nitrogen atmosphere. Sodium borohydride (10.75 mg, 0.284 mmol) was added and the mixture was stirred at ambient temperature for 30 min. At the conclusion of this period, the mixture was treated with saturated sodium bicarbonate (3 mL) and the volatiles were removed on a rotary evaporator. The resultant residue was partitioned between EtOAc and brine. The EtOAc phase was dried (MgSO₄), concentrated in vacuo, and purified by RP-HPLC (method f) to afford Example 2a as a white powder (80 mg, 50% yield) after lyophilization. LC/MS [M+H]⁺=452.27; t$_R$=3.30 min (method b). ¹H-NMR (400 MHz, CDCl₃) δ ppm 7.43 (1 H, d, J=8.65 Hz), 7.32 (1 H, d, J=2.54 Hz), 6.87 (1 H, dd, J=8.65, 2.54 Hz), 4.17-4.23 (1 H, m), 3.99-4.10 (2 H, m), 3.92 (3 H, s), 3.77 (2 H, d, J=11.70 Hz), 3.16 (2 H, td, J=11.95, 3.05 Hz), 2.31 (3 H, s), 2.12-2.22 (3 H, m), 2.05 (1 H, d, J=14.24 Hz), 1.78-1.87 (1 H, m).

Examples 2b to 2j

Examples 2b to 2j were made using the methods exemplified above in Example 2a. Data for Examples 2b to 2j are provided in Table 2 below. The substituents listed in each column are to be paired with the structure embedded in the table heading. In the synthesis of the examples, substitutions for key reagents were made in Step 1 of the procedure outlined in Example 2a, as will be evident to one skilled in the art. The data in the "MS" column represent the values observed for the (M+H)⁺ ions in electrospray mass spectroscopy experiments. For mass spectra in which multiple isotopes were observed, the major ion is listed. {Note: For compounds with one or two Cl atoms, this is typically the first ion of two significant ions; for compounds with three Cl atoms, this is typically the second ion of three significant ions.} The data in the "HPLC" column indicate the retention time with the method conditions shown in brackets.

TABLE 2

| Example | Name | R₂ | MS | HPLC t$_R$ (method) |
|---|---|---|---|---|
| 2b | 1-(1-(4-Chloro-3-methoxyphenyl)piperidin-4-yl)-2-(4-chloro-5-methyl-3-(pyridin-2-yl)-1H-pyrazol-1-yl)ethanol | | 461.2 | 2.14 (c) |
| 2c | 2-(3-Amino-1H-pyrazolo[3,4-b]pyridin-1-yl)-1-(1-(4-chloro-3-methoxyphenyl)piperidin-4-yl)ethanol | | 402.0 | 1.79 (b) |
| 2d | 1-(1-(4-Chloro-3-methoxyphenyl)piperidin-4-yl)-2-(5-methyl-3-(trifluoromethyl)-1H-pyrazol-1-yl)ethanol | | 418.1 | 2.67 (c) |
| 2e | 2-(4-Bromo-1H-pyrazol-1-yl)-1-(1-(4-chloro-3-methoxyphenyl)piperidin-4-yl)ethanol | | 414.9 | 2.39 (b) |
| 2f | 1-(1-(4-Chloro-3-methoxyphenyl)piperidin-4-yl)-2-(5-(trifluoromethyl)-1H-pyrazol-1-yl)ethanol | | 404.2 | 2.60 (b) |
| 2g | 1-(1-(4-Chloro-3-methoxyphenyl)piperidin-4-yl)-2-(4-chloro-5-phenyl-3-(trifluoromethyl)-1H-pyrazol-1-yl)ethanol | | 514.3 | 3.81 (b) |
| 2h | 1-(1-(4-Chloro-3-methoxyphenyl)piperidin-4-yl)-2-(5-methyl-3-(trifluoromethyl)-1H-1,2,4-triazol-1-yl)ethanol | | 419.23 | 6.28 (d) |
| 2i | 1-(2-(1-(4-Chloro-3-methoxyphenyl)piperidin-4-yl)-2-hydroxyethyl)-3-methyl-1H-benzo[d]imidazol-2(3H)-one | | 416.2 | 2.84 (c) |
| 2j | 2-(4-Chloro-5-methyl-3-(pyridin-2-yl)-1H-pyrazol-1-yl)-1-(1-(2,4-dichloro-5-methoxyphenyl)piperidin-4-yl)ethanol | | 466.1 | 2.66 (c) |

Example 2k 2-(4-Chloro-5-methyl-3-(trifluoromethyl)-1H-pyrazol-1-yl)-1-(1-(2,4-dichloro-5-methoxyphenyl)piperidin-4-yl)ethanol and separation into its two enantiomers

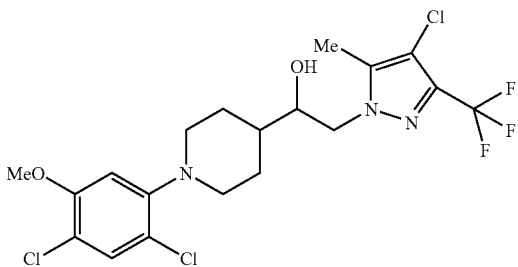 [SMILES: COc1cc(N2CCC(C(O)Cn3nc(C(F)(F)F)c(Cl)c3C)CC2)c(Cl)cc1Cl]

Step 1: A flask containing a solution of 2-(4-chloro-5-methyl-3-(trifluoromethyl)-1H-pyrazol-1-yl)-1-(1-(2,4-dichloro-5-methoxyphenyl)piperidin-4-yl)ethanone (105 mg, 0.217 mmol) in dry MeOH (8 mL) was placed in a RT water bath and charged with sodium borohydride (8.20 mg, 0.217 mmol) in one portion. The mixture became homogeneous within 1 min of the addition of the sodium borohydride. After 45 min, the reaction was treated with saturated sodium bicarbonate and the methanol was removed on a rotary evaporator. The resultant residue was partitioned between EtOAc (20 mL) and brine. The organic phase was dried (MgSO$_4$) and concentrated in vacuo to yield a residue. The residue was purified by preparative HPLC (method f) to afford racemic Example 2k as an off-white solid after lyophilization. LC/MS [M+H]$^+$=486.02; HPLC t$_R$=4.18 min (method b). 1H NMR (400 MHz, CDCl$_3$) δ ppm 7.19 (1 H, s), 6.60 (1 H, s), 4.14 (1 H, dd, J=13.73, 2.03 Hz), 3.95-4.02 (1 H, m), 3.87-3.94 (1 H, m), 3.80-3.85 (3 H, m), 3.40 (2 H, d, J=12.21 Hz), 2.66 (2 H, t, J=11.19 Hz), 2.22-2.31 (3 H, m), 1.91 (1 H, d, J=12.21 Hz), 1.74-1.79 (1 H, m), 1.59-1.70 (3 H, m).

Step 2: Racemic Example 2k (Step 1 above) was purified using chiral-SFC and the following conditions: column, Chiralpak AD-H (3×25 cm, 5 micron); BPR pressure, 100 bars; temperature, 35° C.; flow rate, 70 mL/min; mobile phase, CO$_2$/MeOH (85/15); detector wavelength, 274 nm; sample preparation, 19 mg/mL in MeOH. This separation provided enantiomer 1 and enantiomer 2. These materials could be distinguished on a Chiralpak AD analytical column (0.46×25 cm, 10 micron; BPR pressure, 100 bars; temperature, 35° C.; flow rate, 3.0 mL/min; mobile phase, 85/15 CO$_2$/MeOH; detector wavelength, 220 nm): enantiomer 1 t$_R$=6.26 min and enantiomer 2 t$_R$=7.76 min.

Example 3

2-(4-Chloro-5-methyl-3-(trifluoromethyl)-1H-pyrazol-1-yl)-1-(1-(2,4-dichloro-5-methoxyphenyl)piperidin-4-yl)ethyl acetate

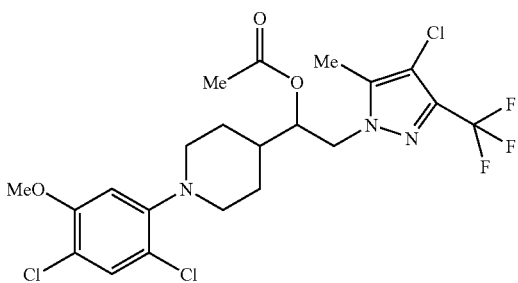 [SMILES: COc1cc(N2CCC(C(Cn3nc(C(F)(F)F)c(Cl)c3C)OC(C)=O)CC2)c(Cl)cc1Cl]

A solution of 2-(4-chloro-5-methyl-3-(trifluoromethyl)-1H-pyrazol-1-yl)-1-(1-(2,4-dichloro-5-methoxyphenyl)piperidin-4-yl)ethanol (31 mg, 0.064 mmol) in anhydrous DCM (1.5 mL) was treated with acetic anhydride (0.012 mL, 0.127 mmol) and 4-(N,N-dimethylamino)pyridine (2 mg). The mixture was stirred at RT for 1 h. After this time, the mixture was diluted with DCM (15 mL), and washed sequentially with 1 M HCl, sat. NaHCO$_3$ and brine. The mixture was dried (MgSO$_4$) and concentrated in vacuo. The resultant residue was purified using a 4 g silica gel cartridge and gradient elution with EtOAc and Hexanes to give Example 3 (30 mg, 0.057 mmol, 89% yield) as a pale yellow solid. $^1$H-NMR (400 MHz, CDCl$_3$) δ ppm 7.16 (1 H, s), 6.49 (1 H, s), 5.02 (1 H, dt, J=7.74, 4.82 Hz), 4.13-4.25 (2 H, m), 3.76-3.82 (3 H, m), 3.34 (1 H, d, J=4.28 Hz), 3.32 (1 H, s), 2.52 (2 H, d, J=12.84 Hz), 2.22 (3 H, s), 1.93 (3 H, s), 1.77 (2 H, d, J=11.33 Hz), 1.53-1.65 (3 H, m).

Example 4a 2-(4-Chloro-5-methyl-3-(trifluoromethyl)-1H-pyrazol-1-yl)-1-(1-(2,4-dichloro-5-methoxyphenyl)piperidin-4-yl)ethanamine

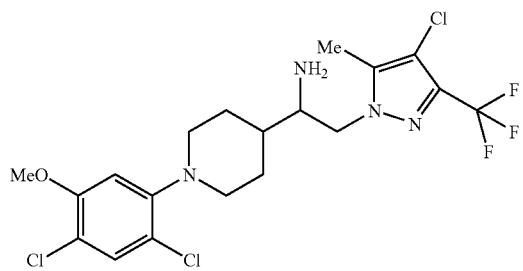

A mixture of 2-(4-chloro-5-methyl-3-(trifluoromethyl)-1H-pyrazol-1-yl)-1-(1-(2,4-dichloro-5-methoxyphenyl)piperidin-4-yl)ethanone (450 mg, 0.928 mmol), absolute EtOH (6.00 mL), CH$_2$Cl$_2$ (3 mL), ammonia (1.326 mL of a 7M solution in EtOH; 9.28 mmol), and titanium(IV) isopropoxide (1.088 mL, 3.71 mmol) was stirred at RT in a stoppered, nitrogen-flushed flask for 24 h. After this time, the mixture was treated with sodium borohydride (140 mg, 3.71 mmol) and stirred at RT for 2 h. At the conclusion of this period, the mixture was poured into aqueous concentrated NH$_4$OH (5 mL), diluted with CH$_2$Cl$_2$ (115 mL) and then stirred vigorously for 30 min before being filtered through Celite. The filtrate was placed in a separatory funnel and the phases separated. The aqueous phase was extracted with CH$_2$Cl$_2$ (3 times), and the combined extracts were washed with brine, dried (MgSO$_4$) and concentrated to give the crude product. The crude product was purified by flash chromatography on a 12 g silica gel cartridge eluting first with 100% EtOAc and then 10% MeOH/CH$_2$Cl$_2$ to give Example 4a (200 mg, 0.412 mmol, 44% yield) as a yellow solid. $^1$H-NMR (400 MHz, CDCl$_3$) δ ppm 7.31 (1 H, s), 6.55 (1 H, s), 4.33-4.43 (2 H, m), 3.84 (3 H, s), 3.61-3.75 (1 H, m), 3.40 (2 H, d, J=10.99 Hz), 2.51-2.76 (2 H, m), 2.32 (3 H, s), 1.91-2.01 (2 H, m), 1.84 (1 H, d, J=12.30 Hz), 1.60-1.71 (2 H, m).

Example 4b 2-(4-Chloro-5-methyl-3-(trifluoromethyl)-1H-pyrazol-1-yl)-1-(1-(2,4-dichloro-5-methoxyphenyl)piperidin-4-yl)-N-methylethanamine

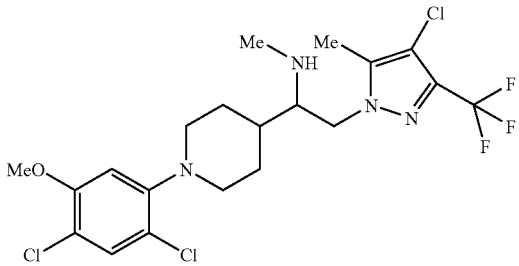 [SMILES: CNC(Cn1nc(C(F)(F)F)c(Cl)c1C)C1CCN(c2cc(OC)c(Cl)cc2Cl)CC1]

A solution of 2-(4-chloro-5-methyl-3-(trifluoromethyl)-1H-pyrazol-1-yl)-1-(1-(2,4-dichloro-5-methoxyphenyl)piperidin-4-yl)ethanone (130 mg, 0.268 mmol) in anhydrous CH$_2$Cl$_2$ (1.0 mL) and absolute ethanol (0.5 mL) was treated with methylamine hydrochloride (36.2 mg, 0.536 mmol) and triethylamine (0.075 mL, 0.536 mmol), followed by titanium (IV) isopropoxide (0.158 mL, 0.536 mmol). The flask was flushed with nitrogen, stoppered and stirred at RT overnight (12 h). At the conclusion of this period, the flask was fitted with an inert gas inlet and placed under nitrogen before being charged with sodium borohydride (15.22 mg, 0.402 mmol). After stirring at RT for 2 h, the mixture was quenched with 15% NH$_4$OH (2 mL) and stirred vigorously for 5 min. After this time, the mixture was diluted with CH$_2$Cl$_2$ (10 mL) and water (5 mL) before being filtered through Celite. The filtrate was placed in a separatory funnel and the phases were separated. The aqueous phase was extracted with CH$_2$Cl$_2$ (10 mL). The combined organic phases were washed with brine, dried (MgSO$_4$) and concentrated in vacuo. The resultant residue was purified by flash chromatography using a 4 g silica gel cartridge and gradient elution from 2:1 EtOAc/Hex to 100% EtOAc. The fractions containing the product were pooled and concentrated on a rotary evaporator to give Example 4b (19 mg, 0.031 mmol, 11% yield) as a viscous oil. Further purification of the viscous oil via HCl salt formation (HCl, MeOH) and preparative reverse-phase HPLC (method f) gave the TFA salt of Example 4b (19 mg) as a white solid. $^1$H-NMR (400 MHz, CDCl$_3$) δ ppm 7.33 (1 H, s), 6.57 (1 H, s), 4.55 (1 H, dd, J=14.94, 8.13 Hz), 4.35 (1 H, dd, J=14.94, 3.08 Hz), 3.79-3.88 (4 H, m, CH$_3$ and CH), 3.41 (2 H, d, J=10.99 Hz), 2.58-2.82 (5 H, m), 2.38 (3 H, s), 2.11 (1 H, td, J=12.14, 3.41 Hz), 1.92 (2 H, d, J=11.64 Hz), 1.57-1.82 (2 H, m).

Example 4c

N-(2-(4-Chloro-5-methyl-3-(trifluoromethyl)-1H-pyrazol-1-yl)-1-(1-(2,4-dichloro-5-methoxyphenyl)piperidin-4-yl)ethyl)acetamide

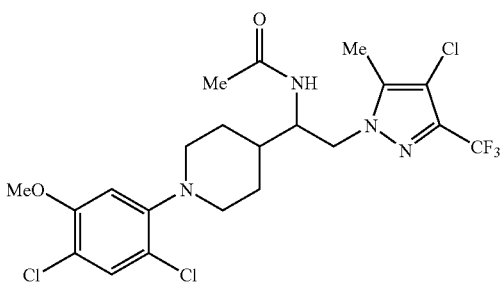

A 25-mL round bottom flask was charged with a solution of 2-(4-chloro-5-methyl-3-(trifluoromethyl)-1H-pyrazol-1-yl)-1-(1-(2,4-dichloro-5-methoxyphenyl)piperidin-4-yl)ethanamine (30 mg, 0.062 mmol) in anhydrous DCM (2 mL), triethylamine (0.086 mL, 0.618 mmol) and acetic anhydride (7.58 μL, 0.080 mmol). The reaction mixture was stirred at RT for 90 min, diluted with DCM (15 mL), and washed with sequentially with 1 M NaOH and brine. The resulting solution was dried (MgSO$_4$) and concentrated in vacuo. The resultant residue was purified by flash chromatography (4 g silica gel cartridge, EtOAc/hexanes) to afford Example 4c (18 mg, 0.034 mmol, 55% yield) as a white solid. $^1$H-NMR (400 MHz, CDCl$_3$) δ ppm 7.17 (1 H, s), 6.48 (1 H, s), 5.69 (1 H, d, J=8.13 Hz), 4.08-4.17 (1 H, m), 3.79 (3 H, s), 3.27-3.37 (2 H, m), 2.45-2.56 (2 H, m), 2.21-2.26 (3 H, m), 1.84 (3 H, s), 1.82-1.80 (1 H, d, J=11.42 Hz), 1.70 (1 H, d, J=9.67 Hz), 1.55 (1 H, s), 1.51 (1 H, d, J=10.33 Hz), 1.46 (3 H, s).

Example 4d 1-(2-(4-Chloro-5-methyl-3-(trifluoromethyl)-1H-pyrazol-1-371)-1-(1-(2,4-dichloro-5-methoxyphenyl)piperidin-4-yl)ethyl)urea

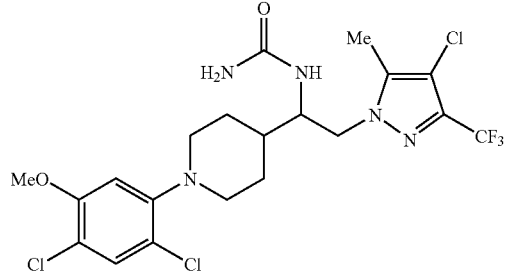 [SMILES: COc1cc(N2CCC(C(Cn3nc(C(F)(F)F)c(Cl)c3C)NC(N)=O)CC2)c(Cl)cc1Cl]

A solution of 2-(4-chloro-5-methyl-3-(trifluoromethyl)-1H-pyrazol-1-yl)-1-(1-(2,4-dichloro-5-methoxyphenyl)piperidin-4-yl)ethanamine (40 mg, 0.082 mmol) in anhydrous DCM (1 mL) was treated with trichloroacetyl isocyanate (0.015 mL, 0.124 mmol) and stirred at RT for 2 h. LC-MS indicated the formation of the trichloroacetyl urea intermediate (m/z=672). The mixture was concentrated on a rotary evaporator to yield a residue. The residue was dissolved in THF (2 mL) and the resultant solution was treated with 20% aqueous K$_2$CO$_3$ (2 mL). After stirring at RT for 2.5 h, the mixture was diluted with brine and extracted with EtOAc. The extract was dried (MgSO$_4$) and concentrated in vacuo. The resultant residue was purified by preparative HPLC (method f) to give Example 4d (19 mg, 0.036 mmol, 43% yield) as white solid. $^1$H-NMR (400 MHz, CDCl$_3$) δ ppm 7.09 (1 H, s), 6.40 (1 H, s), 5.92 (1 H, s), 3.98-4.09 (2 H, m), 3.72 (1 H, s), 3.67 (3 H, s), 3.20 (2 H, s), 2.37 (4 H, s), 2.10-2.15 (3 H, m), 1.66 (2 H, s), 1.38 (2 H, s).

Example 4e 1-(2-(4-Chloro-5-methyl-3-(trifluoromethyl)-1H-pyrazol-1-yl)-1-(1-(2,4-dichloro-5-methoxyphenyl)piperidin-4-yl)ethyl)-3-methylurea

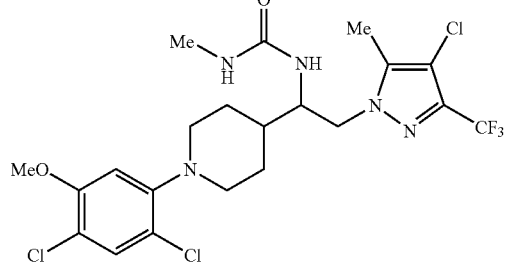

A screw-capped vial was charged with a solution of 2-(4-chloro-5-methyl-3-(trifluoromethyl)-1H-pyrazol-1-yl)-1-(1-(2,4-dichloro-5-methoxyphenyl)piperidin-4-yl)ethanamine (40 mg, 0.082 mmol) in anhydrous acetonitrile (1 mL), followed by methylisocyanate (11.74 mg, 0.206 mmol). The mixture was stirred at RT for 1 h before being concentrated in vacuo. The resultant residue was purified by preparative HPLC (method f) to give Example 4e (20 mg, 0.037 mmol, 44.7% yield) as a white solid. LC-MS: 542.2, (M+H); $t_R$=4.14 (method c).

Example 4f

N-(2-(4-Chloro-5-methyl-3-(trifluoromethyl)-1H-pyrazol-1-yl)-1-(1-(2,4-dichloro-5-methoxyphenyl)piperidin-4-yl)ethyl)thiazol-2-amine

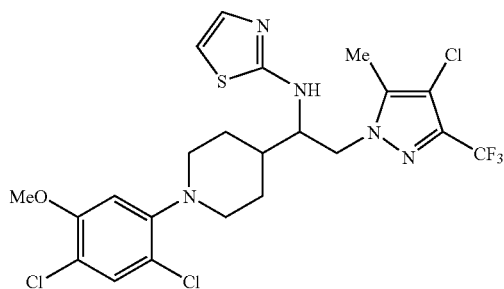 [SMILES: COc1cc(N2CCC(C(Cn3nc(C(F)(F)F)c(Cl)c3C)Nc3nccs3)CC2)c(Cl)cc1Cl]

A solution of 2-(4-chloro-5-methyl-3-(trifluoromethyl)-1H-pyrazol-1-yl)-1-(1-(2,4-dichloro-5-methoxyphenyl)piperidin-4-yl)ethanamine (48 mg, 0.099 mmol) in anhydrous acetone (1 mL) was treated with benzoyl isothiocyanate (0.015 mL, 0.109 mmol) and stirred at RT for 45 min; LC-MS showed the reaction was complete to give the benzoyl urea (m/z=648). The mixture was concentrated on a rotary evaporator to remove the solvent. The resultant residue was treated with 1 M NaOH (2 mL) and dioxane (1 mL), and the resultant solution was rapidly heated to 80° C. The mixture was stirred at 80° C. for 10 min, cooled to RT and then extracted with EtOAc. The extract was washed with 1M HCl and brine, dried (MgSO$_4$), and concentrated to give a pale-yellow solid. The pale-yellow solid was treated with EtOH (1.5 mL) and 45% chloroacetaldehyde (862 mg, 4.94 mmol) in water and stirred at 50° C. for 30 min. The mixture was concentrated and the resultant residue was partitioned between saturated NaHCO$_3$ and EtOAc. The organic phase was washed with brine, dried (MgSO$_4$) and concentrated on a rotary evaporator to give the crude product. The crude product was purified by preparative reverse phase HPLC (method f) to give Example 4f (19 mg, 0.033 mmol, 33% yield) as a white solid. $^1$H-NMR (400 MHz, CDCl$_3$) δ ppm 7.33 (1 H, s), 7.04 (1 H, d, J=3.74 Hz), 6.58 (1 H, s), 6.46 (1 H, d, J=3.52 Hz), 5.16 (1 H, d, J=7.03 Hz), 4.25-4.46 (2 H, m), 3.94-4.12 (1 H, m), 3.87 (3 H, s), 3.34-3.54 (2 H, m), 2.48-2.76 (2 H, m), 2.15-2.32 (3 H, m), 1.87-2.09 (2 H, m), 1.53-1.87 (2 H, m).

Example 4 g

N-(2-(4-Chloro-5-methyl-3-(trifluoromethyl)-1H-pyrazol-1-yl)-1-(1-(2,4-dichloro-5-methoxyphenyl)piperidin-4-yl)ethyl)methanesulfonamide

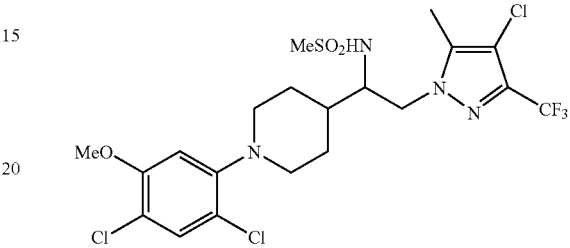

A 25-mL round bottom flask was charged with 2-(4-chloro-5-methyl-3-(trifluoromethyl)-1H-pyrazol-1-yl)-1-(1-(2,4-dichloro-5-methoxyphenyl)piperidin-4-yl)ethanamine (23 mg, 0.047 mmol), anhydrous DCM (2 mL), and triethylamine (0.016 mL, 0.118 mmol). The resultant solution was treated with methanesulfonyl chloride (5.50 μL, 0.071 mmol) and stirred at RT for 1 h. After this time, the mixture was concentrated on a rotary evaporator, and the resultant residue was partitioned between EtOAc and saturated sodium bicarbonate. The organic phase was washed with brine, dried (MgSO$_4$) and concentrated to give the crude product. The crude product was purified by flash chromatography (4 g silica gel cartridge, EtOAc/hexanes) to afford Example 4 g (22 mg, 0.039 mmol, 82% yield). LC-MS: 563.0 (M+H); $t_R$=4.18 min (method c). $^1$H-NMR (400 MHz, CDCl$_3$) δ ppm 7.16 (1 H, s), 6.49 (1 H, s), 4.59 (1 H, d, J=9.23 Hz), 4.20-4.26 (1 H, m), 4.09-4.15 (1 H, m), 3.76-3.81 (3 H, m), 3.59 (1 H, d, J=6.15 Hz), 3.30-3.39 (2 H, m), 2.65 (3 H, s), 2.48-2.54 (2 H, m), 2.23-2.32 (3 H, m), 1.91 (1 H, s), 1.75-1.81 (1 H, m), 1.55-1.62 (2 H, m).

Examples 4h to 4v

Examples 4h to 4v were made using the methods exemplified above in Examples 4c and 4g. As will be obvious to one skilled in the art, certain compounds (e.g. Examples 4h, 4o, 4s, 4u, and 4v) were purified by reverse phase HPLC rather than flash chromatography, and were isolated as their TFA salts. Data for Examples 4h to 4v are provided in Table 3 below. The substituents listed in each column are to be paired with the structure embedded in the table heading. The data in the "MS" column represent the values observed for the (M+H)$^+$ ions in electrospray mass spectroscopy experiments. For mass spectra in which multiple isotopes were observed, the major ion is listed. {Note: For compounds with one or two Cl atoms, this is typically the first ion of two significant ions; for compounds with three Cl atoms, this is typically the second ion of three significant ions.} The data in the "HPLC" column indicate the retention time with the method conditions shown in brackets.

TABLE 3

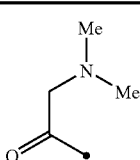

| Example | Name | R₁₂ | MS | HPLC t$_R$ (method) |
|---|---|---|---|---|
| 4h | N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-(dimethylamino)acetamide, TFA salt | 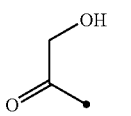 | 571.2 | 3.50 (c) |
| 4i | N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-hydroxyacetamide | 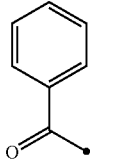 | 544.2 | 4.60 (c) |
| 4j | N-(2-(4-Chloro-5-methyl-3-(trifluoromethyl)-1H-pyrazol-1-yl)-1-(1-(2,4-dichloro-5-methoxyphenyl)piperidin-4-yl)ethyl)benzamide | 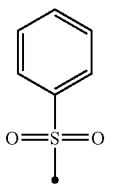 | 590.2 | 4.30 (c) |
| 4k | N-(2-(4-Chloro-5-methyl-3-(trifluoromethyl)-1H-pyrazol-1-yl)-1-(1-(2,4-dichloro-5-methoxyphenyl)piperidin-4-yl)ethyl)benzenesulfonamide | 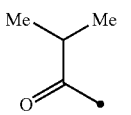 | 625.2 | 4.35 (c) |
| 4l | N-(2-(4-Chloro-5-methyl-3-(trifluoromethyl)-1H-pyrazol-1-yl)-1-(1-(2,4-dichloro-5-methoxyphenyl)piperidin-4-yl)ethyl)isobutyramide | 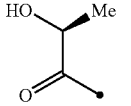 | 555.2 | 4.25 (c) |
| 4m | (2S)-N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-hydroxypropanamide | 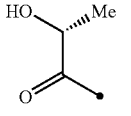 | 557.0 | 4.04 (c) |
| 4n | (2R)-N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-hydroxypropanamide | 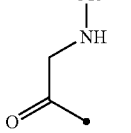 | 557.0 | 4.04 (c) |
| 4o | N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-(methylamino)acetamide, TFA salt | | 556.1 | 3.52 (c) |

TABLE 3-continued

| Example | Name | R$_{12}$ | MS | HPLC t$_R$ (method) |
|---|---|---|---|---|
| 4p | N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-fluoroacetamide | -C(O)CH$_2$F | 545.1 | 4.08 (c) |
| 4q | N-(2-(4-Chloro-5-methyl-3-(trifluoromethyl)-1H-pyrazol-1-yl)-1-(1-(2,4-dichloro-5-methoxyphenyl)piperidin-4-yl)ethyl)propionamide | -C(O)CH$_2$Me | 541.1 | 4.16 (c) |
| 4r | N-(2-(4-Chloro-5-methyl-3-(trifluoromethyl)-1H-pyrazol-1-yl)-1-(1-(2,4-dichloro-5-methoxyphenyl)piperidin-4-yl)ethyl)butyramide | -C(O)CH$_2$CH$_2$Me | 555.1 | 4.23 (c) |
| 4s | 2-Amino-N-(2-(4-chloro-5-methyl-3-(trifluoromethyl)-1H-pyrazol-1-yl)-1-(1-(2,4-dichloro-5-methoxyphenyl)piperidin-4-yl)ethyl)acetamide, TFA salt | -C(O)CH$_2$NH$_2$ | 542.1 | 3.54 (c) |
| 4t | N-(2-(4-Chloro-5-methyl-3-(trifluoromethyl)-1H-pyrazol-1-yl)-1-(1-(2,4-dichloro-5-methoxyphenyl)piperidin-4-yl)ethyl)cyclopropanecarboxamide | -C(O)-cyclopropyl | 553.1 | 4.19 (c) |
| 4u | (2S)-2-Amino-N-(2-(4-chloro-5-methyl-3-(trifluoromethyl)-1H-pyrazol-1-yl)-1-(1-(2,4-dichloro-5-methoxyphenyl)piperidin-4-yl)ethyl)-3-hydroxypropanamide, TFA salt | -C(O)CH(NH$_2$)CH$_2$OH (S) | 572.1 | 3.52 (c) 3.62 (c) |
| 4v | (2S)-2-Amino-N-(2-(4-chloro-5-methyl-3-(trifluoromethyl)-1H-pyrazol-1-yl)-1-(1-(2,4-dichloro-5-methoxyphenyl)piperidin-4-yl)ethyl)-3-hydroxypropanamide, TFA salt | -C(O)CH(NH$_2$)CH$_2$OH (S) | 572.1 | 3.52 (c) 3.62 (c) |

Example 5a

N-(1-(1-(4-Chloro-3-methoxyphenyl)piperidin-4-yl)-2-(5-methyl-3-(trifluoromethyl)-1H-pyrazol-1-yl)ethyl)acetamide and separation into its two enantiomers

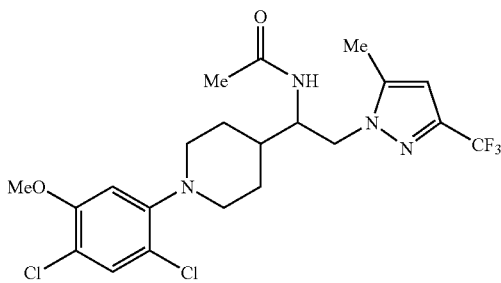 [SMILES: COc1cc(N2CCC(C(Cn3nc(C(F)(F)F)cc3C)NC(C)=O)CC2)c(Cl)cc1Cl]

Step 1: A mixture of 2-chloro-1-(1-(4-chloro-3-methoxyphenyl)piperidin-4-yl)ethanone (580 mg, 1.919 mmol; see Example 1a, Step 2), 5-methyl-3-(trifluoromethyl)-1H-pyrazole (576 mg, 3.84 mmol), potassium carbonate (796 mg, 5.76 mmol) and acetonitrile (20 mL) was stirred at RT for 12 h. After this time, the solvent was removed under reduced pressure and the resultant residue was partitioned between EtOAc (100 mL) and water (50 mL). The organic phase was washed with brine, dried ($Na_2SO_4$) and concentrated on a rotary evaporator to yield a residue. The residue was purified by flash chromatography using a 40 g silica gel cartridge and gradient elution from 10:1 Hex/EtOAc to 1:1 Hex/EtOAc. The fractions containing the product were pooled and concentrated on a rotary evaporator to give 1-(1-(4-chloro-3-methoxyphenyl)piperidin-4-yl)-2-(5-methyl-3-(trifluoromethyl)-1H-pyrazol-1-yl)ethanone (650 mg, 1.563 mmol, 81% yield) as clear oil. $^1$H-NMR (400 MHz, CDCl$_3$) δ ppm 7.19 (1 H, d, J=8.57 Hz), 6.49 (1 H, d, J=2.42 Hz), 6.44 (1 H, dd, J=8.68, 2.53 Hz), 6.35 (1 H, s), 5.01-5.04 (2 H, m), 3.84-3.89 (3 H, m), 3.62-3.69 (2 H, m), 2.77 (2 H, td, J=12.03, 2.75 Hz), 2.58 (1 H, tt, J=11.29, 3.87 Hz), 2.21 (3 H, s), 1.99 (2 H, s), 1.80-1.91 (2 H, m).

Step 2: A mixture of 1-(1-(4-chloro-3-methoxyphenyl)piperidin-4-yl)-2-(5-methyl-3-(trifluoromethyl)-1H-pyrazol-1-yl)ethanone (941 mg, 2.263 mmol), ammonia (5.7 mL of a 2.0 M solution in EtOH, 11.31 mmol) and titanium(IV) isopropoxide (1.34 mL, 4.53 mmol) was stirred at RT in a tightly stoppered flask for 16 h. At the conclusion of this period, the mixture was treated with anhydrous 1,2-DCE (2 mL), cooled in an ice bath and then treated with sodium borohydride (128 mg, 3.39 mmol) in portions. After 45 min, the mixture had changed to a thick foamy mixture. As a result, 1,2-DCE (3 mL) was added to facilitate stirring and the reaction was stirred for an additional 2 h. After this time, the mixture was poured into aqueous concentrated NH$_4$OH (5 mL), diluted with CH$_2$Cl$_2$ (115 mL) and stirred vigorously for 30 min before being filtered through Celite. The filtrate was placed in a separatory funnel and the phases separated. The aqueous phase was extracted with CH$_2$Cl$_2$ (3 times). The combined extracts were washed with brine, dried (MgSO$_4$) and concentrated to give the crude product. The crude product was purified by flash chromatography on silica gel using EtOAc and 5% MeOH/CH$_2$Cl$_2$ as eluents to provide 1-(1-(4-chloro-3-methoxyphenyl)piperidin-4-yl)-2-(5-methyl-3-(trifluoromethyl)-1H-pyrazol-1-yl)ethanamine (490 mg, 1.175 mmol, 51.9% yield) as a pale yellow solid. $^1$H-NMR (400 MHz, CDCl$_3$) δ ppm 7.18 (1 H, d, J=8.79 Hz), 6.50 (1 H, d, J=2.42 Hz), 6.41-6.47 (1 H, m), 6.30 (1 H, s), 4.22 (1 H, dd, J=13.84, 3.52 Hz), 3.91-3.99 (1 H, m), 3.87 (3 H, s), 3.69 (2 H, d, J=8.57 Hz), 3.22-3.28 (1 H, m), 2.65-2.75 (2 H, m), 2.33 (3 H, s), 1.89-1.98 (1 H, m), 1.84 (1 H, d, J=9.67 Hz), 1.53-1.63 (3 H, m).

Step 3: A 25-mL round bottom flask was charged with a solution of 1-(1-(4-chloro-3-methoxyphenyl)piperidin-4-yl)-2-(5-methyl-3-(trifluoromethyl)-1H-pyrazol-1-yl)ethanamine (120 mg, 0.288 mmol) in anhydrous DCM (2 mL). The mixture was treated sequentially with triethylamine (401 μL, 2.88 mmol) and acetic anhydride (35.3 μL, 0.374 mmol) before being stirred at RT for 90 min. After this time, the mixture was diluted with DCM (15 mL) and then washed with 1 M NaOH and brine. The extracts were dried (MgSO$_4$) and concentrated in vacuo to give the crude product, which was purified by flash chromatography (4 g silica gel cartridge, EtOAc/hexanes) to yield racemic Example 5a (90 mg).

Step 4: Racemic Example 5a was separated into two pure enantiomers by chiral HPLC using a Berger SFC MGIII system and the following conditions: Chiral AD 25×3 cm ID, 5 μm; Flow rate, 140 mL/min; Mobile Phase, 70/30 CO$_2$/MeOH; detector wavelength, 220 nm. On analytical HPLC, the first enantiomer and second enantiomer exhibited retention times of 2.28 min and 5.36 min, respectively (Chiral AD 250×4.6 mm ID, 5 micron; Flow rate, 2.0 mL/min; Mobile Phase, 65/35 CO$_2$/MeOH). The NMR and LC/MS (achiral column) were identical for the two enantiomers. LC/MS 459.19 [M+H]$^+$, $t_R$=2.65 min (method b). $^1$H-NMR (400 MHz, CDCl$_3$) δ ppm 7.19 (1 H, d, J=8.57 Hz), 6.48 (1 H, d, J=19.99 Hz), 6.29 (1 H, s), 5.94 (1 H, s), 4.12-4.31 (3 H, m), 3.87 (3 H, s), 3.65 (2 H, t, J=10.44 Hz), 2.69 (2 H, d, J=2.86 Hz), 2.34 (3 H, s), 1.90 (4 H, m), 1.79 (1 H, d, J=11.86 Hz), 1.29-1.75 (4 H, m).

Examples 5b to 5d

Examples 5b to 5d were prepared using the methods exemplified above in Example 5a. Data for Examples 5b to 5d are provided in Table 4 below. The substituents listed in each column are to be paired with the structure embedded in the table heading. In the synthesis of the examples, substitutions for key reagents were made in Step 3 of the procedure outlined in Example 5a, as will be evident to one skilled in the art. The data in the "MS" column represent the values observed for the (M+H)$^+$ ions in electrospray mass spectroscopy experiments. For mass spectra in which multiple isotopes were observed, the major ion is listed. {Note: For compounds with one or two Cl atoms, this is typically the first ion of two significant ions; for compounds with three Cl atoms, this is typically the second ion of three significant ions.} For Table 4, "HPLC $t_R$" indicates the retention time for the two enantiomers (or diastereomers, in the case of example 5d) under the following HPLC conditions: Berger SFC system, Chiral AD 250×4.6 mm ID, 5 μm; 2.0 mL/min flow rate; 65/35 CO$_2$/MeOH mobile phase. These enantiomers were separated according to the procedure outlined in the synthesis of Example 5a.

TABLE 4

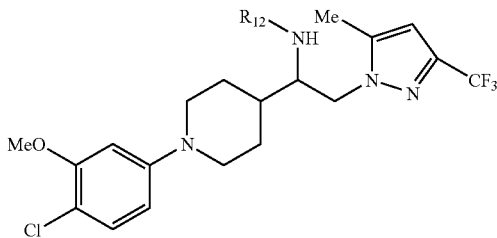

| Example | Name | R$_{12}$ | MS | HPLC t$_R$ |
|---|---|---|---|---|
| 5b | N-(1-(1-(4-chloro-3-methoxyphenyl)piperidin-4-yl)-2-(5-methyl-3-(trifluoromethyl)-1H-pyrazol-1-yl)ethyl)-2-hydroxyacetamide (enantiomers 1 & 2) | -C(O)CH$_2$OH | 441.3 | 2.65, 3.60 |
| 5c | 2-amino-N-(1-(1-(4-chloro-3-methoxyphenyl)piperidin-4-yl)-2-(5-methyl-3-(trifluoromethyl)-1H-pyrazol-1-yl)ethyl)acetamide (enantiomers 1 & 2) | -C(O)CH$_2$NH$_2$ | 474.4 | 2.59, 3.67 |
| 5d | (R)-N-(1-(1-(4-chloro-3-methoxyphenyl)piperidin-4-yl)-2-(5-methyl-3-(trifluoromethyl)-1H-pyrazol-1-yl)ethyl)-2-hydroxypropanamide (diastereomers 1 & 2) | -C(O)CH(OH)Me | 489.1 | 2.59, 3.68 |

Example 6

4-(2-((4-Chloro-5-methyl-3-(trifluoromethyl)-1H-pyrazol-1-yl)methyl)-1,3-dioxolan-2-yl)-1-(2,4-dichloro-5-methoxyphenyl)piperidine

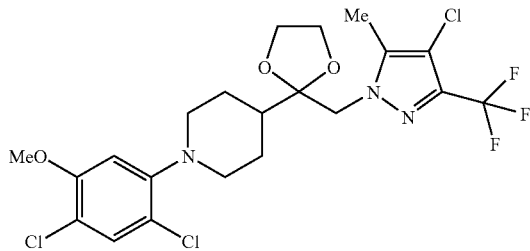 [SMILES: COc1cc(N2CCC(C3(Cn4nc(C(F)(F)F)c(Cl)c4C)OCCO3)CC2)c(Cl)cc1Cl]

A mixture of 2-(4-chloro-5-methyl-3-(trifluoromethyl)-1H-pyrazol-1-yl)-1-(1-(2,4-dichloro-5-methoxyphenyl)piperidin-4-yl)ethanone (55 mg, 0.113 mmol), anhydrous ethylene glycol (4 mL, 71.8 mmol), p-toluenesulfonic acid monohydrate (3 mg, 0.016 mmol) and anhydrous MgSO$_4$ (20 mg) was stirred under nitrogen at 140° C. for 12 h. After this time, the mixture was cooled to RT, treated with saturated NaHCO$_3$ and then extracted with EtOAc. The extract was washed several times with water and brine, dried (MgSO$_4$) and concentrated on a rotary evaporator to yield a residue. The residue was purified by flash chromatography using a 4 g silica gel cartridge and gradient elution from 10:1 EtOAc/Hex to 3:1 EtOAc/Hex. The fractions containing the product were pooled and concentrated on a rotary evaporator to give Example 6 (25 mg, 0.047 mmol, 42% yield) as a pale yellow crystalline solid. LC-MS: 528.9, (M+H), t$_R$=4.48 min (method c). $^1$H-NMR (400 MHz, CDCl$_3$) δ ppm 7.15 (1 H, s), 6.51 (1 H, s), 4.16 (3 H, s), 3.69-3.88 (6 H, m), 3.38 (4 H, m), 2.49 (1 H, m), 2.22 (3 H, s), 1.86 (2 H, d, J=5.71 Hz), 1.64 (2 H, s).

Example 7

2-(4-Chloro-5-methyl-3-(trifluoromethyl)-1H-pyrazol-1-yl)-1-(1-(2,4-dichloro-5-ethoxyphenyl)piperidin-4-yl)ethanol

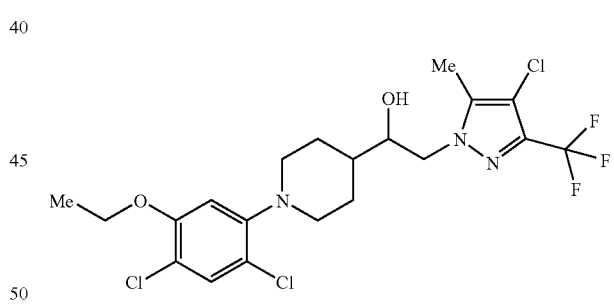

Step 1: A solution of 2-(4-chloro-5-methyl-3-(trifluoromethyl)-1H-pyrazol-1-yl)-1-(1-(2,4-dichloro-5-methoxyphenyl)piperidin-4-yl)ethanone (100 mg, 0.206 mmol) in anhydrous DCM (1.5 mL) was cooled to −78° C. and then treated with boron tribromide (0.619 mL of a 1.0 M solution in heptanes, 0.619 mmol). The mixture was stirred for 30 min and the cooling bath was removed so that the reaction could warm to RT. After 3 h at RT, the reaction was poured unto crushed ice and extracted with DCM. The extract was dried (MgSO$_4$) and concentrated on a rotary evaporator to give 2-(4-chloro-5-methyl-3-(trifluoromethyl)-1H-pyrazol-1-yl)-1-(1-(2,4-dichloro-5-hydroxyphenyl)piperidin-4-yl)ethanone (80 mg, 0.170 mmol, 82% yield) as a pale yellow solid. LC-MS: 470.13, [M+H]; t$_R$=2.10 min (method a).

Step 2: A mixture of 2-(4-chloro-5-methyl-3-(trifluoromethyl)-1H-pyrazol-1-yl)-1-(1-(2,4-dichloro-5-hydroxyphenyl)piperidin-4-yl)ethanone (30 mg, 0.064 mmol), cesium carbonate (41.5 mg, 0.127 mmol) and acetonitrile (1.5 mL) was treated with bromoethane (0.024 mL, 0.319 mmol) and heated at 50° C. for 2 h. The mixture was concentrated and the resultant residue was partitioned between EtOAc and sat. NaHCO$_3$. The organic phase was washed with brine, dried (Na$_2$SO$_4$) and concentrated to give the crude product (32 mg). The crude product was dissolved in DCM (2 mL) and MeOH (0.9 mL), treated with sodium borohydride (4.82 mg, 0.127 mmol) and stirred at RT for 30 min. After this time, the mixture was diluted with DCM (10 mL), washed with sat. NaHCO$_3$ and brine, dried (Na$_2$SO$_4$), and concentrated in vacuo. The resultant crude product was purified by preparative HPLC (method f) to give Example 7 (9 mg, 0.018 mmol, 28% yield) as a white solid. $^1$H-NMR (400 MHz, CD$_3$OD) δ ppm 7.25 (1 H, s), 6.68 (1 H, s), 4.12-4.18 (1 H, m), 4.04-4.09 (1 H, m), 4.00 (2 H, q, J=6.96 Hz), 3.70 (1 H, ddd, J=8.68, 5.60, 3.30 Hz), 3.33 (2 H, d, J=11.64 Hz), 3.20 (1 H, d, J=1.76 Hz), 2.56-2.66 (2 H, m), 2.24-2.29 (3 H, m), 1.87 (1 H, d, J=11.64 Hz), 1.76 (1 H, d, J=12.08 Hz), 1.62 (1 H, td, J=11.64, 3.52 Hz), 1.46-1.57 (2 H, m), 1.30-1.36 (3 H, m).

Example 8

2-(4-Chloro-5-methyl-3-(trifluoromethyl)-1H-pyrazol-1-yl)-1-(1-(2,4-dichloro-5-isopropoxyphenyl)piperidin-4-yl)ethanol

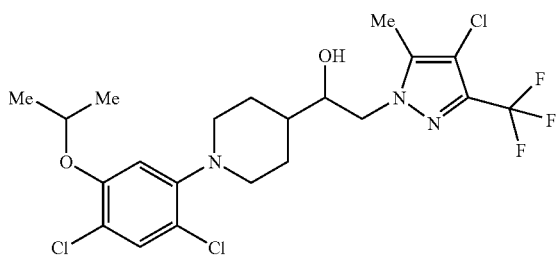 [SMILES: Cc1c(Cl)c(C(F)(F)F)nn1CC(O)C1CCN(c2cc(OC(C)C)c(Cl)cc2Cl)CC1]

Step 1: A solution of 2-(4-chloro-5-methyl-3-(trifluoromethyl)-1H-pyrazol-1-yl)-1-(1-(2,4-dichloro-5-hydroxyphenyl)piperidin-4-yl)ethanone (30 mg, 0.064 mmol) in anhydrous acetonitrile (1.5 mL) was treated with 2-iodopropane (0.019 mL, 0.191 mmol) and cesium carbonate (41.5 mg, 0.127 mmol) and the mixture stirred at 50° C. for 1 h. After this time, the mixture was concentrated on a rotary evaporator and the resultant residue was partitioned between water and EtOAc. The EtOAc phase was washed with brine, dried (MgSO$_4$) and concentrated to give 2-(4-chloro-5-methyl-3-(trifluoromethyl)-1H-pyrazol-1-yl)-1-(1-(2,4-dichloro-5-isopropoxyphenyl)piperidin-4-yl)ethanone. LC-MS: 512.20, [M+H]; t$_R$=2.30 min (method a).

Step 2: A solution of 2-(4-chloro-5-methyl-3-(trifluoromethyl)-1H-pyrazol-1-yl)-1-(1-(2,4-dichloro-5-isopropoxyphenyl)piperidin-4-yl)ethanone in DCM (1.5 mL) and MeOH (0.5 mL) was treated with sodium borohydride (4.82 mg, 0.127 mmol) and the mixture was stirred at RT for 1 h. At the conclusion of this period, the mixture was treated with acetone (1 mL) and stirred for 10 min to consume the excess reducing agent and then concentrated on a rotary evaporator to give the crude product. The crude product was purified by preparative HPLC (method f) to give Example 8 (6 mg, 18%) as a white solid. LC-MS: 514.20, [M+H]; t$_R$=4.35 min (method f). $^1$H-NMR (400 MHz, CDCl$_3$) δ ppm 7.36 (1 H, s), 6.60 (1 H, s), 4.54 (1 H, s), 4.21 (1 H, d, J=12.96 Hz), 3.89-4.13 (3 H, m), 3.33-3.60 (3 H, m), 2.23-2.34 (4 H, m), 2.00 (2 H, s), 1.88 (2 H, s), 1.37 (6 H, d, J=5.93 Hz).

Example 9

2-(4-Chloro-5-methyl-3-(trifluoromethyl)-1H-pyrazol-1-yl)-1-(1-(2,4-dichloro-5-(2-hydroxyethoxy)phenyl)piperidin-4-yl)ethanol

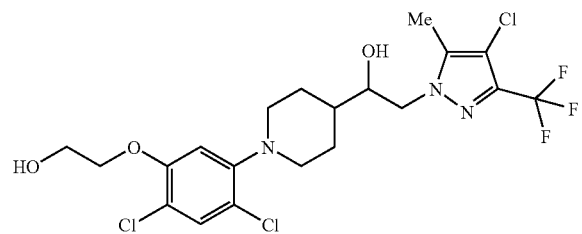 [SMILES: Cc1c(Cl)c(C(F)(F)F)nn1CC(O)C1CCN(c2cc(OCCO)c(Cl)cc2Cl)CC1]

Ethylene oxide (0.016 mL, 0.319 mmol) was bubbled through a mixture of 2-(4-chloro-5-methyl-3-(trifluoromethyl)-1H-pyrazol-1-yl)-1-(1-(2,4-dichloro-5-hydroxyphenyl)piperidin-4-yl)ethanone (30 mg, 0.064 mmol), cesium carbonate (62.3 mg, 0.191 mmol) and acetonitrile (3 mL) in a screw-cap vial for 1 min. The vial was capped and then heated at 50° C. for 1 h. After this time, the mixture was concentrated and the resultant residue was partitioned between EtOAc and brine. The organic phase was dried (Na$_2$SO$_4$) and concentrated on a rotary evaporator to give the crude ketone product. The crude ketone product was dissolved in DCM (2 mL) and MeOH (0.3 mL) and then treated with sodium borohydride (4.82 mg, 0.127 mmol). The mixture was stirred at RT for 1 h, diluted with DCM (10 mL), washed with brine, dried (Na$_2$SO$_4$) and concentrated. The resultant crude product was purified by preparative HPLC (method f) to give Example 9 (12 mg, 0.023 mmol, 36.4% yield) as white solid after lyophilization. LC-MS 516.17, [M+H]; t$_R$=4.00 min (method f). $^1$H-NMR (400 MHz, CD$_3$OD) δ ppm 7.27 (1 H, s), 6.77 (1 H, s), 3.94-4.22 (4 H, m), 3.80 (2 H, t, J=4.72 Hz), 3.65-3.75 (1 H, m), 3.35 (2 H, d, J=11.64 Hz), 2.56-2.73 (2 H, m), 2.26 (3 H, s), 1.83 (2 H, app. dd, J=43.2, 11.5 Hz), 1.38-1.70 (3 H, m).

Example 10

4-(1-(4-Chloro-5-methyl-3-(trifluoromethyl)-1H-pyrazol-1-yl)propan-2-yl)-1-(2,4-dichloro-5-methoxyphenyl)piperidine

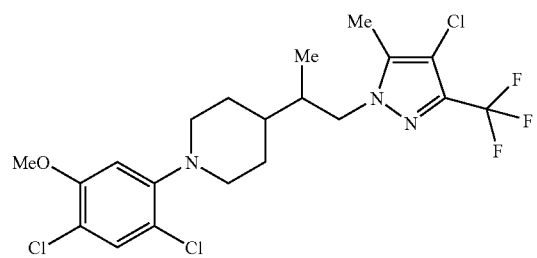 [SMILES: COc1cc(N2CCC(C(C)Cn3nc(C(F)(F)F)c(Cl)c3C)CC2)c(Cl)cc1Cl]

Step 1: A 100-mL 3-neck round-bottom flask was charged with anhydrous THF (20 mL) and 60% dispersion sodium hydride (0.574 g, 14.35 mmol) and placed under nitrogen atmosphere. At ambient temperature, ethyl 2-(diethoxyphosphoryl)propanoate (3.42 g, 14.35 mmol) was added to the suspension via syringe over a period of 5 min and the mixture stirred for 30 min. The resulting clear mixture was treated with a solution of tert-butyl 4-oxopiperidine-1-carboxylate (2.2 g, 11.04 mmol) in anhydrous THF (5 mL) and the reaction continued at ambient temperature for 1 h. At the conclusion of this period, the mixture was quenched with saturated NH$_4$Cl solution and the mixture was then extracted with EtOAc (3×50 mL). The extract was washed with brine, dried (MgSO$_4$) and concentrated to give the crude product. The crude product was purified by flash chromatography using an 80 g silica gel gradient elution from 20:1 Hex/EtOAc to 6:1 Hex/EtOAc. The fractions containing the product were pooled and concentrated on a rotary evaporator to give tert-butyl 4-(1-ethoxy-1-oxopropan-2-ylidene)piperidine-1-carboxylate as a colorless liquid. $^1$H-NMR (500 MHz, CDCl$_3$) δ ppm 4.18 (2 H, q, J=7.15 Hz), 3.43 (4 H, dt, J=23.71, 5.88 Hz), 2.61 (2 H, t, J=5.77 Hz), 2.33 (2 H, t, J=5.77 Hz), 1.86 (3 H, s), 1.45 (9H, s), 1.26-1.31 (3H, m, J=7.15 Hz).

Step 2: The product from Step 1 above was dissolved in absolute EtOH (10 mL) and hydrogenated over Pt$_2$O (150 mg) for 14 h. After this time, the reaction was filtered to remove the catalyst and concentrated on a rotary evaporator to give tert-butyl 4-(1-ethoxy-1-oxopropan-2-yl)piperidine-1-carboxylate (1.5 g, 5.26 mmol, 47.6% yield, 2 steps) as a colorless liquid. $^1$H-NMR (400 MHz, CDCl$_3$) δ ppm 4.03-4.15 (4 H, m), 2.63 (2 H, t, J=11.58 Hz), 2.18-2.26 (1 H, m, J=7.18, 7.18, 7.18, 7.18 Hz), 1.59-1.70 (2 H, m), 1.47-1.57 (1 H, m), 1.41 (9 H, s), 1.22 (3 H, t, J=7.18 Hz), 1.24-1.18 (m, 2 H), 1.14 (1 H, dd, J=13.22, 4.41 Hz), 1.09 (3 H, d, J=7.05 Hz).

Step 3: A sample of tert-butyl 4-(1-ethoxy-1-oxopropan-2-yl)piperidine-1-carboxylate (1.4 g, 4.91 mmol) was dissolved in 4 M hydrogen chloride/dioxane (5 mL, 165 mmol) and stirred at RT for 2 h. At the conclusion of this period, the mixture was concentrated on a rotary evaporator and the resultant residue was treated with saturated NaHCO$_3$ and then 1 M NaOH to bring the pH to 9. The mixture was extracted with EtOAc. The extract was washed with brine, dried (MgSO$_4$) and concentrated to give ethyl 2-(piperidin-4-yl)propanoate (0.85 g, 93%). $^1$H-NMR (400 MHz, CDCl$_3$) δ ppm 4.05-4.13 (2 H, m), 2.99-3.08 (2 H, m), 2.54 (2 H, td, J=12.09, 2.52 Hz), 2.16-2.25 (1 H, m), 1.75 (1 H, s), 1.57-1.66 (2 H, m), 1.52 (1 H, dt, J=12.90, 2.86 Hz), 1.09-1.22 (1 H, m), 1.21 (3 H, t, J=7.18 Hz), 1.07 (3 H, d, J=7.05 Hz).

Step 4: A 25-mL round-bottom flask was charged with ethyl 2-(piperidin-4-yl)propanoate (220 mg, 1.187 mmol) and anhydrous toluene (4 mL) and the flask purged of air and back-filled with nitrogen. The solution was treated with rac-2,2-bis(diphenylphosphino)-1,1-binaphthyl (148 mg, 0.237 mmol), tris(dibenzylideneacetone)dipalladium(0) (109 mg, 0.119 mmol) and sodium tert-butoxide (114 mg, 1.187 mmol) and then heated at 112° C. for 14 h. After this time, the mixture was cooled to RT, diluted with saturated NaHCO$_3$ (15 mL) and extracted with EtOAc. The extract was washed with brine, dried (MgSO$_4$) and concentrated on a rotary evaporator. The resultant residue was purified by flash chromatography using a 12 g silica gel cartridge and gradient elution from 20:1 Hex/EtOAc to 3:1 Hex/EtOAc. The fractions containing the product were pooled and concentrated on a rotary evaporator to give ethyl 2-(1-(4-chloro-3-methoxyphenyl)piperidin-4-yl)propanoate (133 mg, 0.408 mmol, 34.4% yield). $^1$H-NMR (400 MHz, CDCl$_3$) δ ppm 7.17 (1 H, d, J=8.81 Hz), 6.49 (1 H, d, J=2.52 Hz), 6.43 (1 H, dd, J=8.69, 2.64 Hz), 4.14 (2 H, q, J=7.05 Hz), 3.87 (3 H, s), 3.59-3.69 (2 H, m), 2.68 (2 H, td, J=12.21, 2.52 Hz), 2.26-2.34 (1 H, m, J=7.11, 7.11, 7.11, 7.11 Hz), 1.81 (1 H, dt, J=12.78, 2.80 Hz), 1.64-1.74 (2 H, m), 1.38-1.49 (2 H, m), 1.26 (3 H, t, J=7.05 Hz), 1.15 (3 H, d, J=7.05 Hz).

Step 5: A sample of ethyl 2-(1-(4-chloro-3-methoxyphenyl)piperidin-4-yl)propanoate (130 mg, 0.359 mmol) was suspended in glacial AcOH (4 mL) and water (0.5 mL). The resultant solution was treated with N-chlorosuccinimide (62.3 mg, 0.467 mmol) and then stirred at RT overnight. After this time, the mixture was diluted with water (10 mL) and Et$_2$O (25 mL) and the pH was adjusted to pH 9 using 6 M NaOH (aq). The phases were separated and the aqueous phase was extracted with Et$_2$O. The extracts were combined, washed with brine, dried (MgSO$_4$) and concentrated on a rotary evaporator. The resultant residue was purified by flash chromatography using a 12 g silica gel cartridge and gradient elution from 10:1 Hex/EtOAc to 5:1 Hex/EtOAc. The fractions containing the product were pooled and concentrated on a rotary evaporator to give ethyl 2-(1-(2,4-dichloro-5-methoxyphenyl)piperidin-4-yl)propanoate (80 mg, 0.222 mmol, 62% yield) as an oil. $^1$H-NMR (500 MHz, CDCl$_3$) δ ppm 7.32 (1 H, s), 6.58 (1 H, s), 4.15 (2 H, qd, J=7.06, 1.92 Hz), 3.87 (3 H, s), 3.34-3.41 (2 H, m), 2.60 (2 H, t, J=11.55 Hz), 2.33 (1 H, dt, J=14.30, 7.15 Hz), 1.81 (1 H, dt, J=12.92, 2.61 Hz), 1.65-1.73 (2 H, m), 1.44-1.62 (2 H, m), 1.27 (3 H, t, J=7.15 Hz), 1.16 (3 H, d, J=7.15 Hz). LC-MS: 360, [M+H]; t$_R$=4.28 min (method b).

Step 6: A solution of ethyl 2-(1-(2,4-dichloro-5-methoxyphenyl)piperidin-4-yl)propanoate (94 mg, 0.26 mmol) in anhydrous THF (2.0 mL) was placed under nitrogen atmosphere, cooled to −10° C., and treated with DIBAL-H (0.780 mL of a 1.0 M solution in THF, 0.780 mmol). After 30 min, the cooling bath was removed and the reaction warmed to RT where it stirred for 2 h. After this time, the mixture was quenched by adding EtOAc (3 mL) and stirred vigorously for 20 min. The pH of the mixture was adjusted to pH 6 using 1 M HCl. Once at the prescribed pH, EtOAc (20 mL) was added and the mixture was stirred at RT overnight. At the conclusion of this period, the organic phase was separated, washed with brine, dried (MgSO$_4$) and concentrated to give 2-(1-(2,4-dichloro-5-methoxyphenyl)piperidin-4-yl)propan-1-ol (88 mg, 0.277 mmol, quantitative) as a yellow oil. LC-MS: 318.19, [M+H]; t$_R$=3.89 min (method b). $^1$H-NMR (400 MHz, CDCl$_3$) δ ppm 7.32 (1 H, s), 6.59 (1 H, s), 3.87 (3 H, s), 3.62-3.69 (1 H, m), 3.52-3.59 (1 H, m), 3.36-3.44 (2 H, m), 2.53-2.63 (2 H, m), 1.70-1.78 (2 H, m), 1.54-1.62 (3 H, m), 1.49-1.53 (1 H, m), 0.96 (3 H, d, J=6.80 Hz).

Step 7: A solution of 2-(1-(2,4-dichloro-5-methoxyphenyl)piperidin-4-yl)propan-1-ol (88 mg, 0.277 mmol) in CH$_2$Cl$_2$ (3.0 mL) and pyridine (1 mL, 12.36 mmol) was cooled in an ice-water bath and treated with p-toluenesulfonyl chloride (79 mg, 0.415 mmol). The mixture was stirred for 15 min and then the cooling bath removed. The reaction was stirred for 12 h at RT and treated with cold saturated NaHCO$_3$. The resultant mixture was extracted with DCM. The extract was dried (MgSO$_4$) and concentrated to give the crude tosylate, which was used without additional purification. LC-MS (m/z=472).

Step 8: A solution of the crude tosylate from Step 7 (66.1 mg, 0.14 mmol) in DMF (0.5 mL) was added to a stirring mixture of 4-chloro-5-methyl-3-(trifluoromethyl)-1H-pyrazole (51.7 mg, 0.280 mmol), anhydrous cesium carbonate (137 mg, 0.420 mmol), and anhydrous DMF (2 mL). The resultant mixture was stirred at RT for 5 minutes then heated at 90° C. for 45 min. After cooling to RT, the mixture was partitioned between EtOAc (20 mL) and water (10 mL). The organic phase was washed with water, 10% LiCl, brine, dried (MgSO$_4$) and concentrated to give the crude product. The crude product was purified by preparative HPLC (method f)

to afford Example 10 as an amber solid after lypholization (15 mg, 0.025 mmol, 17.89% yield). LC-MS: 484.1, (M+H); $t_R$=4.79 min (method c). $^1$H-NMR (400 MHz, CDCl$_3$) δ ppm 7.37 (1 H, s), 6.84 (1 H, br. s), 4.07-4.17 (1 H, m), 3.85-3.93 (4 H, m), 3.44-3.52 (3 H, m), 2.28 (4 H, 4, CH$_3$ and CH), 2.05-2.17 (1 H, m), 1.69-1.89 (4 H, m), 1.38-1.47 (1 H, m), 0.88 (3 H, d, J=7.03 Hz).

Example 11

1-(1-(4-Chloro-3-methoxyphenyl)-4-methylpiperidin-4-yl)-2-(4-chloro-5-methyl-3-(trifluoromethyl)-1H-pyrazol-1-yl)ethanol

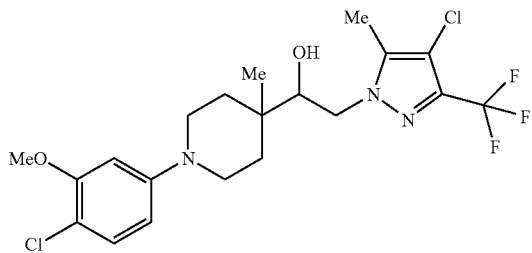 [SMILES: COc1cc(N2CCC(C)(C(O)Cn3nc(C(F)(F)F)c(Cl)c3C)CC2)ccc1Cl]

Step 1: Methyl 1-(4-chloro-3-methoxyphenyl)piperidine-4-carboxylate was synthesized from 4-bromo-1-chloro-2-methoxybenzene and methyl piperidine-4-carboxylate analogous to the preparation described in Example 1a, Step 1. $^1$H-NMR (500 MHz, CDCl$_3$) δ ppm 7.19 (1 H, d, J=8.57 Hz), 6.51 (1 H, s), 6.44 (1 H, s), 5.82 (1 H,), 3.85-3.88 (3 H, m), 3.70-3.72 (3 H, m), 3.33 (2 H, d, J=11.55 Hz), 2.67-2.74 (2 H, m), 2.46 (1 H, ddd, J=15.05, 10.52, 4.40 Hz), 1.94-2.04 (4 H, m).

Step 2: A 50-mL 2-neck round bottom flask was fitted with a nitrogen inlet and rubber septum and charged with N,N-diisopropylamine (0.598 mL, 4.26 mmol) in anhydrous THF (15 mL). The solution was cooled to −70° C., treated with n-butyllithium (3.05 mL, 4.26 mmol) and stirred for 30 min. A solution of methyl 1-(4-chloro-3-methoxyphenyl)piperidine-4-carboxylate (1.10 g, 3.88 mmol) in THF (3 mL) was added dropwise to the reaction and the resulting mixture was stirred at −70° C. for 1 h. After this time, the mixture was treated with iodomethane (0.253 mL, 4.07 mmol) and slowly warmed to RT. TLC and LC-MS (m/z=298.21) indicated the reaction was complete. The mixture was treated with water (25 mL) and extracted with EtOAc (3×30 mL). The extract was dried (Na$_2$SO$_4$) and concentrated on a rotary evaporator to give methyl 1-(4-chloro-3-methoxyphenyl)-4-methylpiperidine-4-carboxylate (1.06 g, 3.56 mmol, 92% yield) as a yellow solid. $^1$H-NMR (400 MHz, CDCl$_3$) δ ppm 7.17 (1 H, d, J=8.56 Hz), 6.48 (1 H, s), 6.44 (1 H, dd, J=8.69, 2.14 Hz), 3.86 (3 H, s), 3.70 (3 H, s), 3.38 (2 H, ddd, J=12.72, 4.03, 3.90 Hz), 2.82-2.91 (2 H, m), 2.19-2.26 (2 H, m), 1.52-1.64 (2 H, m), 1.24 (3 H, s).

Step 3: A solution of methyl 1-(4-chloro-3-methoxyphenyl)-4-methylpiperidine-4-carboxylate (500 mg, 1.679 mmol) in anhydrous THF (5 mL) and Et$_2$O (10 mL) was treated dropwise with lithium aluminum hydride (3.36 mL of a 1.0 M solution in THF, 3.36 mmol) while the reaction temperature was controlled with a water bath. The mixture was then stirred at RT for 1 h, treated with Na$_2$SO$_4$.10H$_2$O (1 g), stirred vigorously for 30 min and then dried with anhydrous MgSO$_4$. The mixture was filtered and concentrated to give (1-(4-chloro-3-methoxyphenyl)-4-methylpiperidin-4-yl)methanol as a pale yellow oil (460 mg). The product was used without further purification in the subsequent step.

Step 4: A solution of oxalyl chloride (0.176 mL, 2.015 mmol) in DCM (8 mL) was cooled to −70° C. and treated with anhydrous DMSO (0.238 mL, 3.36 mmol). The resultant solution was stirred at −70° C. for 20 min and then treated with (1-(4-chloro-3-methoxyphenyl)-4-methylpiperidin-4-yl)methanol in DCM (3 mL) and stirred for 40 min. Triethylamine (0.702 mL, 5.04 mmol) was added to the reaction. Upon completion of addition, the mixture was stirred at −70° C. for 30 min and then warmed to RT. The mixture was diluted with DCM, washed with sat NaHCO$_3$, brine, dried (Na$_2$SO$_4$) and concentrated to yield a residue. The residue was purified by flash chromatography on 12 g cartridge to give 1-(4-chloro-3-methoxyphenyl)-4-methylpiperidine-4-carbaldehyde (180 mg, 0.672 mmol, 40% yield) as a pale yellow oil. $^1$H-NMR (400 MHz, CDCl$_3$) δ ppm 9.50 (1 H, s), 7.18 (1 H, d, J=8.57 Hz), 6.47 (1 H, s), 6.43 (1 H, dd, J=8.57, 1.98 Hz), 3.82-3.89 (3 H, m), 3.27-3.36 (2 H, m), 2.93-3.03 (2 H, m), 2.03-2.12 (2 H, m), 1.57-1.67 (2 H, m), 1.11 (3 H, s).

Step 5: A solution of 1-(4-chloro-3-methoxyphenyl)-4-methylpiperidine-4-carbaldehyde (175 mg, 0.654 mmol), chloroiodomethane (0.052 mL, 0.719 mmol) and anhydrous THF (3 mL) was placed under nitrogen, cooled to −78° C. and treated dropwise with methyllithium (0.599 mL, 0.719 mmol) in Et$_2$O. The resulting mixture was stirred at −78° C. for 1.5 h, quenched with saturated NH$_4$Cl and then warmed to room temperature. The mixture was extracted with EtOAc. The extract was washed with brine, dried (MgSO$_4$) and concentrated on a rotary evaporator to give a clear oil which was a 1:1 mixture of the starting aldehyde and 2-chloro-1-(1-(4-chloro-3-methoxyphenyl)-4-methylpiperidin-4-yl)ethanol (80 mg). This mixture was used in the next step without purification.

Step 6: A solution of 4-chloro-3-methyl-5-(trifluoromethyl)-1H-pyrazole (55.4 mg, 0.30 mmol) in anhydrous THF (3 mL) was treated with 60% sodium hydride (13.20 mg, 0.330 mmol) and stirred at RT until hydrogen evolution ceased. The mixture was treated with a solution of 2-chloro-1-(1-(4-chloro-3-methoxyphenyl)-4-methylpiperidin-4-yl) ethanol (95 mg, 0.300 mmol) in THF and then stirred at reflux for 1 h. After this time, the mixture was cooled and treated with lithium bromide (0.30 mmol) and acetonitrile (4 mL) before being heated to 80° C. Within 10 min, LC-MS showed the chloro-alcohol had been converted to the epoxide but none of the desired product was detected by LC-MS. Accordingly, the mixture was charged with DMF (5 mL) and heated at 150° C. for 14 h, at which time a product having the mass (m/z=466) for the desired product was evident in the LC-MS. The mixture was concentrated on a rotary evaporator. The resultant residue was treated with EtOAc (10 mL), and the mixture was washed with water and brine. The organic extract was dried (Na$_2$SO$_4$) and concentrated in vacuo to give the crude product. The crude product was purified by flash chromatography (10-40% EtOAc/Hex) and then preparative reverse phase HPLC. Example 11 (32 mg, 0.069 mmol, 23% yield) was obtained as a white solid after lyophilization from the HPLC fractions. LC-MS: 466.18, [M+H]$^+$; $t_R$=3.21 min (method b). $^1$H-NMR (400 MHz, CDCl$_3$) δ ppm 7.46 (1 H, d, J=8.57 Hz), 7.41 (1 H, d, J=2.42 Hz), 6.95 (1 H, dd, J=8.68, 2.53 Hz), 4.24 (1 H, d, J=13.18 Hz), 3.93-4.05 (2 H, m), 3.92

(3 H, s), 3.68-3.77 (2 H, m), 3.43 (2 H, t, J=10.99 Hz), 2.35 (1 H, s), 2.34 (1 H, d, J=6.81 Hz), 2.31 (3 H, s), 1.82-1.94 (2 H, m), 1.23 (3 H, s).

Example 12a

Synthesis of 1-(1-(4-Chloro-3-methoxyphenyl)piperidin-4-yl)-2-(4-chloro-5-methyl-3-(trifluoromethyl)-1H-pyrazol-1-yl)propan-1-ol and separation into its two diastereomers

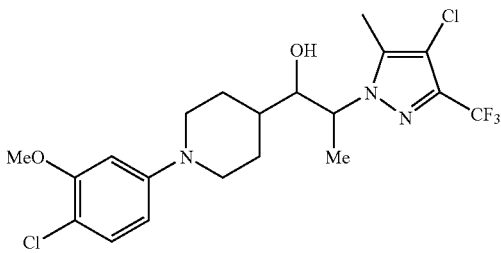 [SMILES: COc1cc(N2CCC(C(O)C(C)n3nc(C(F)(F)F)c(Cl)c3C)CC2)ccc1Cl]

Step 1: A solution of tert-butyl 1-(4-chloro-3-methoxyphenyl)piperidine-4-carboxylate (0.500 g, 1.535 mmol; this starting material was isolated as a reaction product in Example 1a, Step 1) in anhydrous $CH_2Cl_2$ (5 mL) was treated with trifluoroacetic acid (3 mL, 38.9 mmol) and the mixture stirred at RT for 2 h. After this time, the mixture was concentrated on the a rotary evaporator and the resultant residue was neutralized by first treating it with 2 M NaOH and then 0.1 M pH 7 phosphate buffer. The resultant mixture was extracted with EtOAc, and the extract was washed with brine, dried ($MgSO_4$) and concentrated to give 1-(4-chloro-3-methoxyphenyl)piperidine-4-carboxylic acid (0.45 g, 1.668 mmol, >100% yield) as a pale yellow solid. LC-MS: 270, [M+H].

Step 2: A mixture of 1-(4-chloro-3-methoxyphenyl)piperidine-4-carboxylic acid (9.0 g, 33.4 mmol), N,O-dimethylhydroxylamine hydrochloride (4.88 g, 50.1 mmol) and DCM (15 mL) was treated with 1-ethyl-3-(3-dimethylaminopropyl)carbodiimide hydrochloride (9.59 g, 50.1 mmol) and 4-(dimethylamino)pyridine (0.408 g, 3.34 mmol). The mixture was cooled in an ice bath and treated with N,N-diisopropylethylamine (11.62 mL, 66.7 mmol) over 3 min. After 10 min, the cooling bath was removed and the mixture was stirred at RT overnight (ca. 14 h). At the conclusion of this period, the mixture was diluted with DCM (50 mL), and then washed successively with saturated $NaHCO_3$ (3×25 mL), 1 M HCl (2×50 mL) and brine. The organic phase was dried ($MgSO_4$) and concentrated in vacuo. The resultant residue was purified by flash chromatography using a 120 g silica gel cartridge and 10:1 Hex/EtOAc to elute the product. The fractions containing the product were pooled and concentrated on a rotary evaporator to give 1-(4-chloro-3-methoxyphenyl)-N-methoxy-N-methylpiperidine-4-carboxamide as pale yellow oil.

Step 3: A solution of 1-(4-chloro-3-methoxyphenyl)-N-methoxy-N-methylpiperidine-4-carboxamide (450 mg, 1.439 mmol) in anhydrous $Et_2O$ (10 mL) and THF (5 mL) was placed under nitrogen and cooled to −78° C. The solution was treated with ethylmagnesium bromide (2.16 mL of a 2.0 M solution in $Et_2O$, 4.32 mmol) within 2 minutes and the stirred at for 20 minutes before warming the reaction to 0° C. The reaction was continued at 0° C. for 30 min and then poured into 0.5 M HCl (15 mL) and stirred vigorously for 5 min. The mixture was adjusted to pH 6 and extracted with $Et_2O$. The extract was washed with brine, dried ($MgSO_4$) and concentrated on a rotary evaporator to give 1-(1-(4-chloro-3-methoxyphenyl)piperidin-4-yl)propan-1-one (375 mg, 1.331 mmol, 93% yield) as a white solid.

Step 4: A solution of 1-(1-(4-chloro-3-methoxyphenyl)piperidin-4-yl)propan-1-one (350 mg, 1.242 mmol) in anhydrous THF (2 mL) was added dropwise at −78° C. to LDA [prepared form N,N-diisopropylamine (0.209 mL, 1.491 mmol) and 2.5 M butyllithium (0.596 mL, 1.491 mmol)/hexanes in anhydrous THF (2 mL)]. Upon completion of addition, the mixture was stirred for 40 min and then treated with chlorotrimethylsilane (0.284 mL, 2.236 mmol). After 30 min, the reaction was quenched with saturated $NH_4Cl$ and extracted with $Et_2O$. The extract was washed with brine, dried ($MgSO_4$) and concentrated to give the crude silyl ether [LC-MS: 354.0, [M+H]; $t_R$=2.39 min (method a)] containing 50% starting ketone. Without any additional purification, the product was dissolved in THF (10 mL), cooled to 0° C. and then treated with anhydrous sodium carbonate (171 mg, 1.615 mmol) and N-bromosuccinimide (232 mg, 1.304 mmol). After 30 min, the mixture was diluted with $Et_2O$ and washed with water, $Na_2S_2O_3$ and brine, dried ($Na_2SO_4$) and concentrated to give a crude mixture. LC-MS indicated that the crude mixture was made up of 15%, 25%, 30%, 30% of starting ketone, monobrominated product 1, monobrominated product 2 and dibrominated product, respectively. The crude mixture was used in Step 5 without additional purification.

Step 5: A mixture of 4-chloro-5-methyl-3-(trifluoromethyl)-1H-pyrazole (221 mg, 1.200 mmol), anhydrous potassium carbonate (166 mg, 1.200 mmol) and acetonitrile (10 mL) was stirred at RT for 20 min and then cooled to 0° C. Once at the prescribed temperature, the mixture was treated with a solution of the crude mixture from Step 4 above (433 mg, 1.2 mmol) in acetonitrile (2 mL). The mixture was warmed to RT and stirred overnight. After this time, the solvent was removed under reduced pressure and the resultant residue was partitioned between EtOAc and brine. The organic phase was separated, dried ($Na_2SO_4$) and concentrated on a rotary evaporator. The resultant residue was purified by flash chromatography using a 12 g silica gel cartridge and gradient elution from 10:1 Hex/EtOAc to 3:1 Hex/EtOAc. The fractions containing the product were pooled and concentrated on a rotary evaporator to give Example 12a (65 mg, 0.140 mmol, 11.7% yield) as a clear oil. LC-MS: 464.18, [M+H]; $t_R$=3.65 min (method b).

Step 6: A solution of 1-(1-(2-bromo-4-chloro-5-methoxyphenyl)piperidin-4-yl)-2-(4-chloro-5-methyl-3-(trifluoromethyl)-1H-pyrazol-1-yl)propan-1-one (55 mg, 0.101 mmol) in 1,2-dichlororethane (1.5 mL) and MeOH (1 mL) was treated with sodium borohydride (7.66 mg, 0.203 mmol). The mixture was stirred at RT under nitrogen for 20 min until the reaction was indicated as complete by LC-MS (two sets of diastereomers were observed in a 2:1 ratio of more polar to less polar). The reaction was treated with acetone (30 μL), stirred for 10 min, and then concentrated on a rotary evaporator to give the crude product. The crude product was dissolved in acetonitrile and purified by preparative HPLC (method f) to afford both diastereomer 1 (16 mg) and diastereomer 2 (9 mg) of Example 12a. Data for diastereomer 1: LC-MS: 466.18, [M+H]$^+$; $t_R$=3.13 min (method b); $^1$H-NMR (400 MHz, $CDCl_3$) δ ppm 7.39 (1 H, d, J=8.57 Hz), 7.23 (1 H, d, J=2.20 Hz), 6.82 (1 H, dd, J=8.68, 2.53 Hz), 4.37 (1 H, dt, J=11.37, 6.73 Hz), 3.90 (3 H, s), 3.66-3.79 (3 H, m), 2.96-3.14 (2 H, m), 2.21-2.36 (4 H, m), 1.96-2.17 (2 H, m), 1.66 (1 H, s), 1.46-1.59 (4 H, m). Data for diastereomer 2: LC-MS: 466.18, [M+H]$^+$; $t_R$=3.32 min (method b); $^1$H-NMR (400 MHz, $CDCl_3$) δ ppm 7.39 (1 H, d, J=8.57 Hz), 7.20 (1 H, d, J=1.98 Hz), 6.80 (1 H, dd, J=8.57, 2.42 Hz), 4.33 (1 H, qd, J=6.70, 2.53 Hz), 3.91 (3 H, s), 3.84 (1 H, dd, J=7.91, 2.42 Hz), 3.70-3.79 (2 H, m), 3.04-3.13 (2 H, m), 2.23-2.30 (4 H, m CH₃ and CH), 2.01-2.09 (1 H, m), 1.94-2.00 (1 H, m), 1.85 (1 H, d, J=12.74 Hz), 1.67-1.77 (1 H, m), 1.45 (3 H, d, J=6.81 Hz).

Example 12b

Synthesis of 1-(1-(2-Bromo-4-chloro-5-methoxyphenyl)piperidin-4-yl)-2-(4-chloro-5-methyl-3-(trifluoromethyl)-1H-pyrazol-1-yl)propan-1-ol, and Separation into its Two Diastereomers

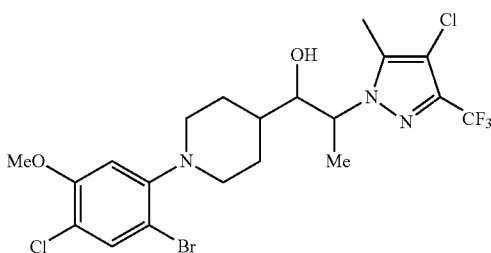 [SMILES: COc1cc(N2CCC(C(O)C(C)n3nc(C(F)(F)F)c(Cl)c3C)CC2)c(Br)cc1Cl]

Step 1: From the chromatography described in Example 12a, Step 5, a sample of 1-(1-(2-bromo-4-chloro-5-methoxyphenyl)piperidin-4-yl)-2-(4-chloro-5-methyl-3-(trifluoromethyl)-1H-pyrazol-1-yl)propan-1-one was isolated. This sample was triturated with MeOH to give pure 1-(1-(2-bromo-4-chloro-5-methoxyphenyl)piperidin-4-yl)-2-(4-chloro-5-methyl-3-(trifluoromethyl)-1H-pyrazol-1-yl)propan-1-one 9 (60 mg). LC-MS: 544.10, [M+H]; $t_R$=4.42 min (method b). ¹H-NMR (400 MHz, CDCl₃) δ ppm 7.50 (1 H, s), 6.55 (1 H, s), 5.02 (1 H, q, J=7.03 Hz), 3.86 (3 H, s), 3.28-3.37 (2 H, m), 2.52-2.64 (2 H, m, J=18.02, 11.53, 11.53, 2.20 Hz), 2.42-2.51 (1 H, m), 2.26 (3 H, s), 1.86-2.02 (1 H, m), 1.78-1.86 (2 H, m), 1.72 (3 H, d, J=7.25 Hz), 1.63 (1 H, d, J=12.96 Hz).

Step 2: A solution of 1-(1-(2-bromo-4-chloro-5-methoxyphenyl)piperidin-4-yl)-2-(4-chloro-5-methyl-3-(trifluoromethyl)-1H-pyrazol-1-yl)propan-1-one (55 mg, 0.101 mmol) in 1,2-dichloroethane (1.5 mL) and MeOH (1 mL) was treated with sodium borohydride (7.66 mg, 0.203 mmol). The mixture was stirred at RT under nitrogen for 20 min. After this time, the reaction was treated with acetone (30 μL), stirred for 10 min and then concentrated on a rotary evaporator to give racemic Example 12b. Racemic Example 12b was dissolved in acetonitrile and the purified by preparative HPLC (method f) to afford both diastereomer 1 (27 mg) and diastereomer 2 (9 mg) of Example 12b. Data for diastereomer 1: LC-MS: 546.12, [M+H]; $t_R$=4.30 min (method b); ¹H-NMR (400 MHz, CDCl₃) δ ppm 7.55 (1 H, s), 6.84 (1 H, br. s), 4.39 (1 H, dt, J=11.42, 6.70 Hz), 3.88 (4 H, s), 3.71 (1 H, dd, J=6.92, 4.50 Hz), 3.41-3.51 (2 H, m), 2.26-2.32 (4 H, m, CH₃ and CH), 2.10 (1 H, d, J=11.86 Hz), 1.87 (2 H, d, J=8.57 Hz), 1.57-1.53 (1 H, m), 1.53 (3 H, d, J=6.81 Hz), 1.39-1.49 (1 H, m). Data for diastereomer 2: LC-MS: 546.12, [M+H]; $t_R$=4.38 min (method b); ¹H-NMR (400 MHz, CDCl₃) δ ppm 7.54-7.57 (1 H, m), 6.91 (1 H, s), 4.37 (1 H, qd, J=6.81, 1.98 Hz), 3.85-3.90 (4 H, m, CH₃ and CH), 3.80 (1 H, dd, J=8.02, 2.09 Hz), 3.44-3.55 (2 H, m), 3.06 (1 H, s), 2.30 (3 H, s), 2.23-2.29 (1 H, m), 1.77 (2 H, m), 1.62-1.73 (2 H, m), 1.44 (3 H, d, J=6.81 Hz).

Example 13

1-(4-Chloro-3-methoxyphenyl)-4-(2-(4-chloro-5-methyl-3-(trifluoromethyl)-1H-pyrazol-1-yl)-1-hydroxyethyl)piperidin-4-ol

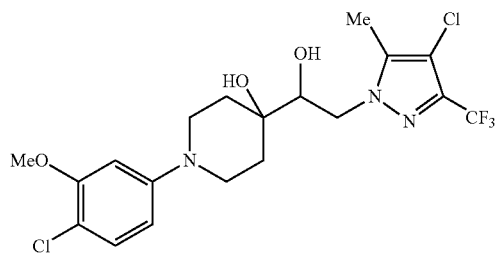 [SMILES: COc1cc(N2CCC(O)(C(O)Cn3nc(C(F)(F)F)c(Cl)c3C)CC2)ccc1Cl]

Step 1: A 20-mL microwave vial was charged with sodium tert-butoxide (537 mg, 5.59 mmol), acetato(2'-di-t-butylphosphino-1,1'-biphenyl-2-yl)palladium (II) (259 mg, 0.559 mmol) and a stir bar. The vial was sealed and purged with nitrogen. A solution of 1,4-dioxa-8-azaspiro[4.5]decane (800 mg, 5.59 mmol) and 5-bromo-2-chloroanisole (1361 mg, 6.15 mmol) in 5:1 toluene/t-BuOH (12 mL) was added via syringe. The mixture was heated by microwave (300 W) at 160° C. for 10 min and then cooled and partitioned between EtOAc and brine. The aqueous phase was extracted with EtOAc and the organic phases were combined. The resultant solution was dried (Na₂SO₄) and concentrated on a rotary evaporator to give the crude product. The crude product was purified by flash chromatography using a 40 g silica gel cartridge column and gradient elution with EtOAc/hexanes to afford 8-(4-chloro-3-methoxyphenyl)-1,4-dioxa-8-azaspiro[4.5]decane (1.1 g, 70%) as a yellow solid.

Step 2: A sample of 8-(4-chloro-3-methoxyphenyl)-1,4-dioxa-8-azaspiro[4.5]decane (1.1 g, 2.89 mmol) was treated with 6 M HCl (15 mL) and heated at reflux for 3 h. The mixture was cooled to RT and made basic with 2 M NaOH. The basic mixture was extracted with EtOAc. The extract was dried (Na₂SO₄) and concentrated on a rotary evaporator to give the crude product. The crude product was purified by flash chromatography (40 g silica gel cartridge and gradient elution from 10 to 40% EtOAc/hexanes) to give 1-(4-chloro-3-methoxyphenyl)piperidin-4-one (690 mg, 2.88 mmol, 51.5% yield) as a yellow oil. ¹H-NMR (400 MHz, CDCl₃) δ ppm 7.21 (1 H, d, J=8.57 Hz), 6.52 (1 H, d, J=2.64 Hz), 6.47 (1 H, dd, J=8.68, 2.75 Hz), 3.88 (3 H, s), 3.57 (4 H, t, J=6.04 Hz), 2.55 (4 H, t, J=6.04 Hz).

Step 3: A suspension of 60% dispersion sodium hydride (65.1 mg, 1.627 mmol) in anhydrous THF (2.5 mL) was treated with a solution of trimethyl phosphonoacetate (235 μL, 1.627 mmol) in THF (1 mL) over 5 min. The mixture was stirred at RT for 30 min and then treated with a solution of 1-(4-chloro-3-methoxyphenyl)piperidin-4-one (300 mg, 1.252 mmol) in THF (3 mL). The reaction was stirred at RT for 1 h before it was partitioned between saturated NH₄Cl and EtOAc. The extract was dried (Na₂SO₄) and concentrated to give the crude product, which was purified by flash chromatography (12 g silica gel cartridge and gradient elution from 0 to 30% EtOAc/hexanes) to afford methyl 2-(1-(4-chloro-3-methoxyphenyl)piperidin-4-ylidene)acetate (288 mg, 0.974 mmol, 78% yield) as a white solid. $^1$H-NMR (400 MHz, CDCl$_3$) δ ppm 7.19 (1 H, d, J=8.79 Hz), 6.49 (1 H, d, J=2.42 Hz), 6.44 (1 H, dd, J=8.79, 2.64 Hz), 5.73 (1 H, s), 3.88 (3 H, s), 3.70 (3 H, s), 3.26-3.34 (4 H, m, J=5.82, 5.49, 5.33, 5.33 Hz), 3.10 (2 H, t, J=5.38 Hz), 2.45 (2 H, t, J=5.27 Hz).

Step 4: A solution of methyl 2-(1-(4-chloro-3-methoxyphenyl)piperidin-4-ylidene)acetate (275 mg, 0.930 mmol) in anhydrous THF (3 mL) was cooled to −78° C. and then treated with DIBAL-H (3.72 mL of a 1.0 M solution in toluene, 3.72 mmol). The reaction was stirred at −78° C. for 2.5 h and then quenched with EtOAc. After it warmed to 0° C., the mixture was treated with saturated potassium sodium tartrate solution and stirred vigorously for 20 min. The resulting mixture was extracted with EtOAc. The extract was dried (Na$_2$SO$_4$) and concentrated to give a yellow oil, which was purified by flash chromatography (4 g silica gel cartridge and gradient elution with EtOAc/hexanes) to give 2-(1-(4-chloro-3-methoxyphenyl)piperidin-4-ylidene)ethanol (253 mg, 0.945 mmol, 102% yield) as a yellow oil. $^1$H-NMR (400 MHz, CDCl$_3$) δ ppm 7.18 (1 H, d, J=8.79 Hz), 6.48 (1 H, d, J=16.92 Hz), 6.43 (1 H, s), 5.50 (1 H, t, J=7.03 Hz), 4.18 (2 H, d, J=7.03 Hz), 3.87 (3 H, s), 3.22 (4 H, dt, J=9.50, 5.68 Hz), 2.39-2.48 (2 H, m), 2.32-2.39 (2 H, m).

Step 5: A solution of 2-(1-(4-chloro-3-methoxyphenyl)piperidin-4-ylidene)ethanol (253 mg, 0.945 mmol) and triethylamine (191 μL, 1.373 mmol) in dry DCM (2.3 mL) was cooled in an ice bath and then treated with methanesulfonyl chloride (93 μL, 1.190 mmol). The mixture was stirred at 0° C. for 1 hour and then poured into ice water. The resulting mixture was extracted with DCM. The extract was washed sequentially with sat. NaHCO$_3$ and brine, and then dried (MgSO$_4$) and concentrated on a rotary evaporator to yield a mesylate. This mesylate was used without subsequent purification in Step 6 set forth below.

Step 6: A solution of 4-chloro-3-trifluoromethyl-5-(methyl)pyrazole (338 mg, 1.830 mmol) in anhydrous DMF (1.5 mL) was treated with 60% sodium hydride (73.2 mg, 1.830 mmol) and stirred at RT for 30 min before being charged with a solution of the unpurified mesylate (from Step 5 above) in DCM (1 mL) and tetrabutylammonium iodide (6.76 mg, 0.018 mmol). The resulting mixture was stirred at 80° C. for 1 h. Analysis of the mixture by LC-MS showed 2 products having the desired (M+H)=434 in a 3:1 ratio. The mixture was concentrated on a rotary evaporator and the resultant residue was partitioned between EtOAc and brine. The organic phase was washed with 1 M NaOH (3 times) and brine, dried (Na$_2$SO$_4$) and concentrated to give the crude product mixture. The crude product mixture was purified by flash chromatography on silica gel using 0-40% EtOAc in hexanes to give 1-(4-chloro-3-methoxyphenyl)-4-(2-(4-chloro-5-methyl-3-(trifluoromethyl)-1H-pyrazol-1-yl)ethylidene)piperidine (77 mg, 19%) and 1-(4-chloro-3-methoxyphenyl)-4-(2-(3-chloro-4-methyl-5-(trifluoromethyl)-1H-pyrazol-1-yl)ethylidene)piperidine (25 mg, 6%). $^1$H-NMR (400 MHz, CDCl$_3$) δ ppm 7.19 (1 H, d, J=8.56 Hz), 6.50 (1 H, s), 6.45 (1 H, d, J=8.31 Hz), 5.37 (1 H, t, J=6.80 Hz), 4.75 (2 H, d, J=7.05 Hz), 3.85-3.92 (3 H, m), 3.20-3.29 (4 H, m), 2.52 (2 H, s), 2.36 (2 H, d, J=4.78 Hz), 2.24-2.30 (3 H, m).

Step 7: A mixture of 1-(4-chloro-3-methoxyphenyl)-4-(2-(4-chloro-5-methyl-3-(trifluoromethyl)-1H-pyrazol-1-yl) ethylidene)piperidine (66 mg, 0.152 mmol), tert-butanol (760 μL) and water (760 μL) was stirred at RT until homogeneous. Potassium ferricyanide(III) (79 μL, 0.456 mmol), potassium carbonate (63.0 mg, 0.456 mmol), potassium osmate (VI) dihydrate (1.120 mg, 3.04 μmol) and quinuclidine (0.338 mg, 3.04 μmol) were added to the mixture, which was then stirred vigorously at RT for 3 h. After this time, the mixture was quenched with sodium sulfite and extracted with EtOAc. The extract was washed with brine, dried (Na$_2$SO$_4$), and concentrated to give the crude product. The crude product was purified by preparative HPLC (method f) to afford Example 13 as a white solid after lypholization (47 mg, 0.100 mmol, 66% yield). LC-MS: 468.26, [M+H]$^+$; t$_R$=3.03 min (method b). $^1$H-NMR (400 MHz, CDCl$_3$) δ ppm 7.49 (1 H, d, J=8.57 Hz), 7.43 (1 H, d, J=2.64 Hz), 7.04 (1 H, dd, J=8.57, 2.42 Hz), 4.26-4.33 (1 H, m), 4.09-4.16 (1 H, m), 4.03 (1 H, dd, J=8.35, 2.20 Hz), 3.91-3.95 (3 H, m), 3.69-3.79 (2 H, m), 3.56 (2 H, t, J=12.52 Hz), 2.45-2.55 (2 H, m), 2.30-2.33 (3 H, m), 1.95-2.05 (2 H, m).

Example 14

4-(2-(4-Chloro-5-methyl-3-(trifluoromethyl)-1H-pyrazol-1-yl)ethyl)-1-(2,4-dichloro-5-methoxyphenyl)piperidin-4-ol

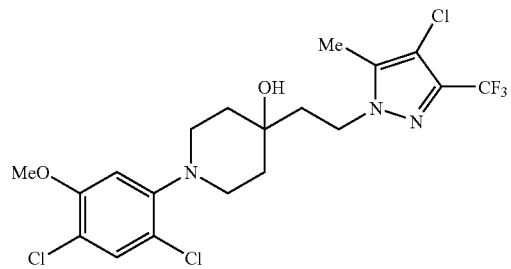 [SMILES: COc1cc(N2CCC(O)(CCn3nc(C(F)(F)F)c(Cl)c3C)CC2)c(Cl)cc1Cl]

Step 1: A mixture of 8-(4-chloro-3-methoxyphenyl)-1,4-dioxa-8-azaspiro[4.5]decane (1.67 g, 5.89 mmol, Example 13, step 1) and 1-chloropyrrolidine-2,5-dione (0.786 g, 5.89 mmol) in AcOH (15 mL) was heated at 60° C. overnight. The mixture was cooled and water was added. Upon completion of addition, the mixture was neutralized with 1N NaOH, extracted with EtOAc, dried (Na$_2$SO$_4$), and concentrated to give 8-(2,4-dichloro-5-methoxyphenyl)-1,4-dioxa-8-azaspiro[4.5]decane (1.7 g, 5.34 mmol, 91% yield) as a yellow oil.

Step 2: To a solution of 8-(2,4-chloro-3-methoxyphenyl)-1,4-dioxa-8-azaspiro[4.5]decane (1.6 g, 5.05 mmol) in THF (5 mL) was added hydrogen chloride (1.469 g, 14.10 mmol). Upon completion of addition, the mixture was stirred at RT overnight. After this time, the mixture was concentrated and purified by a flash column to give 1-(4-chloro-3-methoxyphenyl)piperidin-4-one (1.1 g, 4.59 mmol, 81% yield) as a yellow oil.

Step 3: Zinc (269 mg, 4.11 mmol) was placed in a 100-mL two-necked round bottom flask fitted with a reflux condenser and septum. The reaction vessel was evacuated and flushed with nitrogen before being charged sequentially with anhydrous benzene (5 mL), anhydrous Et$_2$O (5 mL), and ethyl 2-bromoacetate (0.228 mL, 2.057 mmol; added dropwise). A crystal of 12 was added to initiate the reaction. After 15 min, 1-(2,4-dichloro-5-methoxyphenyl)piperidin-4-one (470 mg, 1.714 mmol) was added dropwise. The reaction was refluxed at 80° C. for 6 h, cooled to RT, and charged with 10% HCl (5 mL). The mixture was extracted with Et$_2$O (2×20 mL), and the combined extracts were washed with dilute HCl (5 mL) and water (2×10 mL) before being dried (Na$_2$SO$_4$) and concentrated in vacuo to yield a residue. The residue was purified by flash chromatography to provide ethyl 2-(1-(2,4-dichloro- 5-methoxyphenyl)-4-hydroxypiperidin-4-yl)acetate (352 mg, 0.972 mmol, 57% yield) as a yellow oil.

Step 4: To a solution of ethyl 2-(1-(2,4-dichloro-5-methoxyphenyl)-4-hydroxypiperidin-4-yl)acetate (1 g, 2.76 mmol) in THF (10 mL) was added LiAlH$_4$ (0.210 g, 5.52 mmol). The reaction mixture was stirred at RT for 2 h, quenched with minimum water and then treated with EtOAc and solid NaHCO$_3$. The mixture was stirred and filtered. The filtrate was concentrated to give 1-(2,4-dichloro-5-methoxyphenyl)-4-(2-hydroxyethyl)piperidin-4-ol (0.62 g, 1.936 mmol, 70% yield) as a yellow oil.

Step 5: A solution of 1-(2,4-dichloro-5-methoxyphenyl)-4-(2-hydroxyethyl)piperidin-4-ol (500 mg, 1.561 mmol) in pyridine (2 mL) was cooled to 0° C. and then treated with benzenesulfonyl chloride (331 mg, 1.874 mmol). The reaction was stirred at RT for 1 h before being quenched with water. The resultant mixture was extracted with EtOAc. The organic phase was concentrated in vacuo, and the resultant residue was purified by flash chromatography using 0-30% EtOAc in hexanes as the eluent to give 2-(1-(2,4-dichloro-5-methoxyphenyl)-4-hydroxypiperidin-4-yl)ethyl benzenesulfonate (340 mg, 0.739 mmol, 47% yield) was obtained as a yellow oil.

Step 6: A solution of 2-(1-(2,4-dichloro-5-methoxyphenyl)-4-hydroxypiperidin-4-yl)ethyl benzenesulfonate (300 mg, 0.652 mmol) in acetone (5 mL) was treated with potassium bromide (194 mg, 1.629 mmol) and 18-crown-6 (189 mg, 0.717 mmol). The mixture was stirred at RT for 60 h before being concentrated in vacuo. The resultant residue was dissolved in EtOAc, and the resultant solution was washed with brine, dried (Na$_2$SO$_4$), and concentrated to give a residue. This residue was purified by a flash column using 0-30% EtOAc in heptanes as eluent to give 4-(2-bromoethyl)-1-(2,4-dichloro-5-methoxyphenyl)piperidin-4-ol (102 mg, 0.266 mmol, 41% yield) as a yellow oil.

Step 7: A solution of 4-(2-bromoethyl)-1-(2,4-dichloro-5-methoxyphenyl)piperidin-4-ol (100 mg, 0.261 mmol) in acetonitrile (5 mL) was treated with 4-chloro-5-methyl-3-(trifluoromethyl)-1H-pyrazole (57.8 mg, 0.313 mmol) and potassium carbonate (72.1 mg, 0.522 mmol). The mixture was heated at 80° C. for 16 h. After this time, the reaction was cooled, quenched with water and extracted with EtOAc. The extract was washed with brine, dried (Na$_2$SO$_4$) and concentrated. The resultant residue was purified by preparative HPLC (method h) to give Example 14 (22 mg, 0.045 mmol, 34.6% yield). LC-MS: 486.11, [M+H]$^+$; HPLC $t_R$=4.60 min (method c). $^1$H-NMR (400 MHz, CDCl$_3$) δ ppm 7.34 (1 H, s), 6.65 (1 H, s), 4.39 (2 H, t, J=7.25 Hz), 3.87 (3 H, s), 3.08-3.17 (2 H, m), 3.01 (2 H, td, J=11.53, 2.42 Hz), 2.23 (3 H, s), 1.98-2.10 (2 H, m), 1.85 (2 H, td, J=12.30, 4.39 Hz), 1.72 (2 H, d).

Example 15a 2-(4-Chloro-5-methyl-3-(trifluoromethyl)-1H-pyrazol-1-yl)-1-(1-(4-chlorophenyl)piperidin-4-yl)ethanol

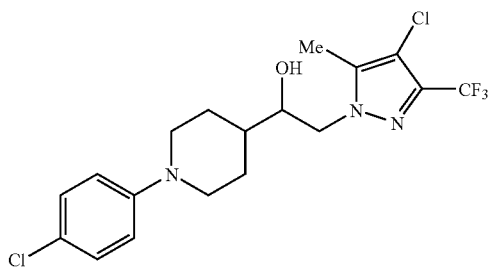 [SMILES: Cc1c(Cl)c(C(F)(F)F)nn1CC(O)C1CCN(c2ccc(Cl)cc2)CC1]

Step 1: A mixture of 1-(tert-butoxycarbonyl)piperidine-4-carboxylic acid (9.20 g, 40.1 mmol), N,O-dimethylhydroxylamine hydrochloride (5.87 g, 60.2 mmol) and CH$_2$Cl$_2$ (120 mL) was treated with 1-(3-dimethylaminopropyl)-3-ethylcarbodiimide hydrochloride (11.54 g, 60.2 mmol), N,N-diisopropylethylamine (10.51 mL, 60.2 mmol) and 4-(dimethylamino)pyridine (250 mg, 2.046 mmol) before being stirred at RT overnight. After this time, the mixture was diluted with DCM (100 mL) and washed sequentially with 1 M hydrochloric acid (2×75 mL), saturated NaHCO$_3$ (100 mL), and brine (100 mL). The organic phase was dried (MgSO$_4$) and then concentrated in vacuo to give tert-butyl 4-(methoxy(methyl)carbamoyl)-piperidine-1-carboxylate as a colorless oil (9.9 g), which was used in the next step without any further purification.

Step 2: A 3-neck, 250 mL round bottom flask was charged with a solution of tert-butyl 4-(methoxy(methyl)carbamoyl)piperidine-1-carboxylate (9.9 g) in Et$_2$O (120 mL). The flask was purged with nitrogen and then cooled in a CO$_2$/acetone bath. Methylmagnesium bromide (26.8 mL of a 3.0 M solution in Et$_2$O, 80 mmol) was added dropwise over 10 min to the amide. The resulting thick mixture was warmed to 0° C. and then stirred for 40 min before being poured into 2 M HCl solution (50 mL). The mixture was diluted with Et$_2$O (100 mL), washed with brine, dried (MgSO$_4$) and concentrated on a rotary evaporator to give tert-butyl 4-acetylpiperidine-1-carboxylate (7.3 g, 32.1 mmol, 80% yield) as a colorless oil. The product partly crystallized on standing at RT. $^1$H-NMR (400 MHz, CDCl$_3$) δ ppm 4.06 (2 H, s), 2.74 (2 H, s), 2.42 (1 H, s), 2.12 (2 H, s), 1.78 (2 H, s), 1.49 (2 H, s), 1.41 (9 H, s).

Step 3: A solution of diisopropylamine (5.19 mL, 36.4 mmol) in anhydrous THF (10 mL) was cooled to −78° C. and then treated with n-BuLi (22.77 mL of a 1.6 M solution in hexanes, 36.4 mmol). After stirring for 15 min, the mixture was treated dropwise with a solution of tert-butyl 4-acetylpiperidine-1-carboxylate (6.9 g, 30.4 mmol) in anhydrous THF (50 mL) over 30 min. The resulting mixture was stirred at −78° C. for 40 min, treated with TMS-Cl (6.98 mL, 54.6 mmol) over 15 min and stirred for an additional hour. After this time, the reaction mixture was poured into sat NaHCO$_3$ (350 mL) and extracted with Et$_2$O (250 mL). The extract was washed with brine, dried (MgSO$_4$) and concentrated on a rotary evaporator. The resultant residue was dissolved in anhydrous THF (150 mL). The resultant solution was cooled to 0° C. and treated sequentially with sodium bicarbonate (3.32 g, 39.5 mmol) and NBS (4.86 g, 27.3 mmol). The mixture was stirred at RT for 90 min and then partitioned between saturated NaHCO$_3$ (250 mL) and Et$_2$O (250 mL). The aqueous phase was extracted with Et$_2$O (200 mL). The combined ethereal extracts were washed with saturated NaHCO$_3$, washed with brine, dried (MgSO$_4$) and concentrated on a rotary evaporator to give a brown oil (9.5 g). After storing the product at −40° C. for 5 days, a portion of the oily product started to crystallize. The material was triturated with hexanes (3×100 mL) and then with Et$_2$O (200 mL). The Et$_2$O solution was decanted from the brown insoluble oil and concentrated in vacuo to give tert-butyl 4-(2-bromoacetyl)piperidine-1-carboxylate (7.5 g, 24.49 mmol, 81% yield) as a pale brown oil, which partly crystallized on standing at RT. $^1$H-NMR (400 MHz, CDCl$_3$) δ ppm 4.03-4.15 (2 H, m), 3.93 (2 H, s), 2.86 (1 H, tt, J=11.34, 3.82 Hz), 2.72-2.81 (2 H, m), 1.82 (2 H, d, J=12.30 Hz), 1.50-1.60 (2 H, m), 1.34-1.46 (9 H, m).

Step 4: A mixture of 4-chloro-5-methyl-3-(trifluoromethyl)-1H-pyrazole (0.784 g, 4.25 mmol), anhydrous potassium carbonate (1.354 g, 9.80 mmol) and anhydrous acetonitrile (50 mL) was stirred at RT for 15 min and then treated with a solution of tert-butyl 4-(2-bromoacetyl)piperidine-1-carboxylate (1.0 g, 3.27 mmol) in anhydrous acetonitrile (5 mL). The resulting mixture was stirred at RT overnight to give a bright yellow mixture, which was concentrated on a rotary evaporator. The resultant residue was partitioned between EtOAc (50 mL) and water (25 mL). The organic phase was washed with 1 M NaOH (3×20 mL), washed with brine, dried ($MgSO_4$) and concentrated on a rotary evaporator to give a yellow foam (1.5 g). The yellow foam was purified by flash chromatography using a 40 g silica gel cartridge and gradient elution from 10:1 Hex/EtOAc to 3:1 Hex/EtOAc (product Rf=0.25 with 3:1 Hexane/EtOAc; TLC visualized with $KMnO_4$). The fractions containing the product were pooled and concentrated on a rotary evaporator to give tert-butyl 4-(2-(4-chloro-5-methyl-3-(trifluoromethyl)-1H-pyrazol-1-yl)acetyl)piperidine-1-carboxylate (1.1 g, 2.68 mmol, 82% yield). $^1$H-NMR (400 MHz, $CDCl_3$) δ ppm 4.99 (2 H, s), 4.09-4.20 (2 H, m), 2.79 (2 H, t, J=12.41 Hz), 2.56-2.64 (1 H, m), 2.15 (3 H, s), 1.85 (2 H, d, J=11.86 Hz), 1.55-1.65 (2 H, m), 1.41-1.47 (9 H, m).

Step 5: A solution of tert-butyl 4-(2-(4-chloro-5-methyl-3-(trifluoromethyl)-1H-pyrazol-1-yl)acetyl)piperidine-1-carboxylate (1.0 g, 2.440 mmol) in anhydrous $CH_2Cl_2$ (20 mL) was treated with sodium borohydride (0.055 g, 1.464 mmol), followed by anhydrous MeOH (4 mL). The mixture was stirred at RT for 1.5 h and then concentrated on a rotary evaporator. The resultant residue was treated with 4 M HCl in dioxane (10 mL). After stirring for 2 h, the mixture was concentrated and this residue was made basic with a minimum amount of saturated $NaHCO_3$. The mixture was lyophilized. The resultant lyopholate was treated with $CH_2Cl_2$ (50 mL), stirred vigorously for 5 minutes, and then filtered ($CH_2Cl_2$ washes). The combined $CH_2Cl_2$ filtrates were concentrated to give 2-(4-chloro-5-methyl-3-(trifluoromethyl)-1H-pyrazol-1-yl)-1-(piperidin-4-yl)ethanol (0.79 g, 2.53 mmol, 104% yield) as an off-white solid. $^1$H-NMR (400 MHz, $CDCl_3$) δ ppm 4.09-4.17 (1 H, m), 3.95-4.02 (1 H, m), 3.86 (1 H, ddd, J=8.84, 6.21, 2.31 Hz), 3.11-3.19 (2 H, m), 2.62 (2 H, tt, J=12.28, 3.10 Hz), 2.29 (3 H, s), 1.84 (1 H, d, J=12.96 Hz), 1.64-1.71 (1 H, m), 1.55-1.64 (1 H, m), 1.34-1.44 (2 H, m).

Step 6: A 25-mL round bottom flask was charged with 2-(4-chloro-5-methyl-3-(trifluoromethyl)-1H-pyrazol-1-yl)-1-(piperidin-4-yl)ethanol (50 mg, 0.160 mmol), anhydrous toluene (3 mL) and DMF (1 mL). Sodium tert-butoxide (23.12 mg, 0.241 mmol) and acetato(2'-di-t-butylphosphino-1,1'-biphenyl-2-yl)palladium (II) (7.42 mg, 0.016 mmol) were added to the solution, which was then heated at 70° C. under nitrogen for 30 min. After this time, the mixture was concentrated on a rotary evaporator and the resultant residue was partitioned between ethyl acetate and brine. The organic phase was dried ($MgSO_4$) and concentrated to give the crude product. The crude product was purified by preparative HPLC (method f). The fraction containing the desired product was concentrated and lyophilized to give Example 15a (7 mg, 0.013 mmol, 8% yield) as a white solid. LC-MS: 422.3, $[M+H]^+$; $t_R$=3.02 min (method b). $^1$H-NMR (400 MHz, $CDCl_3$) δ ppm 7.40 (2 H, ddd, J=9.39, 2.75, 2.58 Hz), 7.31-7.36 (2 H, m), 4.16-4.22 (1 H, m), 4.01-4.09 (1 H, m), 3.97-4.01 (1 H, m, J=5.44, 5.44, 2.86, 2.53 Hz), 3.75 (2 H, d, J=11.86 Hz), 3.01-3.11 (2 H, m), 2.27-2.33 (4 H, m, $CH_3$ and 0.5 $CH_2$), 2.01-2.12 (4 H, m).

Examples 15b to 15e

Examples 15b to 15e were made using the methods exemplified above in Example 15a. Data for Examples 15b to 15e are provided in Table 5 below. The substituents listed in each column are to be paired with the structure embedded in the table heading. In the synthesis of the examples, substitutions for key reagents were made in Step 6 of the procedure outlined in Example 15a, as will be evident to one skilled in the art. The data in the "MS" column represent the values observed for the $(M+H)^+$ ions in electrospray mass spectroscopy experiments. For mass spectra in which multiple isotopes were observed, the major ion is listed. {Note: For compounds with one or two Cl atoms, this is typically the first ion of two significant ions; for compounds with three Cl atoms, this is typically the second ion of three significant ions.} The data in the "HPLC" column indicate the retention time with method conditions show in brackets.

TABLE 5

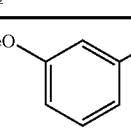

| Example | Name | $R_{12}$ | MS | HPLC $t_R$ (method) |
|---|---|---|---|---|
| 15b | 2-(4-Chloro-5-methyl-3-(trifluoromethyl)-1H-pyrazol-1-yl)-1-(1-(3-methoxyphenyl)piperidin-4-yl)ethanol | 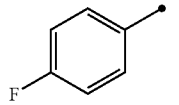 | 418.2 | 1.42 (a) |
| 15c | 2-(4-Chloro-5-methyl-3-(trifluoromethyl)-1H-pyrazol-1-yl)-1-(1-(4-fluorophenyl)piperidin-4-yl)ethanol | | 406.1 | 1.39 (a) |

TABLE 5-continued

[Structure: piperidine with R1 on N, CH(OH)CH2 linker to pyrazole (Me, Cl, CF3 substituents)]

| Example | Name | R12 | MS | HPLC $t_R$ (method) |
|---|---|---|---|---|
| 15d | 1-(1-(2-Chloro-5-methoxyphenyl)piperidin-4-yl)-2-(4-chloro-5-methyl-3-(trifluoromethyl)-1H-pyrazol-1-yl)ethanol | MeO-phenyl-Cl | 452.0 | 3.81 (b) |
| 15e | 2-(4-Chloro-5-methyl-3-(trifluoromethyl)-1H-pyrazol-1-yl)-1-(1-(2-chlorophenyl)piperidin-4-yl)ethanol | phenyl-Cl | 422.0 | 3.71 (b) |

Example 15f 4-(4-(2-(4-Chloro-5-methyl-3-(trifluoromethyl)-1H-pyrazol-1-yl)acetyl)piperidin-1-yl)-2-methoxybenzonitrile

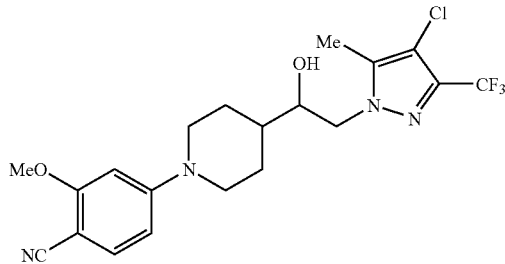

Step 1: A mixture of methyl 4-bromo-2-methoxybenzoate (2.66 g, 10.85 mmol), 28% ammonium hydroxide (25 mL, 642 mmol) and ammonium chloride (2.0 g, 37.4 mmol) was stirred at RT for 20 min and then at 50° C. Once the material converted forms to an oil (ca. 20 min), the mixture was cooled to RT and more ammonium hydroxide (25 mL, 642 mmol) and ammonium chloride (2.0 g, 37.4 mmol) were added. Upon completion of addition, the reaction mixture was stirred at RT overnight. After this time, the mixture was heated to reflux in an open flask to drive off the excess ammonia and then cooled to RT. The mixture was neutralized with conc. HCl and then extracted with ethyl acetate. The extract was dried ($Na_2SO_4$) and then concentrated to give a residue. The residue was purified by flash chromatography (40 g silica gel cartridge; EtOAc/Hex) to give 4-bromo-2-methoxybenzamide (510 mg, 2.22 mmol, 20% yield) as a white solid.

Step 2: A solution of 4-bromo-2-methoxybenzamide (508 mg, 2.21 mmol) in anhydrous DCM (10 mL) was cooled to 0° C. and then treated with 1,8-diazabicyclo(5.4.0)undec-7-ene (0.991 mL, 6.62 mmol). The mixture was stirred at 0° C. for 15 min, and then treated with phenyl dichlorophosphate (0.660 mL, 4.42 mmol) over 2 min. The reaction was stirred at 0° C. for 10 min, and then warmed to RT where it stirred for 1 h. After this time, the mixture was partitioned between DCM (10 mL) and saturated $NH_4Cl$ (20 mL). The aqueous phase was extracted with DCM. The combined extracts were dried ($MgSO_4$) and concentrated to give the crude product, which was purified by flash chromatography (12 g $SiO_2$ column; 0-30% EtOAc/Hex gradient) to give 4-bromo-2-methoxybenzonitrile (250 mg, 1.18 mmol, 53% yield) as a white solid. $^1$H-NMR (400 MHz, $CDCl_3$) δ ppm 7.40 (1H, s), 7.16 (1H, s), 7.12 (1H, s), 3.91 (3H, s).

Step 3: A 50-mL round bottom flask was charged with 2-(4-chloro-5-methyl-3-(trifluoromethyl)-1H-pyrazol-1-yl)-1-(piperidin-4-yl)ethanol (50 mg, 0.160 mmol), 4-bromo-2-methoxybenzonitrile (37.4 mg, 0.176 mmol), tris(dibenzylideneacetone)dipalladium(0) (14.69 mg, 0.016 mmol), rac-2,2'-bis(diphenylphosphino)-1,1'-binaphthyl (19.97 mg, 0.032 mmol) and sodium tert-butoxide (38.5 mg, 0.401 mmol). The flask was purged with nitrogen and charged with anhydrous toluene (3.0 mL). The mixture was stirred at 100° C. for 30 min. After this time, the mixture was cooled, treated with brine and extracted with EtOAc. The extract was dried and concentrated in vacuo to give the crude product. The crude product was purified by preparative HPLC (method f) to give Example 15f (12 mg, 0.027 mmol, 17% yield) as a white solid. LC-MS: 443.21, [M+H]$^+$; $t_R$=3.61 min (method b). $^1$H-NMR (400 MHz, $CDCl_3$) δ ppm 7.38 (1H, d, J=8.57 Hz), 6.37-6.59 (2H, m), 4.13-4.24 (1H, m), 3.99-4.07 (1H, m), 3.83-3.99 (5H, m), 2.84-3.00 (2H, m), 2.75 (1H, s), 2.30 (3H, s), 2.00 (1H, d, J=12.74 Hz), 1.84 (1H, d, J=12.08 Hz), 1.47-1.79 (3H, m).

Example 16

1-(4-Chloro-3-methoxyphenyl)-4-(2-(4-chloro-5-methyl-3-(trifluoromethyl)-1H-pyrazol-1-yl)-1-(5-methyl-1H-tetrazol-1-yl)ethyl)piperidine

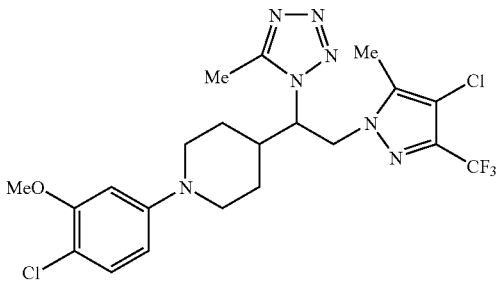 [SMILES: COc1cc(N2CCC(C(Cn3nc(C(F)(F)F)c(Cl)c3C)n3nnnc3C)CC2)ccc1Cl]

Step 1: A solution of 1-(1-(4-chloro-3-methoxyphenyl)piperidin-4-yl)-2-(4-chloro-5-methyl-3-(trifluoromethyl)-1H-pyrazol-1-yl)ethanone (825 mg, 1.832 mmol) in DCM (5 mL) was treated with ammonia (9.16 mL of a 2.0 M solution in EtOH, 18.32 mmol) and stirred at RT in a sealed flask for 20 min. The flask was then charged with titanium(IV) isopropoxide (2.163 mL, 7.33 mmol) and re-sealed. The reaction mixture was stirred at RT for 16 h before being treated with sodium borohydride (0.259 mL, 7.33 mmol) in small portions. The resulting mixture was stirred at RT for 30 min, after which time the mixture had become thick and foamy. DCM (5 mL) was added to the reaction mixture in order to facilitate stirring and the reaction continued for an additional 1.5 h. After this time, the mixture was treated with concentrated ammonium hydroxide (10 mL) and DCM (15 mL), stirred vigorously at RT for 20 min and then filtered through Celite. The filtrate was placed in a separatory funnel and the phases were separated. The aqueous phase was extracted with DCM, and the combined DCM extracts were dried (Na$_2$SO$_4$) and concentrated on a rotary evaporator to give the crude product. The crude product was purified by flash chromatography (40 g silica gel cartridge; 40% EtOAc/Hex used to elute the less polar materials; 3% MeOH in EtOAc used to elute the amine) to afford 1-(1-(4-chloro-3-methoxyphenyl)piperidin-4-yl)-2-(4-chloro-5-methyl-3-(trifluoromethyl)-1H-pyrazol-1-yl) ethanamine (500 mg, 1.108 mmol, 60% yield) as a clear gum. LC-MS: 451.19, [M+H]$^+$; t$_R$=3.07 min (b).

Step 2: A solution of 1-(1-(4-chloro-3-methoxyphenyl)piperidin-4-yl)-2-(4-chloro-5-methyl-3-(trifluoromethyl)-1H-pyrazol-1-yl)ethanamine (49 mg, 0.109 mmol) in anhydrous DCM (1.5 mL) was treated with acetic anhydride (0.012 mL, 0.130 mmol) and DMAP (1.3 mg, 11 μmol), and the resultant mixture was stirred at RT for 1.5 h. After this time, the mixture was diluted with DCM (5 mL) and then washed sequentially with saturated NaHCO$_3$ and brine. The organic extract was dried (MgSO$_4$) and concentrated in vacuo to give N-(1-(1-(4-chloro-3-methoxyphenyl)piperidin-4-yl)-2-(4-chloro-5-methyl-3-(trifluoromethyl)-1H-pyrazol-1-yl)ethyl)acetamide (49 mg), which was used without further purification in the reaction below. LC-MS: 493.25, [M+H]$^+$; t$_R$=3.08 min (method b).

Step 3: A solution of N-(1-(1-(4-chloro-3-methoxyphenyl)piperidin-4-yl)-2-(4-chloro-5-methyl-3-(trifluoromethyl)-1H-pyrazol-1-yl)ethyl)acetamide (49 mg, 0.10 mmol) in anhydrous THF (1.5 mL) was treated with triphenylphosphine (85 mg, 0.326 mmol) and stirred until homogenous. The solution was then treated sequentially with diethyl azodicarboxylate (0.017 mL, 0.109 mmol) and azidotrimethylsilane (0.043 mL, 0.326 mmol), which resulted in the immediate formation of a thick white mixture. The reaction was continued at RT for 14 h, diluted with water (5 mL), and then extracted with EtOAc. The extract was dried (Na$_2$SO$_4$) and concentrated. The resultant residue was purified by preparative HPLC (method f) to give Example 16 (28 mg, 0.054 mmol, 50% yield) as a white solid. LC-MS: 518.26, [M+H]$^+$; t$_R$=3.31 min (method b). $^1$H-NMR (400 MHz, CDCl$_3$) δ ppm 7.43 (1H, d, J=8.56 Hz), 7.18-7.25 (1H, m), 6.83 (1H, dd, J=8.56, 2.52 Hz), 4.84-4.99 (1H, m), 4.63-4.75 (1H, m), 4.51-4.62 (1H, m), 3.91 (3H, s), 3.87 (1H, d, J=13.35 Hz), 3.69 (1H, d, J=12.59 Hz), 3.05-3.27 (2H, m), 2.47-2.63 (1H, m), 2.26-2.46 (5H, m, CH$_3$ and CH$_2$), 2.02-2.13 (1H, m), 1.98 (3H, s), 1.40 (1H, d, J=16.62 Hz).

Example 17

N-(1-(1-(4-Chloro-3-methoxyphenyl)piperidin-4-yl)-2-(4-chloro-5-methyl-3-(trifluoromethyl)-1H-pyrazol-1-yl)ethyl)isonicotinamide

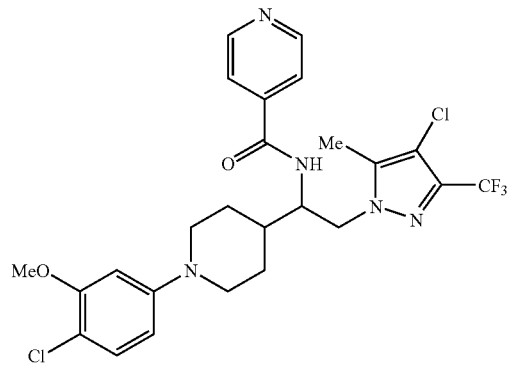

A solution of 1-(1-(4-chloro-3-methoxyphenyl)piperidin-4-yl)-2-(4-chloro-5-methyl-3-(trifluoromethyl)-1H-pyrazol-1-yl)ethanamine (27 mg, 0.060 mmol) in anhydrous DCM (1.5 mL) was treated with triethylamine (0.025 mL, 0.179 mmol), isonicotinoyl chloride hydrochloride (10.65 mg, 0.060 mmol) and DMAP (0.7 mg, 6 μmol). The resultant mixture was stirred at RT for 2 h and then diluted with DCM (10 mL) before being washed sequentially with saturated NaHCO$_3$ and brine. The organic extract was dried and concentrated in vacuo to give the crude product. The crude product was purified by flash chromatography using a 4 g silica gel cartridge and gradient elution from 10 to 40% EtOAc/Hex to give Example 17 (10 mg, 0.018 mmol, 30% yield). LC-MS: 556.22, [M+H]$^+$; t$_R$=2.95 min (method b). $^1$H-NMR (400 MHz, CD$_3$OD) δ ppm 8.54 (2H, d, J=5.54 Hz), 7.51 (2H, d, J=6.04 Hz), 7.03 (1H, d, J=8.56 Hz), 6.53 (1H, d, J=2.01 Hz), 6.41 (1H, dd, J=8.56, 2.27 Hz), 4.51 (1H, d, J=13.35 Hz), 4.06-4.33 (2H, m), 3.73 (3H, s), 3.64 (2H, t, J=12.59 Hz), 2.45-2.76 (2H, m), 2.23 (3H, s), 1.87 (2H, dd, J=45.95, 11.71 Hz), 1.65-1.78 (1H, m, J=15.36 Hz), 1.29-1.63 (2H, m).

Utility

In general, compounds of the present invention, such as particular compounds disclosed in the preceding examples, have been shown to be modulators of chemokine receptor activity (for example, by displaying Ki values<3,300 nM in a binding assay such as those set forth below). By displaying activity as modulators of chemokine receptor activity, compounds of the present invention are expected to be useful in the treatment of human diseases associated with chemokines and their cognate receptors.

Antagonism of MIP-1α Binding to Human THP-1 Cells

Compounds of the present invention have activity in the antagonism of MIP-1α binding to human THP-1 cells described here.

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration of compound, is combined with 50 μl of $^{125}$-I labeled human MIP-1α (to give a final concentration of 50 pM radioligand) and 50 μl of binding buffer containing $5 \times 10^5$ cells. Cells used for such binding assays can include the THP-1 cell line, which expresses the endogenous CCR1 receptor, or human peripheral blood mononuclear cells, isolated by Ficoll-Hypaque gradient centrifugation, or human monocytes (Weiner et al., *J. Immunol. Methods*, 1980, 36, 89). The mixture of compound, cells and radioligand is incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MIP-1α in place of the test compound.

Compounds of the present invention were tested in the assay described immediately above and the results shown in Table 6 below were obtained.

TABLE 6

| Example | CCR1 Binding Ki (n = 1 unless otherwise noted) | Comment |
|---|---|---|
| 2c | ~2,220 nM | Racemic |
| 2f | 114 nM | Racemic |
| 2h | 156 nM | Racemic |
| 4a | 125 nM | Racemic |
| 4c | 6.8 nM | Racemic |
| 4i | 5.15 ± 1.68 nM (n = 4) | Racemic |
| 4n | 3.46 ± 0.48 nM (n = 4) | Diastereomeric mixture |
| 4p | 4.3 nM | Racemic |
| 5b | ~2,200 nM | Enantiomer 2 |
| 5c | 145 nM | Enantiomer 2 |
| 11 | ~1,250 nM | Racemic |
| 15b | 1020 nM | Racemic |

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjorgren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisakis* sp., *Phocanema* sp.), cutaneous larva migraines (*Ancylostoma braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone and pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (n) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound of Formula (I):

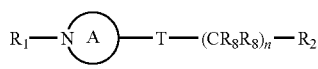
(I)

or stereoisomers or pharmaceutically acceptable salt forms thereof, wherein:

Ring A is

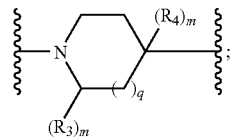

T is

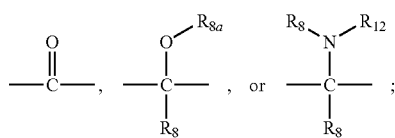

$R_1$ is aryl, which may be optionally substituted with one or more $R_{1a}$;

$R_{1a}$, at each occurrence, is independently selected from halo, —CN, or —O(CR$_8$R$_8$)$_r$R$_{10}$;

$R_2$ is pyrazol optionally substituted with one or more $R_{2a}$ wherein the pyrazol is attached via a nitrogen heteroatom;

$R_{2a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{10}$, —O(CR$_8$R$_8$)$_r$R$_{10}$, —OH, —SH, —S(CR$_8$R$_8$)$_r$R$_{10}$, —C(=O)NR$_9$R$_9$, —NR$_9$R$_9$ or =O, wherein the alkyl, aryl, cycloalkyl, heteroaryl, heterocyclyl and aryloxy may be optionally substituted with one or more $R_{2b}$;

$R_{2b}$, at each occurrence, is independently selected from alkyl, haloalkyl, aryl cycloalkyl cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CR$_8$R$_8$)$_r$R$_{10}$, —OH, —SH, or —NR$_9$R$_9$;

$R_3$ is alkyl;

$R_4$, at each occurrence, is F, alkyl or —OR$_9$;

$R_8$, at each occurrence, is independently hydrogen or alkyl;

$R_{8a}$, at each occurrence, is independently hydrogen, alkyl or —C(=O)(CR$_8$R$_8$)$_r$R$_{15}$;

$R_9$, at each occurrence, is independently hydrogen, alkyl or aryl, wherein the alkyl or aryl may be optionally substituted with one or more $R_{9a}$;

$R_{9a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$ R$_{14}$, —OH, —SH, —S(CR$_8$R$_8$)$_r$R$_{14}$, —C(=O)NR$_{14}$R$_{14}$ or —NR$_{14}$R$_{14}$;

$R_{10}$, at each occurrence, is independently selected from alkyl or aryl, wherein the alkyl or aryl may be optionally substituted with one or more $R_{10a}$;

$R_{10a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$ R$_{14}$, —OH, —SH, —S(CR$_8$R$_8$)$_r$R$_{14}$, —C(=O)NR$_{14}$R$_{14}$ or —NR$_{14}$R$_{14}$;

$R_{12}$ is hydrogen, alkyl, heteroaryl, —S(O)$_2$R$_{15}$, —C(=O)NH$_2$, —C(=O)NR$_8$R$_{15}$, or —C(=O)OR$_{15}$, wherein the alkyl or heteroaryl may be optionally substituted with one or more $R_{12a}$, and the heteroaryl contains 1-4 heteroatoms selected from N, O, and S;

$R_{12a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$ R$_{14}$, —OH, —SH, —S(CR$_8$R$_8$)$_r$R$_{14}$, —C(=O)NR$_{14}$R$_{14}$ or —NR$_{14}$R$_{14}$;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$ R$_{14}$, —OH, —SH, —S(CR$_8$R$_8$)$_r$R$_{14}$, —C(=O)NR$_{14}$R$_{14}$ or —NR$_{14}$R$_{14}$;

m, at each occurrence, is independently 0-2;

n is 1-2;

q is 1; and r, at each occurrence, is independently 0-2.

2. The compound of claim 1, or stereoisomers or pharmaceutically acceptable salt forms thereof, wherein
Ring A is

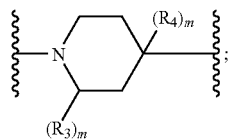

T is

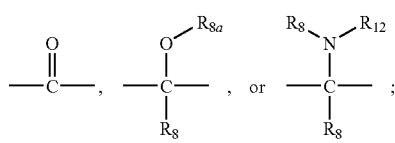

$R_1$ is phenyl, which may be optionally substituted with one or more $R_{1a}$;

$R_{1a}$, at each occurrence, is independently selected from halo, —CN, or —O(CR$_8$R$_8$)$_r$R$_{10}$;

$R_2$ is pyrazol optionally substituted with one or more $R_{2a}$ wherein the pyrazol is attached via a nitrogen heteroatom;

$R_{2a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{10}$, —O(CR$_8$R$_8$)$_r$R$_{10}$, —OH, —C(=O)NR$_9$R$_9$, —NR$_9$R$_9$ or =O, wherein the alkyl, aryl, cycloalkyl, heteroaryl, heterocyclyl and aryloxy may be optionally substituted with one or more $R_{2b}$;

$R_{2b}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{10}$, —O(CR$_8$R$_8$)$_r$R$_{10}$, —OH, —SH, or —NR$_9$R$_9$;

$R_3$ is alkyl;

$R_4$, at each occurrence, is alkyl or —OR$_9$;

$R_8$, at each occurrence, is independently hydrogen or alkyl;

$R_{8a}$, at each occurrence, is independently hydrogen, alkyl or —C(=O)(CR$_8$R$_8$)$_r$R$_{15}$;

$R_9$, at each occurrence, is independently hydrogen, alkyl or aryl, wherein the alkyl or aryl may be optionally substituted with one or more $R_{9a}$;

$R_{9a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —C(=O)NR$_{14}$R$_{14}$ or —NR$_{14}$R$_{14}$;

$R_{10}$, at each occurrence, is independently selected from alkyl or aryl, wherein the alkyl or aryl may be optionally substituted with one or more $R_{10a}$;

$R_{10a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —C(=O)NR$_{14}$R$_{14}$ or —NR$_{14}$R$_{14}$;

$R_{12}$ is alkyl, heteroaryl, —S(O)$_2$R$_{15}$, —C(=O)R$_{15}$, —C(=O)NH$_2$, —C(=O)NR$_8$R$_{15}$, or —C(=O)OR$_{15}$, wherein the alkyl or heteroaryl may be optionally substituted with one or more $R_{12a}$, and the heteroaryl contains 1-4 heteroatoms selected from N, O, and S;

$R_{12a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —C(=O)NR$_{14}$R$_{14}$ or —NR$_{14}$R$_{14}$;

$R_{14}$, at each occurrence, is independently selected from hydrogen, alkyl, cycloalkyl or phenyl;

$R_{15}$, at each occurrence, is independently selected from alkyl, cycloalkyl or phenyl, all of which may be optionally substituted with one or more $R_{15a}$;

$R_{15a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —C(=O)NR$_{14}$R$_{14}$ or —NR$_{14}$R$_{14}$;

m, at each occurrence, is independently 0-2;

n is 1-2; and r, at each occurrence, is independently 0-2.

3. The compound of claim 1, or stereoisomers or pharmaceutically acceptable salt forms thereof, wherein
Ring A is

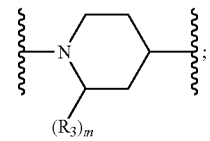

T is

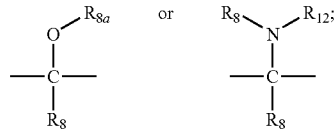

$R_1$ is phenyl, which may be optionally substituted with one or more $R_{1a}$;

$R_{1a}$, at each occurrence, is independently selected from halo, —CN, or —O(CR$_8$R$_8$)$_r$R$_{10}$;

$R_2$ is pyrazol optionally substituted with one or more $R_{2a}$ wherein the pyrazol is attached via a nitrogen heteroatom;

$R_{2a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{10}$, —O(CR$_8$R$_8$)$_r$R$_{10}$, —OH or =O, wherein the alkyl, aryl, cycloalkyl, heteroaryl, heterocyclyl and aryloxy may be optionally substituted with one or more $R_{2b}$;

$R_{2b}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{10}$, —O(CR$_8$R$_8$)$_r$R$_{10}$, or —OH;

$R_3$ is alkyl;

$R_8$, at each occurrence, is independently hydrogen or alkyl;

$R_{8a}$, at each occurrence, is independently hydrogen, alkyl or —C(=O)(CR$_8$R$_8$)$_r$R$_{15}$;

$R_{10}$, at each occurrence, is independently selected from alkyl or aryl, wherein the alkyl or aryl may be optionally substituted with one or more $R_{10a}$;

R$_{10a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CR$_8$R$_8$)$_r$R$_{14}$, —C(=O)NR$_{14}$R$_{14}$ or —NR$_{14}$R$_{14}$;

R$_{12}$ is alkyl, heteroaryl, —S(O)$_2$R$_{15}$, —C(=O)R$_{15}$, —C(=O)NH$_2$, —C(=O)NR$_8$R$_{15}$, or —C(=O)OR$_{15}$, wherein the alkyl or heteroaryl may be optionally substituted with one or more R$_{12a}$, and the heteroaryl contains 1-4 heteroatoms selected from N, O, and S;

R$_{12a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CR$_8$R$_8$)$_r$R$_{14}$, —OH, —C(=O)NR$_{14}$R$_{14}$ or —NR$_{14}$R$_{14}$;

R$_{14}$, at each occurrence, is independently selected from hydrogen, alkyl, cycloalkyl or phenyl;

R$_{15}$, at each occurrence, is independently selected from alkyl, cycloalkyl or phenyl, all of which may be optionally substituted with one or more R$_{15a}$;

R$_{15a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{14}$, —O(CR$_8$R$_8$)$_r$R$_{14}$, —OH, or —NR$_{14}$R$_{14}$;

m, at each occurrence, is independently 0-2;
n is 1-2; and
r, at each occurrence, is independently 0 or 1.

4. The compound of claim 1, or stereoisomers or pharmaceutically acceptable salt forms thereof, wherein
Ring A is

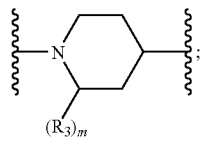

T is

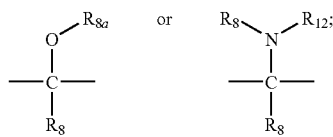

R$_1$ is phenyl, which may be optionally substituted with one or more R$_{1a}$;

R$_{1a}$, at each occurrence, is independently selected from halo, —CN, or —O(CR$_8$R$_8$)$_r$R$_{10}$;

R$_2$ is pyrazolyl optionally substituted with one or more R$_{2a}$ and wherein pyrazolyl is attached via a nitrogen heteroatom;

R$_{2a}$, at each occurrence, is independently selected from alkyl, haloalkyl, aryl, cycloalkyl, heteroaryl, heterocyclyl, halo, —NH$_2$, —CN, —NO$_2$, —C(=O)OH, —C(=O)O(CR$_8$R$_8$)$_r$R$_{10}$, —O(CR$_8$R$_8$)$_r$R$_{10}$, —OH or =O;

R$_3$ is alkyl;
R$_8$, at each occurrence, is independently hydrogen or alkyl;
R$_{8a}$, at each occurrence, is independently hydrogen, alkyl or —C(=O)(CR$_8$R$_8$)$_r$R$_{15}$;

R$_{10}$, at each occurrence, is independently selected from alkyl or aryl, wherein the alkyl or aryl may be optionally substituted with one or more R$_{10a}$;

R$_{10a}$, at each occurrence, is independently selected from alkyl, haloalkyl, aryl, cycloalkyl, heteroaryl, heterocyclyl, halo, —NH$_2$, —CN, —O(CR$_8$R$_8$)$_r$R$_{14}$, —OH, —C(=O)NR$_{14}$R$_{14}$ or —NR$_{14}$R$_{14}$;

R$_{12}$ is alkyl, heteroaryl, —S(O)$_2$R$_{15}$, —C(=O)R$_{15}$, —C(=O)NH$_2$, —C(=O)NR$_8$R$_{15}$, or —C(=O)OR$_{15}$, wherein the alkyl or heteroaryl may be optionally substituted with one or more R$_{12a}$, and the heteroaryl contains 1-4 heteroatoms selected from N, O, and S;

R$_{12a}$, at each occurrence, is independently selected from alkyl, haloalkyl, aryl, cycloalkyl; heteroaryl, heterocyclyl, halo, —NH$_2$, —CN, —O(CR$_8$R$_8$)$_r$R$_{14}$, —OH, —C(=O)NR$_{14}$R$_{14}$ or —NR$_{14}$R$_{14}$, R$_{14}$, at each occurrence, is independently selected from hydrogen, alkyl, cycloalkyl or phenyl;

R$_{15}$, at each occurrence, is independently selected from alkyl, cycloalkyl or phenyl, all of which may be optionally substituted with one or more R$_{15a}$;

R$_{15a}$, at each occurrence, is independently selected from alkyl, haloalkyl, aryl, cycloalkyl, heteroaryl, heterocyclyl, halo, —NH$_2$, —CN, —O(CR$_8$R$_8$)$_r$R$_{14}$, —OH, or —NR$_{14}$R$_{14}$;

m, at each occurrence, is independently 0-2;
n is 1-2; and
r, at each occurrence, is independently 0 or 1.

5. A compound of claim 1, or an enantiomer, diastereomer or pharmaceutically acceptable salt, selected from:
- 1-(1-(4-Chloro-3-methoxyphenyl)piperidin-4-yl)-2-(4-chloro-5-methyl-3-(trifluoromethyl)-1H-pyrazol-1-yl)ethanone;
- 1-(1-(4-Chloro-3-methoxyphenyl)piperidin-4-yl)-2-(4-chloro-5-methyl-3-(pyridin-2-yl)-1H-pyrazol-1-yl)ethanone;
- 2-(3-Amino-1H-pyrazolo[3,4b]pyridin-1-yl)-1-(1-(4-chloro-3-methoxyphenyl)piperidin-4-yl)ethanone;
- 1-(1-(4-Chloro-3-methoxyphenyl)piperidin-4-yl)-2-(4-iodo-1H-pyrazol-1-yl)ethanone;
- 2-(4-Chloro-1H-pyrazol-1-yl)-1-(1-(4-chloro-3-methoxyphenyl)piperidin-4-yl)ethanone;
- 4-Bromo-1-(2-(1-(4-chloro-3-methoxyphenyl)piperidin-4-yl)-2-oxoethyl)-1H-pyrazole-3-carbonitrile;
- 1-(1-(4-Chloro-3-methoxyphenyl)piperidin-4-yl)-2-(5-methyl-3-(pyridin-2-yl)-1H-pyrazol-1-yl)ethanone;
- 2-(4-Chloro-5-methyl-3-(trifluoromethyl)-1H-pyrazol-1-yl)-1-(1-(2,4-dichloro-5-methoxyphenyl)piperidin-4-yl)ethanone ;
- 1-(1-(4-Chloro-3-methoxyphenyl)piperidin-4-yl)-2-(4-chloro-5-methyl-3-(trifluoromethyl)-1H-pyrazol-1-yl)ethanol;
- 1-(1-(4-Chloro-3-methoxyphenyl)piperidin-4-yl)-2-(4-chloro-5-methyl-3-(pyridin-2-yl)-1H-pyrazol-1-yl)ethanol;
- 2-(3-Amino-1H-pyrazolo [3,4b]pyridin-1-yl)-1-(1-(4-chloro-3-methoxyphenyl)piperidin-4-yl)ethanol;
- 1-(1-(4-Chloro-3-methoxyphenyl)piperidin-4-yl)-2-(5-methyl-3-(trifluoromethyl)-1H-pyrazol-1-yl)ethanol;
- 2-(4-Bromo-1H-pyrazol-1-yl)-1-(1-(4-chloro-3-methoxyphenyl)piperidin-4-yl)ethanol ;
- 1-(1-(4-Chloro-3-methoxyphenyl)piperidin-4-yl)-2-(5-(trifluoromethyl)-1H-pyrazol-1-yl)ethanol;
- 1-(1-(4-Chloro-3-methoxyphenyl)piperidin-4-yl)-2-(4-chloro-5-phenyl-3-(trifluoromethyl)-1H-pyrazol-1-yl)ethanol;

2-(4-Chloro-5-methyl-3-(pyridin)-2-yl)-1H-pyrazol-1-yl)-1-(1-(2,4-dichloro-5-methoxyphenyl)piperidin-4-yl)ethanol;

2-(4-Chloro-5-methyl-3-(trifluoromethyl)-1H-pyrazol-1-yl)-1-(1-(2,4-dichloro-5-methoxyphenyl)piperidin-4-yl)ethanol;

2-(4-Chloro-5-methyl-3-(trifluoromethyl)-1H-pyrazol-1-yl)-1-(1-(2,4-dichloro-5-methoxyphenyl)piperidin-4-yl)ethyl acetate;

2-(4-Chloro-5-methyl-3-(trifluoromethyl)-1H-pyrazol-1-yl)-1-(1-(2,4-dichloro-5-methoxyphenyl)piperidin-4-yl)ethanamine;

2-(4-Chloro-5-methyl-3-(trifluoromethyl)-1H-pyrazol-1-yl)-1-(1-(2,4-dichloro-5-methoxyphenyl)piperidin-4-yl)-N-methylethanamine;

N-(2-(4-Chloro-5-methyl-3-(trifluorormethyl)-1H-pyrazol-1-yl)-1-(1-(2,4-dichloro-5-methoxyphenyl)piperidin-4-yl)ethyl)acetamide;

1-(2-(4-Chloro-5-methyl-3-(trifluoromethyl)-1H-pyrazol-1-yl)-1-(1-(2,4-dichloro-5-methoxyphenyl)piperidin-4-yl)ethyl)urea;

1-(2-(4-Chloro-5-methyl-3-(trifluoromethyl)-1H-pyrazol-1-yl)-1-(1-(2,4-dichloro-5-methoxyphenyl)piperidin-4-yl)ethyl)-3-methylurea;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)thiazol-2-amine;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)methanesulfonamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-(dimethylamino)acetamide, TFA salt;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-hydroxyacetamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)benzamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)benzenesulfonamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)isobutyramide;

(2S)-N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-hydroxypropanamide;

(2R)-N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-hydroxypropanamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-(methylamino)acetamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)-2-fluoroacetamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)propionamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)butyramide;

2-Amino-N-(2-(4-chloro-5-methyl-3-(trifluoromethyl)-1H-pyrazol-1-yl)-1-(2,4-dichloro-5-methoxyphenyl)piperidin-4-yl)ethyl)acetamide;

N-(2-(4-Chloro-5-methyl-3-(trifluoromethyl)-1H-pyrazol-1-yl)-1-(1-(2,4-dichloro-5-methoxyphenyl)piperidin-4-yl)ethyl)cyclopropanecarboxamide;

(2S)-2-Amino-N-(2-(4-chloro-5-methyl-3-(trifluoromethyl)-1H-pyrazol-1-yl)-1-(1-(2,4-dichloro-5-methoxyphenyl)piperidin-4-yl)ethyl)-3-hydroxypropanamide;

(2S)-2-Amino-N-(2-(4-chloro-5-methyl-3-(trifluoromethyl)-1H-pyrazol-1-yl)-1-(1-(2,4-dichloro-5-methoxyphenyl)piperidin-4-yl)ethyl)-3-hydroxypropanamide;

N-(1-(1-(4-Chloro-3-methoxyphenyl)piperidin-4-yl)-2-(5-methyl-3-(trifluoromethyl)-1H-pyrazol-1-yl)ethyl)acetamide;

N-(1-(1-(4-chloro-3-methoxyphenyl)piperidin-4-yl)-2-(5-methyl-3-(trifluoromethyl)-1H-pyrazol-1-yl)ethyl)-2-hydroxyaectamide;

2-amino-N-(1-(1-(4-chloro-3-methoxyphenyl)piperidin-4-yl)-2-(5-methyl-3-(trifluoromethyl)-1H-pyrazol-1-yl)ethyl)acetamide;

(R)-N-(1-(1-(4-chloro-3-methoxyphenyl)piperidin-4-yl)-2-(5-methyl-3-(trifluorormethyl)-1H-pyrazol-1-yl)ethyl)-2-hydroxypropanamide);

4-(2-((4-Chloro-5-methyl-3-(trifluoromethyl)-1H-pyrazol-1-yl)methyl)-1,3-dioxolan-2-yl)-1-(2,4-dichloro-5-methoxyphenyl)piperidine;

2-(4-Chloro-5-methyl-3-(trifluoromethyl)-1H-pyrazol-1-yl)-1-(1-(2,4-dichloro-5-ethoxyphenyl)piperidin-4-ethanol;

2-(4-Chloro-5-methyl-3-(trifluoromethyl)-1H-pyrazol-1-yl)-1-(1-(2,4-dichloro-5-isopropoxyphenyl)piperidin-4-yl)ethanol;

2-(4-Chloro-5-methyl-3-(trifluorormethyl)-1H-pyrazol-1-yl)-1-(1-(2,4-dichloro-5-(2-hydroxyethoxy)phenyl)piperidin-4-yl)ethanol;

4-(1-(4-Chloro-5-methyl-3-(trifluoromethyl)-1H-pyrazol-1-yl)propan-2-yl)-1-(2,4-dichloro-5-methoxyphenyl)piperidine;

1-(1-(4-Chloro-3-methoxyphenyl)-4-methylpiperidin-4-yl)-2-(4-chloro-5-methyl-3-(trifluoromethyl)-1H-pyrazol-1-yl)ethanol;

1-(1-(4-Chloro-3-methoxyphenyl)piperidin-4-yl)-2-(4-chloro-5-methyl-3-(trifluoromethyl)-1H-pyrazol-1-yl)propan-1-ol;

1-(1-(2-Bromo-4-chloro-5-methoxyphenyl)piperidin-4-yl)-2-(4-chloro-5-methyl-3-(trifluoromethyl)-1H-pyrazol-1-yl)propan-1-ol;

1-(4-Chloro-3-methoxyphenyl)-4-(2-(4-chloro-5-methyl-3-(trifluoromethyl)-1H-pyrazol-1-yl)-1-yl)-1-hydroxyethyl)piperidin-4-ol;

4-(2-(4-Chloro-5-methyl-3-(trifluoromethyl)-1H-pyrazol-1-yl)ethyl)-1-(2,4-dichloro-5-methoxyphenyl)piperidin-4-ol;

2-(4-Chloro-5-methyl-3-(trifluoromethyl)-1H-pyrazol-1-yl)-1-(1-(4-chlorophenyl)piperidin-4-yl)ethanol;

2-(4-Chloro-5-methyl-3-(trifluoromethyl)-1H-pyrazol-1-yl)-1-(1-(3-methoxyphenyl)piperidin-4-yl)ethanol ;

2-(4-Chloro-5-methyl-3-(trifluoromethyl)-1H-pyrazol-1-yl)-1-(1-(4-fluorophenyl)piperidin-4-yl)ethanol ;

1-(1-(2-Chloro-5-methoxyphenyl)piperidin-4-yl)-2-(4-chloro-5-methyl-3-(trifluoromethyl)-1H-pyrazol-1-yl)ethanol ;

2-(4-Chloro-5-methyl-3-(trifluoromethyl)-1H-pyrazol-1-yl)-1-(1-(2-chlorophenyl)piperidin-4-yl)ethanol;

4-(4-(2-(4-Chloro-5-methyl-3-(trifluoromethyl)-1H-pyrazol-1-yl)acetyl)piperidin-1-yl)-2-methoxybenzonitrile;

1-(4-Chloro-3-methoxyphenyl)-4-(2-(4-chloro-5-methyl-3-(trifluoromethyl)-1H-pyrazol-1-yl)-1-(5-methyl-1H-tetrazol-1-yl)ethyl)piperidine; and N-(1-(1-(4-Chloro-3-methoxyphenyl)piperidin-4-yl)-2-(4-chloro-5-methyl-3-(trifluoromethyl)-1H-pyrazol-1-1-yl)ethyl)isonicotinamide.

6. A pharmaceutical composition comprised of a pharmaceutically acceptable carrier and a therapeutically effective amount of a compound of claim 1.

7. The method of treating rheumatoid arthritis comprising administering to a patient in need thereof, a therapeutically effective amount of at least one compound of claim 1.

* * * * *

UNITED STATES PATENT AND TRADEMARK OFFICE
CERTIFICATE OF CORRECTION

PATENT NO. : 8,354,432 B2  
APPLICATION NO. : 12/444249  
DATED : January 15, 2013  
INVENTOR(S) : Percy H. Carter et al.

Page 1 of 1

It is certified that error appears in the above-identified patent and that said Letters Patent is hereby corrected as shown below:

In the Claims:

Claim 1:

Column 92, line 6, change "aryl cycloalkyl" to -- aryl, cycloalkyl, --.

Claim 2:

Column 93, line 46, change "—C(=O)(CR$_8$R$_8$),R$_{15}$;" to -- —C(=O)(CR$_8$R$_8$)$_r$R$_{15}$; --.

Column 94, line 16, change "—O(CF$_2$),CF$_3$," to -- —O(CF$_2$)$_r$CF$_3$, --.

Claim 3:

Column 95, line 4, after "—O(CR$_8$R$_8$)$_r$R$_{14}$,", insert -- —OH, --.

Claim 4:

Column 96, line 15, change "cycloalkyl;" to -- cycloalkyl, --.

Signed and Sealed this  
Eighteenth Day of March, 2014

Michelle K. Lee  
*Deputy Director of the United States Patent and Trademark Office*